US012674167B2

(12) United States Patent
Kim et al.

(10) Patent No.: US 12,674,167 B2
(45) Date of Patent: Jul. 7, 2026

(54) APTAMER SPECIFICALLY BINDING TO CANCER STEM CELLS, AND USE THEREOF

(71) Applicant: HiCELL Tech, Yangsan-si (KR)

(72) Inventors: Jae Ho Kim, Busan (KR); Dae Kyoung Kim, Yangsan-si (KR)

(73) Assignee: HiCELL Tech

( * ) Notice: Subject to any disclaimer, the term of this patent is extended or adjusted under 35 U.S.C. 154(b) by 1308 days.

(21) Appl. No.: 17/593,951

(22) PCT Filed: Mar. 30, 2020

(86) PCT No.: PCT/KR2020/004329

§ 371 (c)(1),
(2) Date: Sep. 28, 2021

(87) PCT Pub. No.: WO2020/197352

PCT Pub. Date: Oct. 1, 2020

(65) Prior Publication Data

US 2022/0251571 A1 Aug. 11, 2022

(30) Foreign Application Priority Data

Mar. 28, 2019 (KR) ........................ 10-2019-0036171

(51) Int. Cl.

| | |
|---|---|
| ***C12N 15/113*** | (2010.01) |
| ***A23L 33/00*** | (2016.01) |
| ***A23L 33/13*** | (2016.01) |
| ***A61K 9/00*** | (2006.01) |
| ***A61K 9/16*** | (2006.01) |
| ***A61K 9/20*** | (2006.01) |
| ***A61K 9/48*** | (2006.01) |
| ***A61K 31/7088*** | (2006.01) |
| ***A61P 35/00*** | (2006.01) |
| ***G01N 33/575*** | (2026.01) |

(52) U.S. Cl.

CPC .......... *C12N 15/1138* (2013.01); *A23L 33/13* (2016.08); *A23L 33/40* (2016.08); *A61K 9/0019* (2013.01); *A61K 9/1611* (2013.01); *A61K 9/1623* (2013.01); *A61K 9/2013* (2013.01); *A61K 9/2018* (2013.01); *A61K 9/2059* (2013.01); *A61K 9/4825* (2013.01); *A61K 9/4858* (2013.01); *A61K 9/4866* (2013.01); *A61K 31/7088* (2013.01); *A61P 35/00* (2018.01); *G01N 33/5759* (2026.01); *A23V 2002/00* (2013.01); *C12N 2310/16* (2013.01); *G01N 2333/70596* (2013.01)

(58) Field of Classification Search

CPC ............ C12N 15/1138; C12N 2310/16; C12N 2310/14; C12N 15/115; A23L 33/13; A23L 33/40; A23L 33/10; A61K 9/0019; A61K 9/1611; A61K 9/1623; A61K 9/2013; A61K 9/2018; A61K 9/2059; A61K 9/4825; A61K 9/4858; A61K 9/4866; A61K 31/7088; A61K 47/549; A61P 35/00; G01N 33/57492; G01N 2333/70596; G01N 33/574; G01N 33/5308; A23V 2002/00; A23V 2200/308; C12Q 1/6886; C12Q 2525/205

See application file for complete search history.

(56) References Cited

FOREIGN PATENT DOCUMENTS

| | | | |
|---|---|---|---|
| KR | 10-2014-0021973 | A | 2/2014 |
| KR | 10-2015-0085806 | A | 7/2015 |
| KR | 10-2016-0029335 | A | 3/2016 |
| KR | 10-2018-0010203 | A | 1/2018 |
| WO | 2014/019024 | A1 | 2/2014 |
| WO | 2014/025234 | A2 | 2/2014 |
| WO | 2014019025 | A1 | 2/2014 |
| WO | 2016/179285 | A1 | 11/2016 |

OTHER PUBLICATIONS

Jin Her, Hunho Jo, Changill Ban, Enzyme-linked antibody aptamer assays based colorimetric detection of soluble fraction of activated leukocyte cell adhesion molecule, Sensors and Actuators B: Chemical, vol. 242, 2017, pp. 529-534, ISSN 0925-4005, https://doi.org/10.1016/j.snb.2016.11.070. (Year: 2017).*

Hassan et al. CD166 as a Stem Cell Marker? A Potential Target for Therapy Colorectal Cancer? J Stem Cell Res Ther 2016, 1(6): 00041 (Year: 2016).*

Lahkin et al. "Aptamers: Problems, Solutions and Prospects". Acta Naturae. Oct.-Dec. 2013;5(4):34-43. (Year: 2013).*

Gupta et al. "Chemically Modified DNA Aptamers Bind Interleukin-6 with High Affinity and Inhibit Signaling by Blocking Its Interaction with Interleukin-6 Receptor". Signal Transduction, vol. 289, Issue 12, p. 8706-8719, Mar. 2014. (Year: 2014).*

Sonkar et al. "CD24 and CD44 expression in Indian breast cancer patients and response to chemotherapy". Poster Abstracts II / The Breast 24S1 (2015) S122. (Year: 2015).*

Krzyszczyk et al. "The growing role of precision and personalized medicine for cancer treatment". (2019). Technology (Singap World Sci). Jan. 11, 2019;6(3-4):79-100. (Year: 2019).*

Weidle et al. "ALCAM/CD166: Cancer-related Issues". Cancer Genomics & Proteomics 7: 231-244 (2010). (Year: 2010).*

Yoshida et al. "Quantitative and sensitive protein detection strategies based on aptamers". (2012). Prot. Clin. Appl., 6: 574-580. (Year: 2012).*

(Continued)

*Primary Examiner* — Brian Whiteman
*Assistant Examiner* — Amanda M Zahorik
(74) *Attorney, Agent, or Firm* — Seed Intellectual Property Law Group LLP

(57) ABSTRACT

The present invention relates to aptamers that specifically bind to cancer stem cells. The aptamers according to the present invention specifically bind to cancer stem cells and reduce cell adhesion ability, cell proliferation, drug resistance and cell migration, which are characteristics of cancer stem cells, thus having excellent anticancer effects. Therefore, the aptamer may be used in various ways in the fields of cancer diagnosis, prognosis prediction, and treatment.

13 Claims, 38 Drawing Sheets

Specification includes a Sequence Listing.

(56) References Cited

OTHER PUBLICATIONS

Ahern. "Biochemical Reagents Kits Offer Scientists Good Return on Investment". The Scientist, vol. 9, #15, p. 20, Jul. 24, 1995. (Year: 1995).*

Chen et al. "Advances in the development of aptamer drug conjugates for targeted drug delivery". WIREs Nanomed Nanobiotechnol 2017, 9:e1438 (Year: 2017).*

Kanwar et al. "Chimeric aptamers in cancer cell-targeted drug delivery". (2011). Critical Reviews in Biochemistry and Molecular Biology, 46(6), 459-477. (Year: 2011).*

Tomasetti and Vogelstein. Variation in cancer risk among tissues can be explained by the number of stem cell divisions. Science. Jan. 2, 2015; 347(6217): 78-81. (Year: 2015).*

Anonymous, "Use of Liquids and/or Soft Foods as Vehicles for Drug Administration: General Considerations for Selection and In Vitro Methods for Product Quality Assessments: Guidance for Industry," U.S. Department of Health and Human Services, Food and Drug Administration, Center for Drug Evaluation and Research (CDER), Jul. 2018. (20 pages).

Extended European Search Report, dated Sep. 25, 2023, for European Application No. 20776943.1. (11 pages).

Her et al., Enzyme-linked antibody aptamer assays based colorimetric detection of soluble fraction of activated leukocyte cell adhesion molecule, *Sensors and Actuators B* 242:529-534, Apr. 2017. (with Supplementary Material) (8 pages).

MacKay et al., "Developing Trends in Aptamer-Based Biosensor Devices and Their Applications," *IEEE Transactions on Biomedical Circuits and Systems* 8(1), Feb. 2014. (11 pages).

Yang et al., "Therapeutic Strategies for Targeting Ovarian Cancer Stem Cells," *International Journal of Molecular Sciences* 22:5059, May 11, 2021. (17 pages).

International Search Report and Written Opinion, dated Jul. 15, 2020, for International Application No. PCT/KR2020/004329. (w/ English Translation) (18 pages).

Ya-Li Han "Development of CD166 Aptamer for Targeting Ovarian Cancer Stem-Like Cells," Thesis for the degree of Master of Medical Science, The Graduate School Pusan National University, Department of Medical Science, Aug. 2016. (48 pages).

Ferragut et al., "ALCAM/CD166: A pleiotropic mediator of cell adhesion, stemness and cancer progression," Cytokine and Growth Factor Reviews 61:27-37(2021).

* cited by examiner

[Fig. 1]
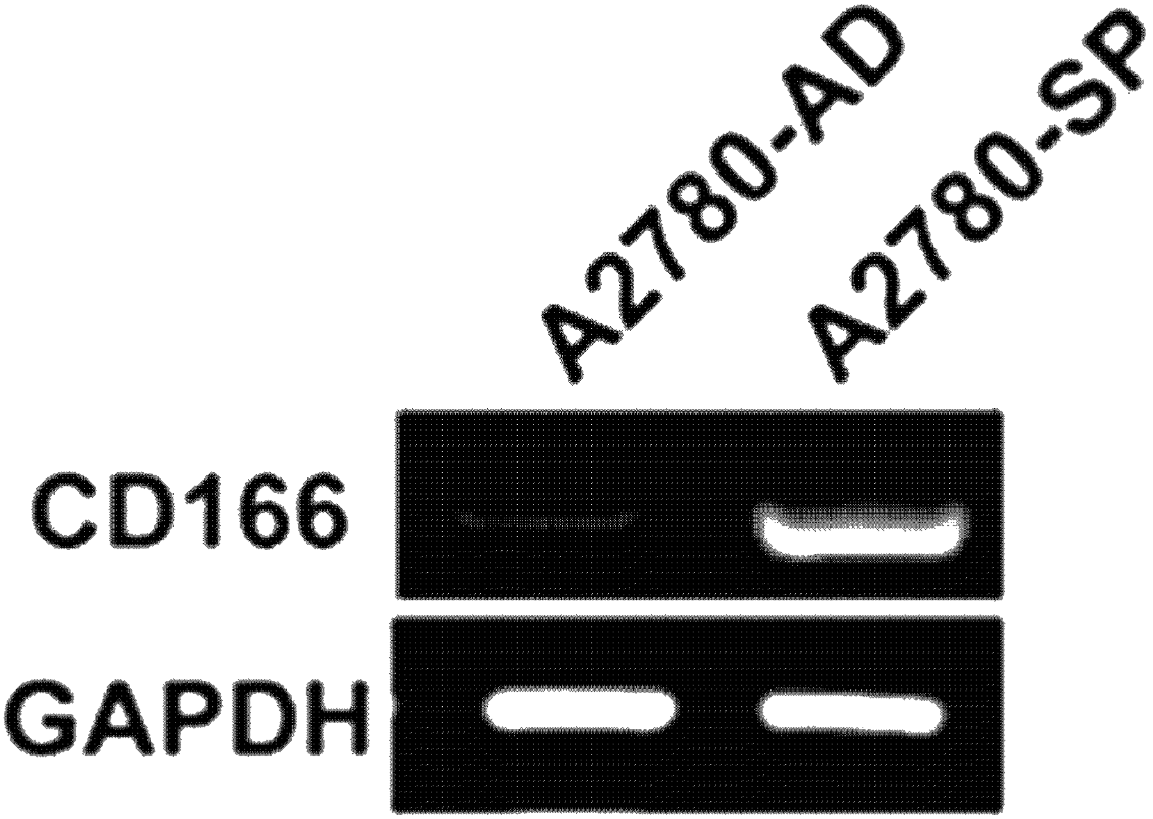

[Fig. 2]
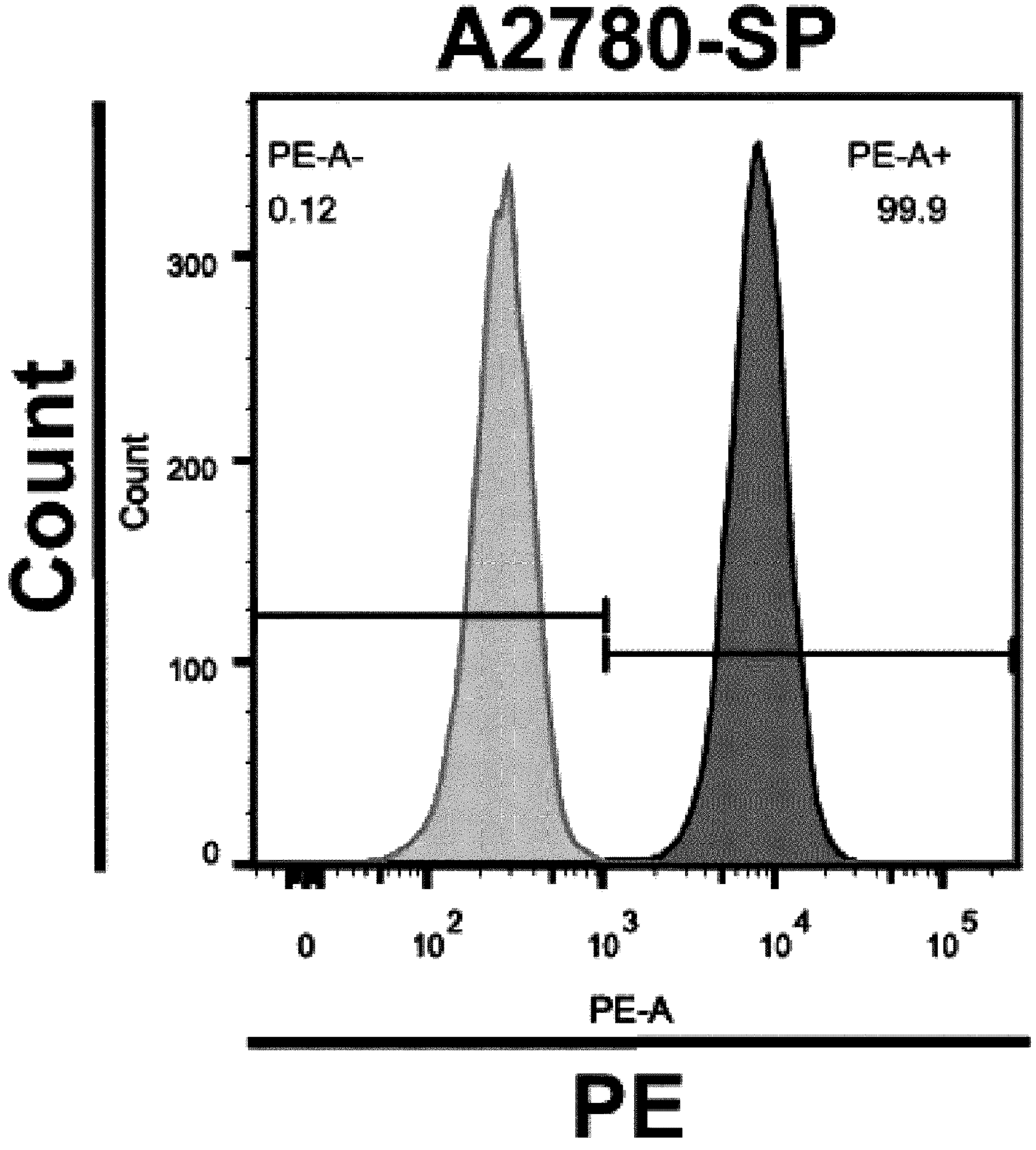

[Fig. 3]
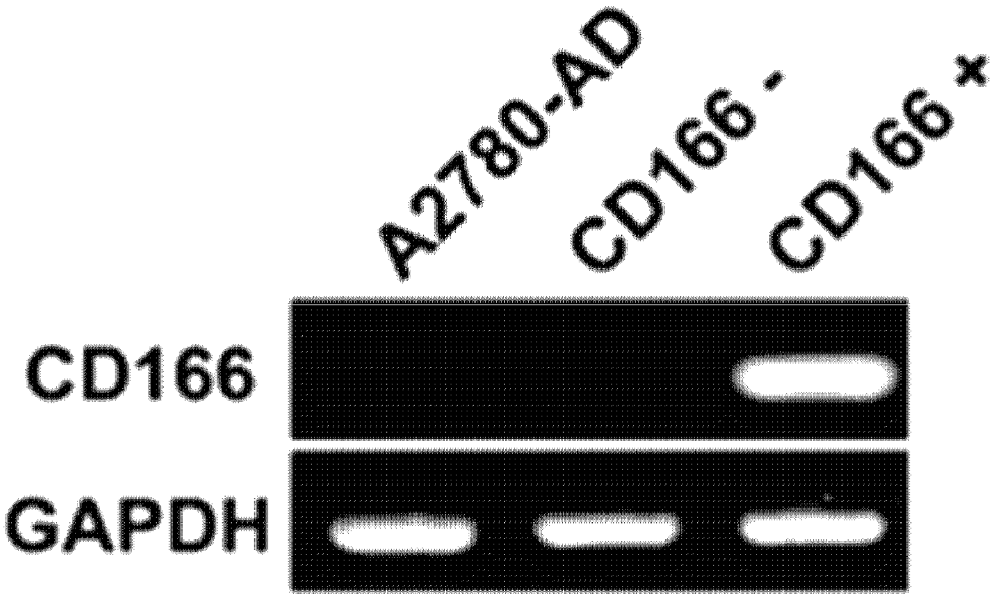

[Fig. 4]
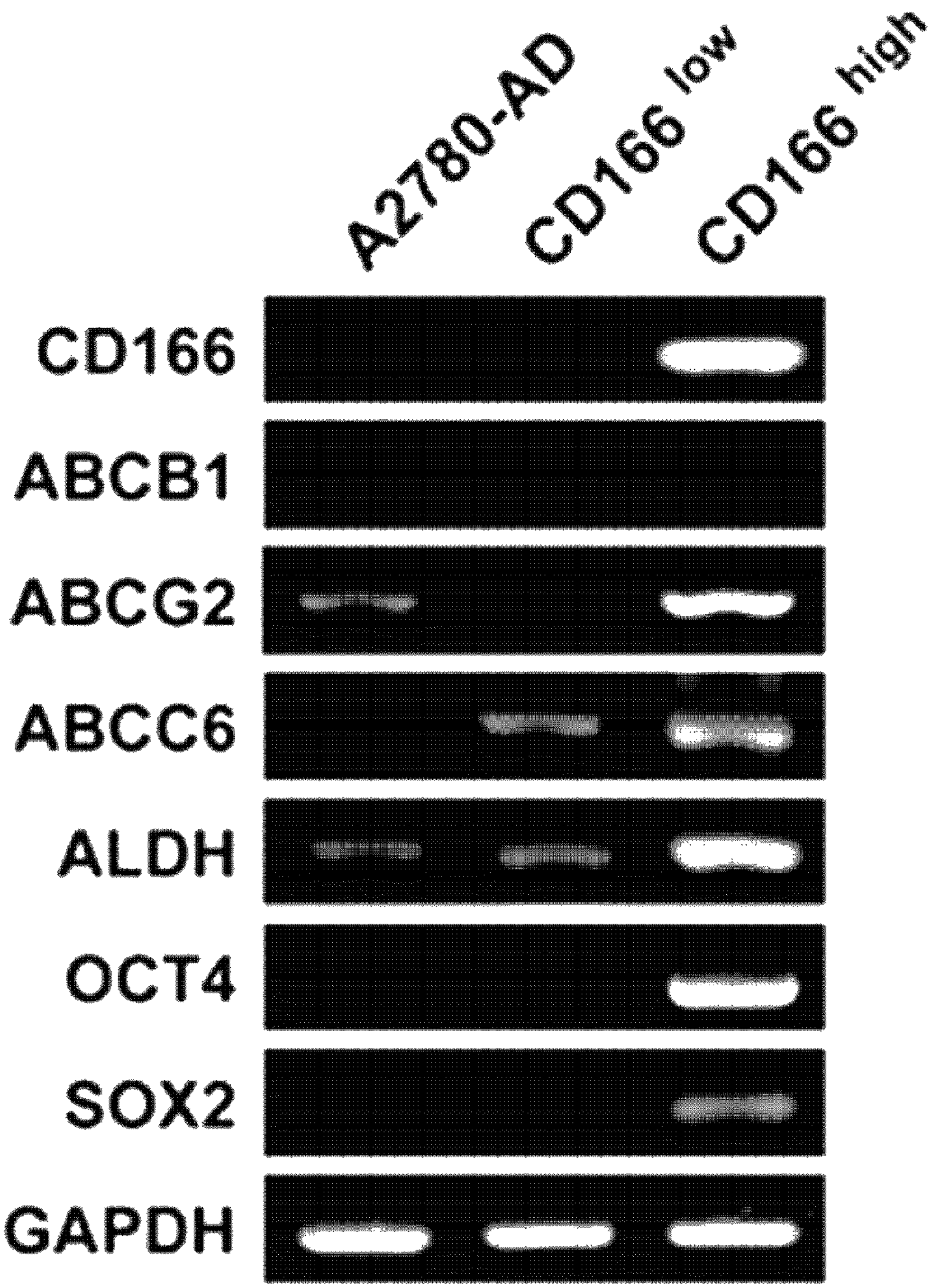

[Fig. 5]
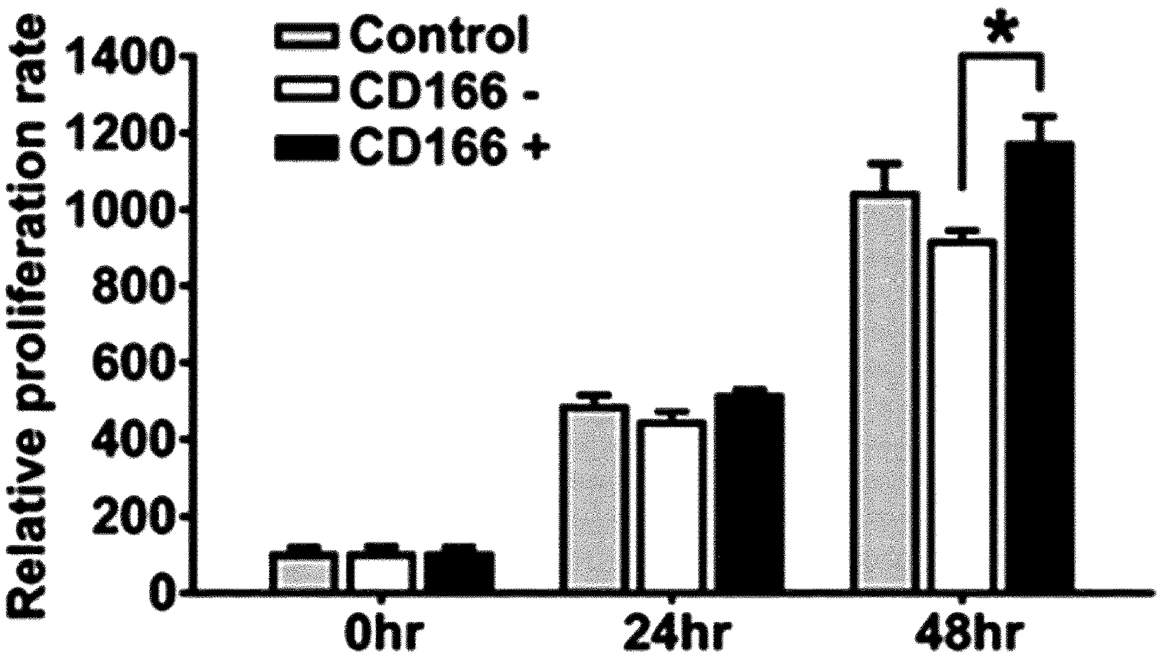
[Fig. 6]
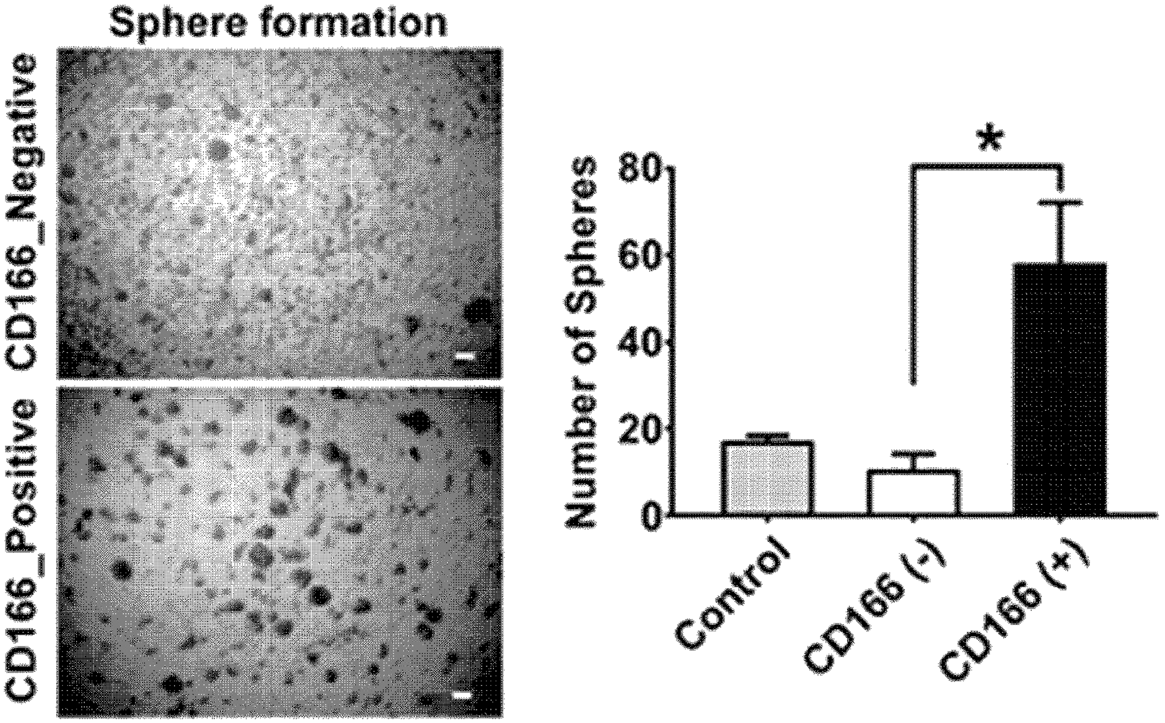

[Fig. 7]
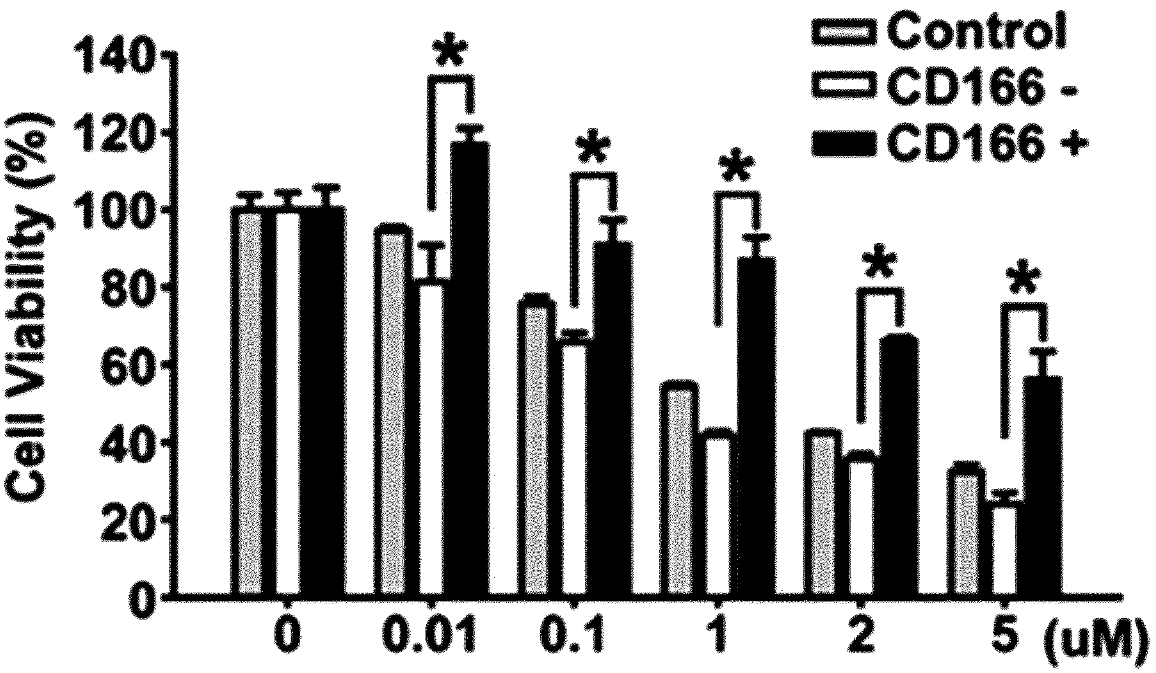

[Fig. 8]
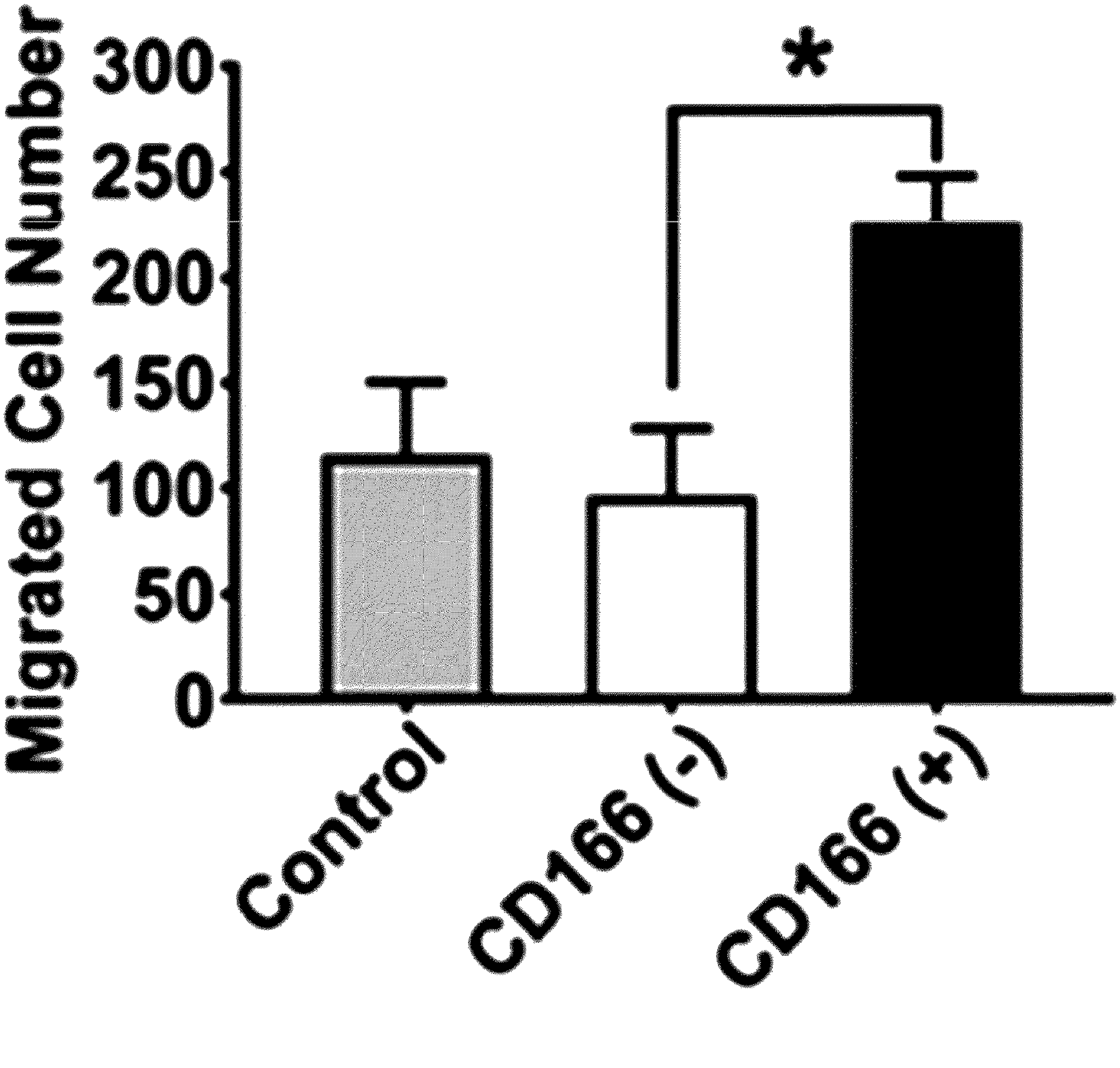

[Fig. 9]
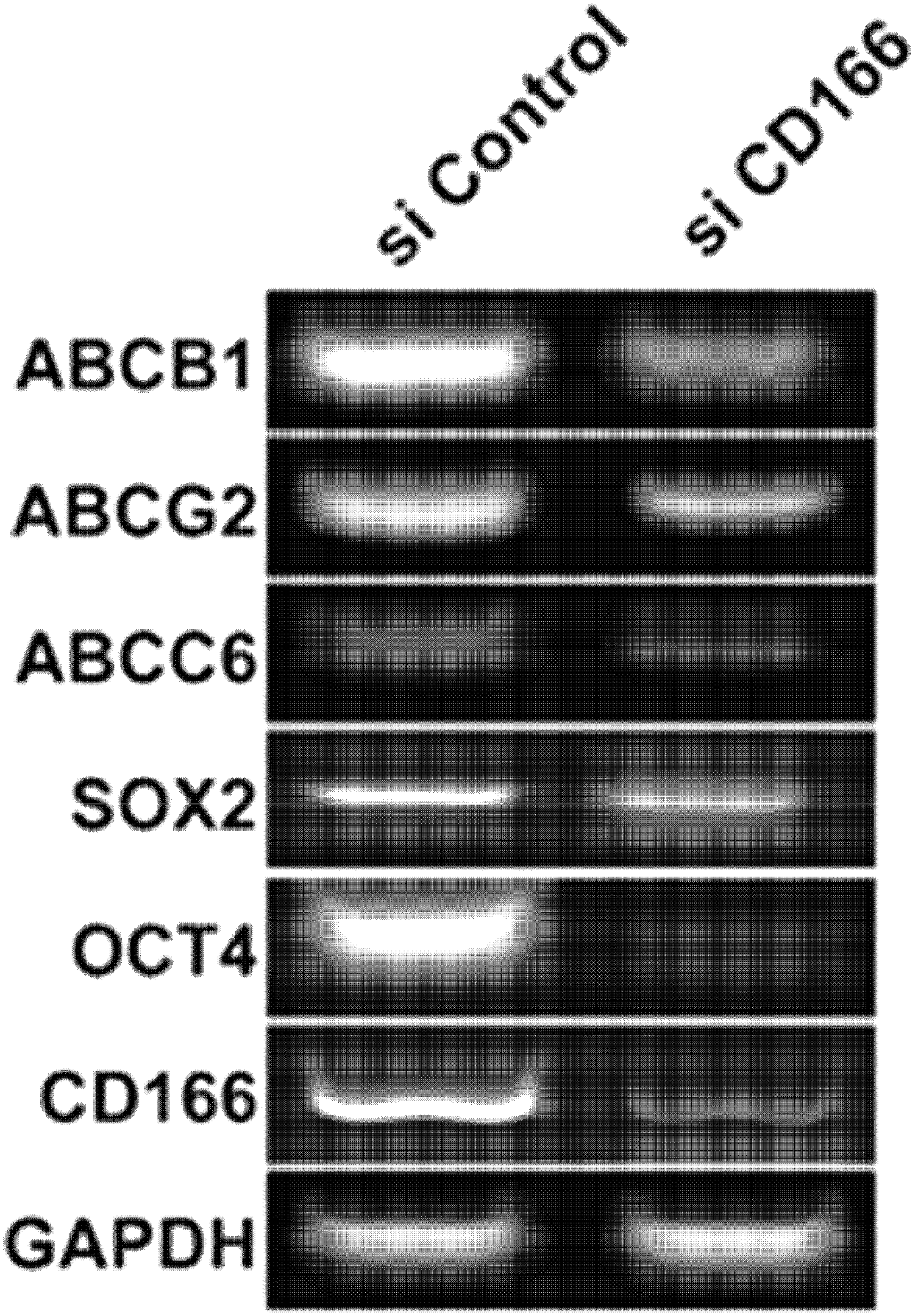

[Fig. 10]
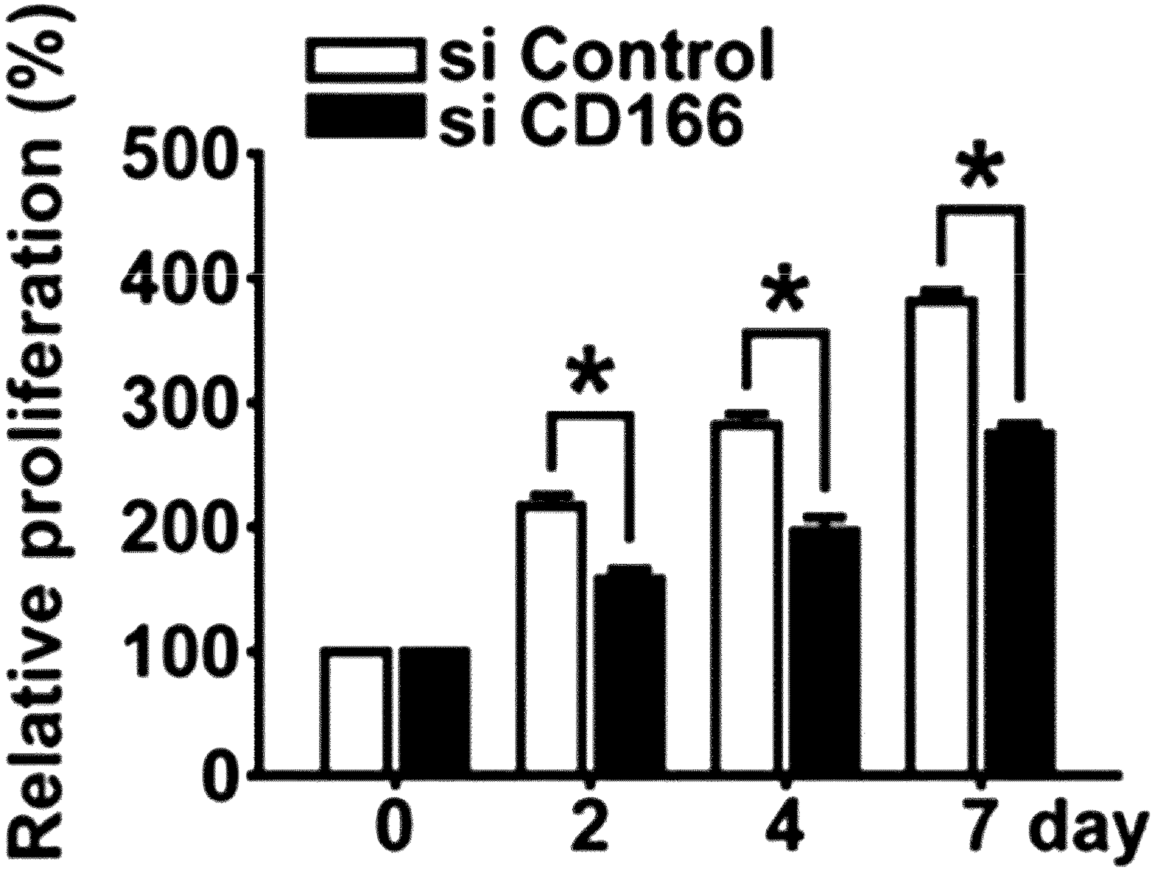

[Fig. 11]
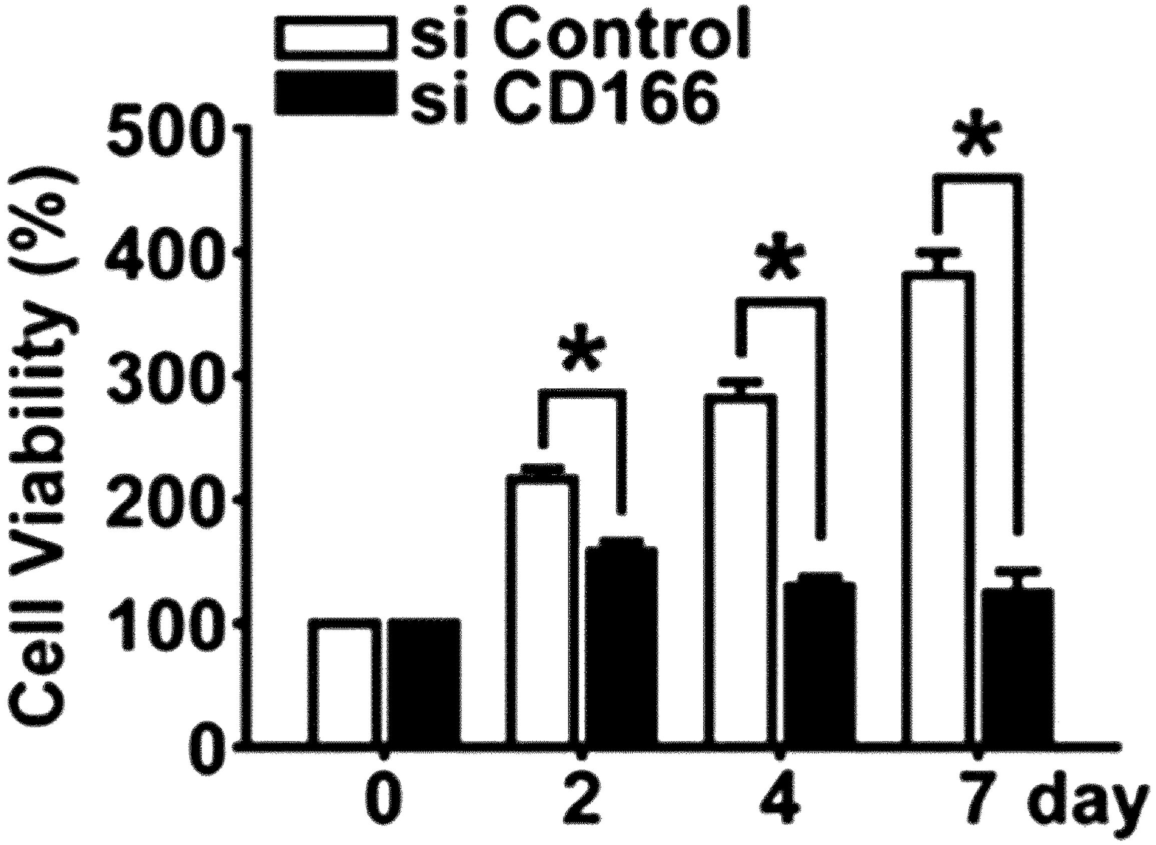
[Fig. 12]
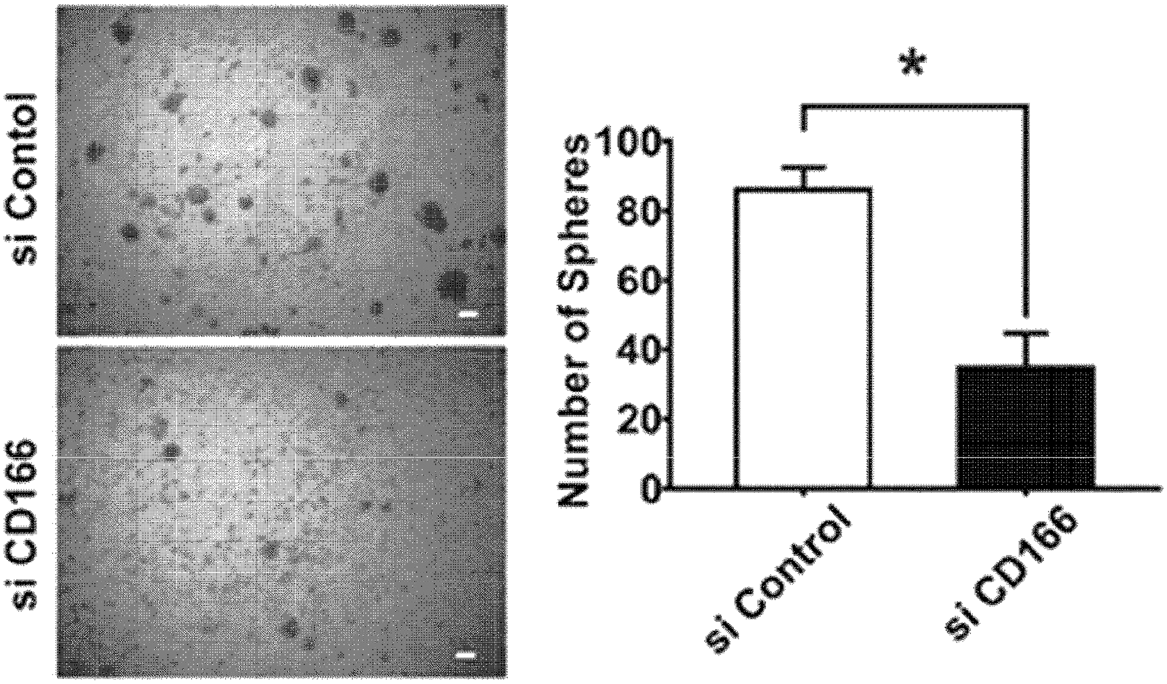

[Fig. 13]
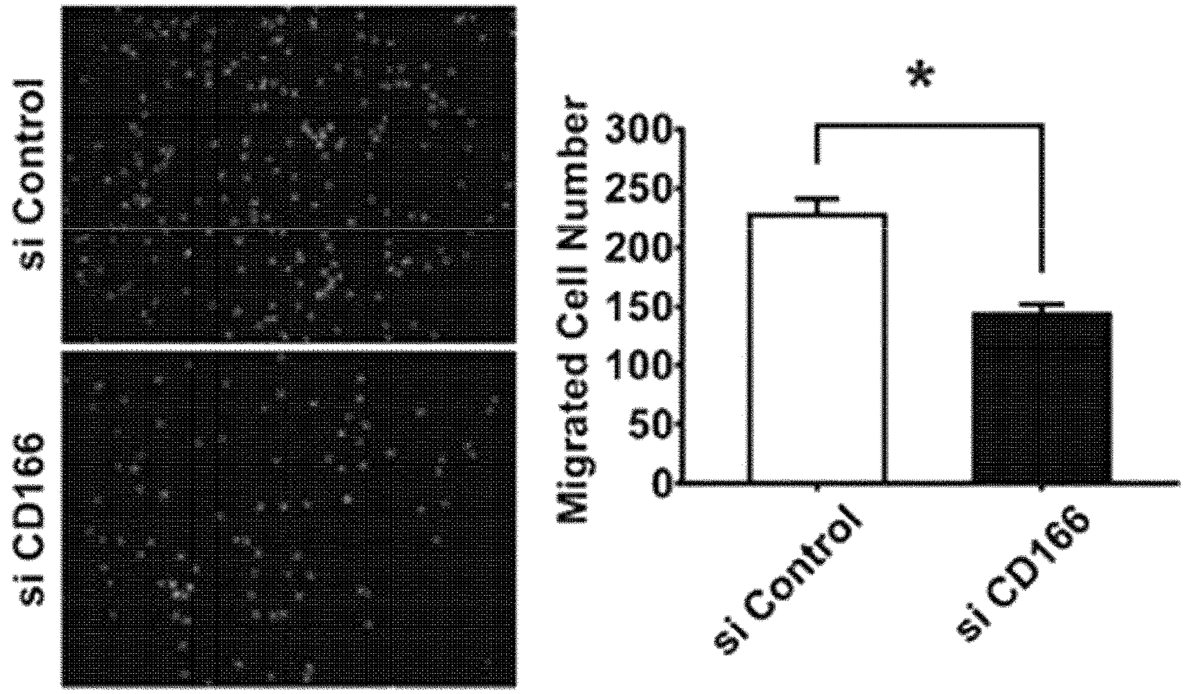

[Fig. 14]
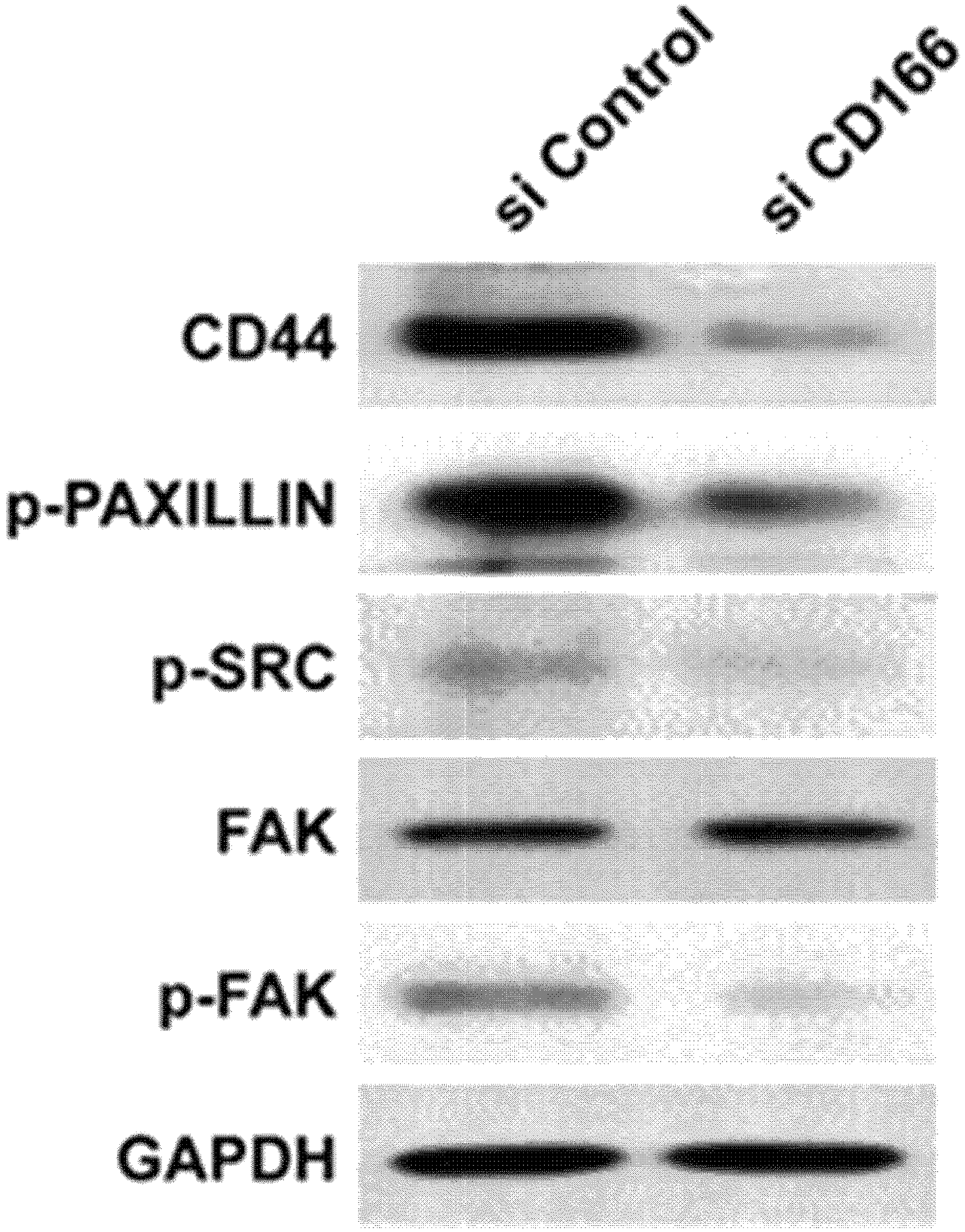

[Fig. 15]
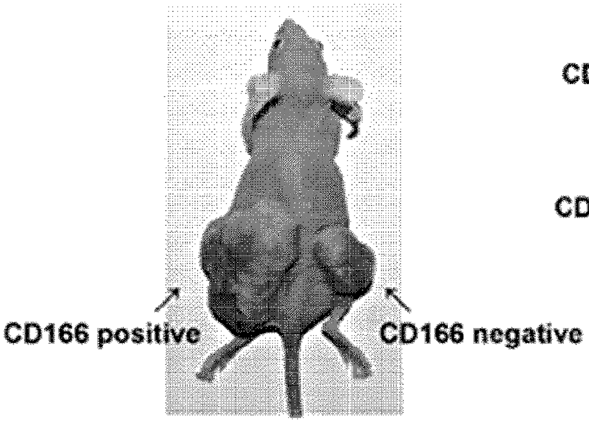
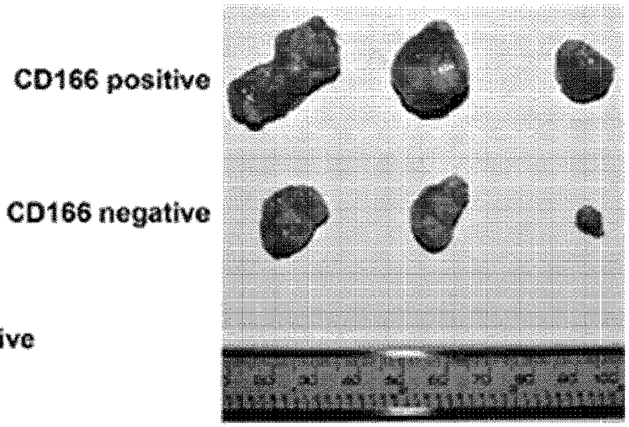
[Fig. 16]
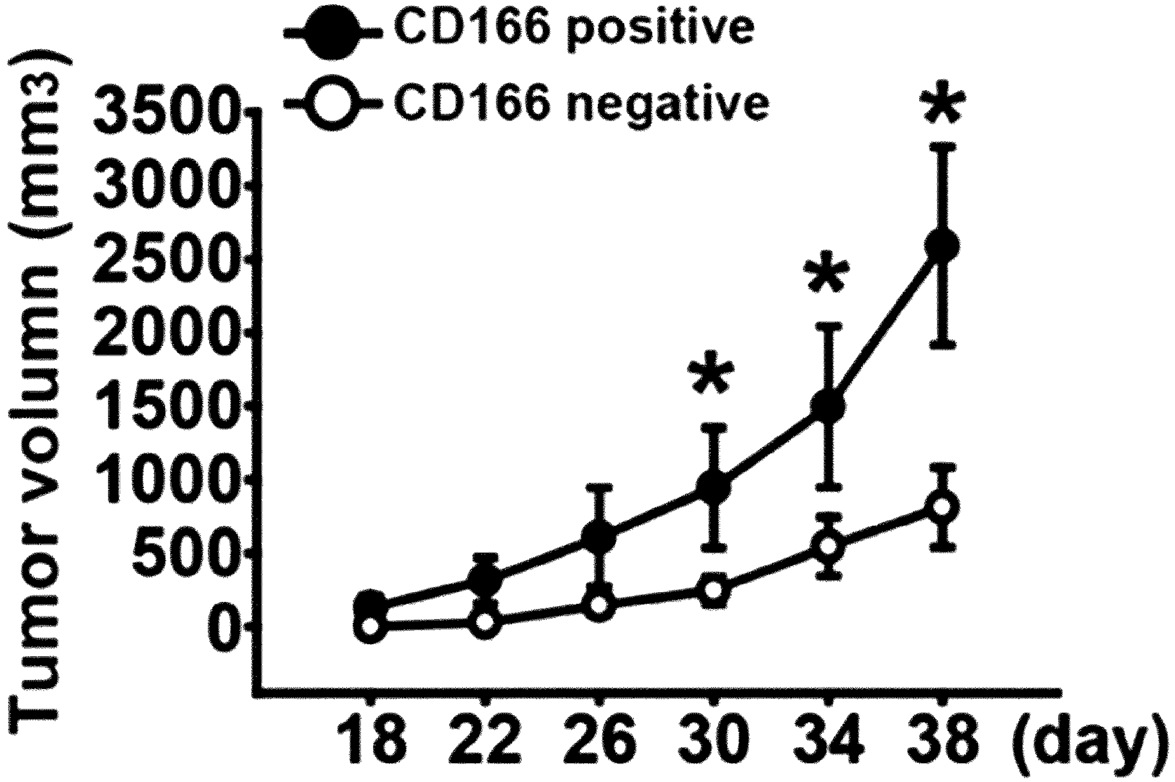

[Fig. 17]
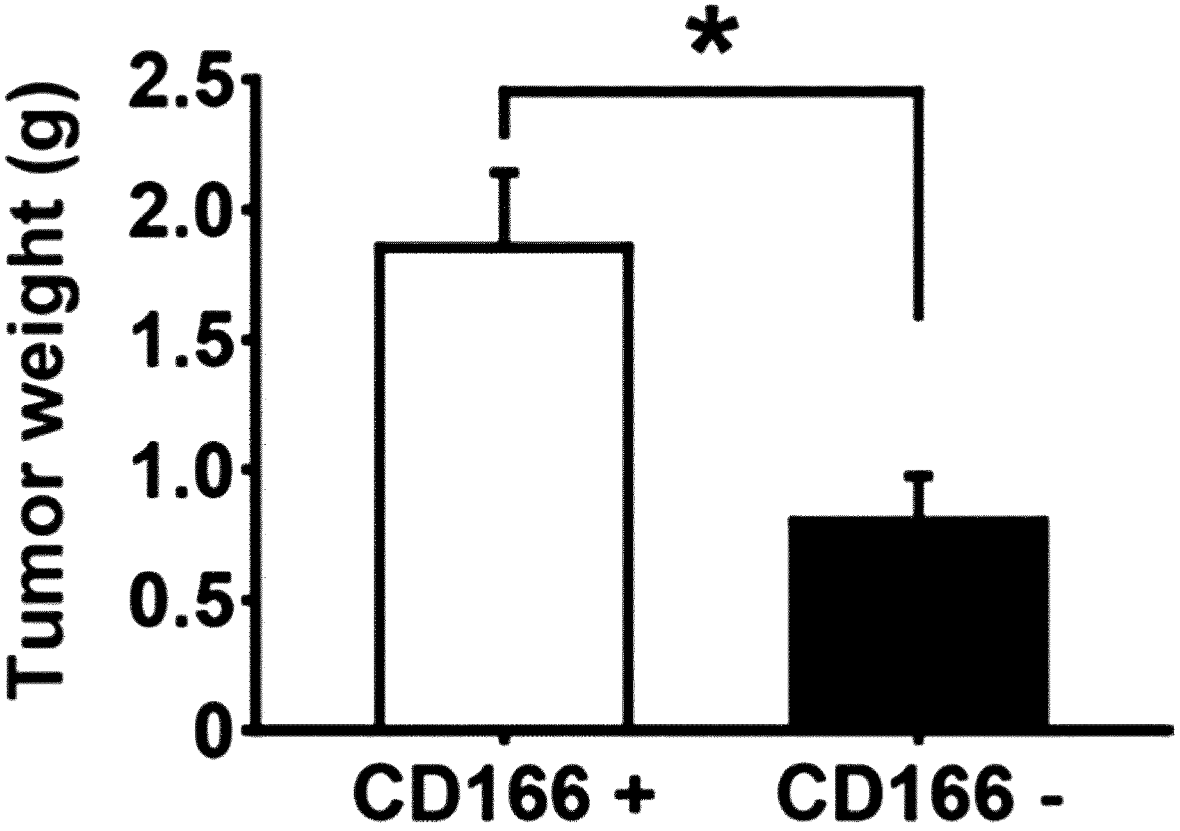

[Fig. 20]
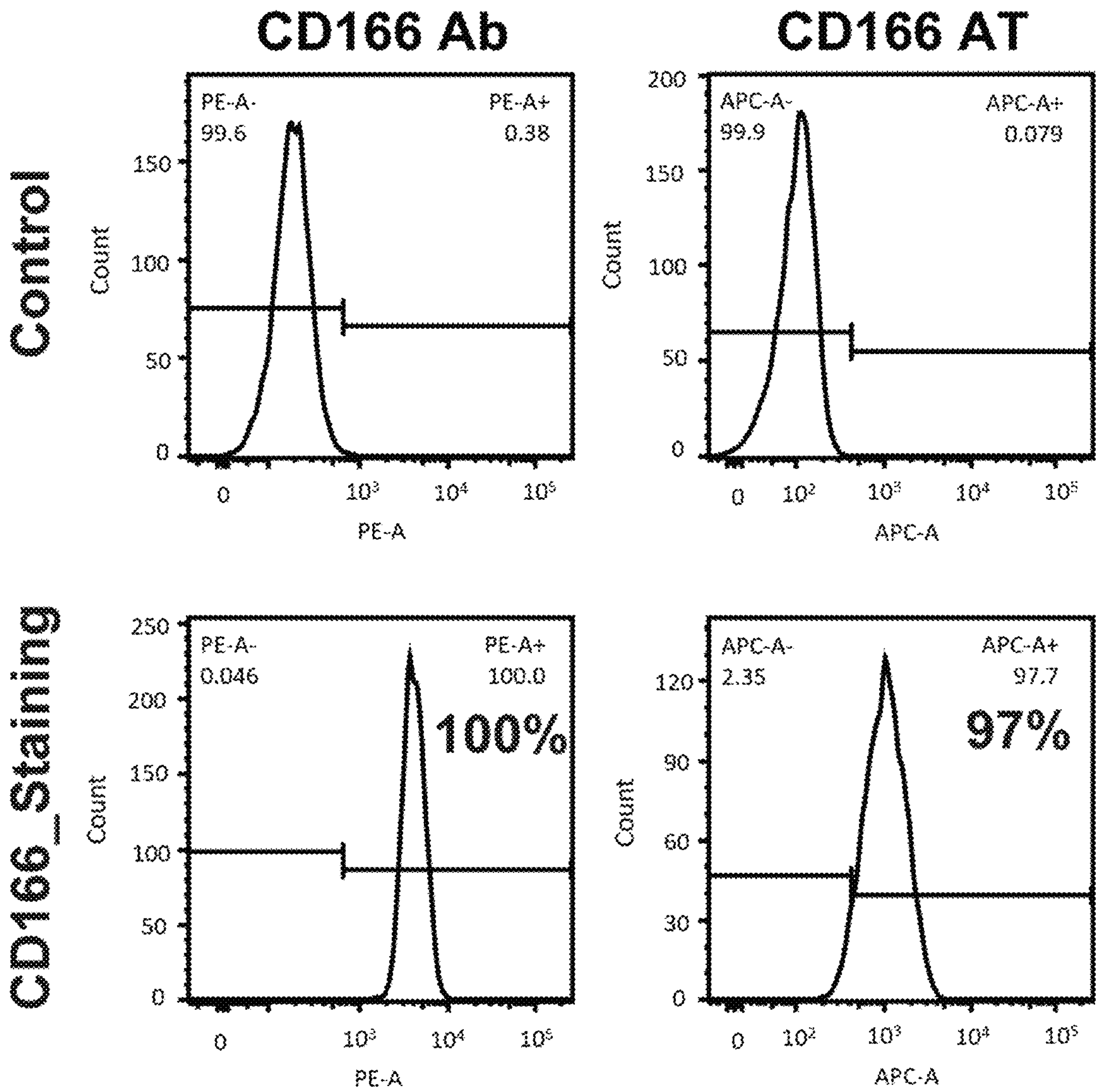
[Fig. 21]
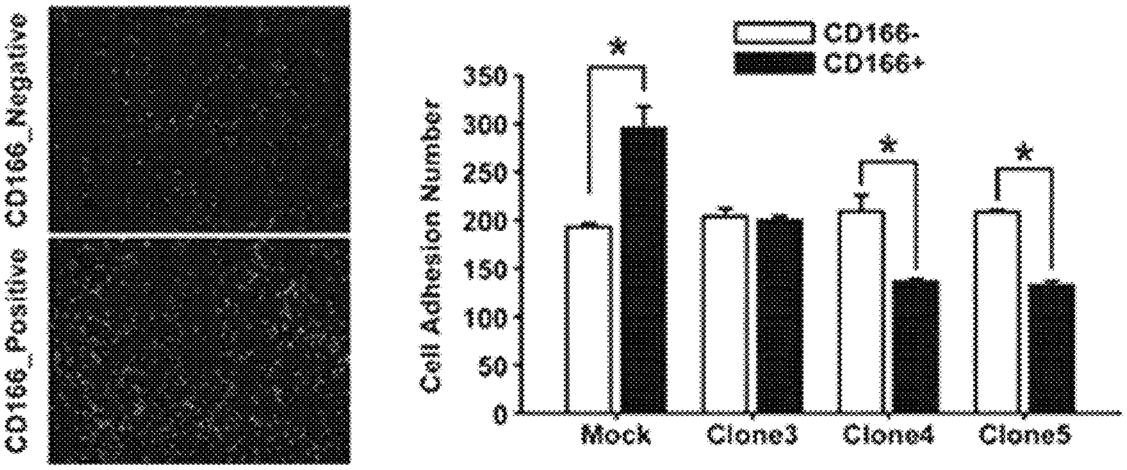

[Fig. 22]
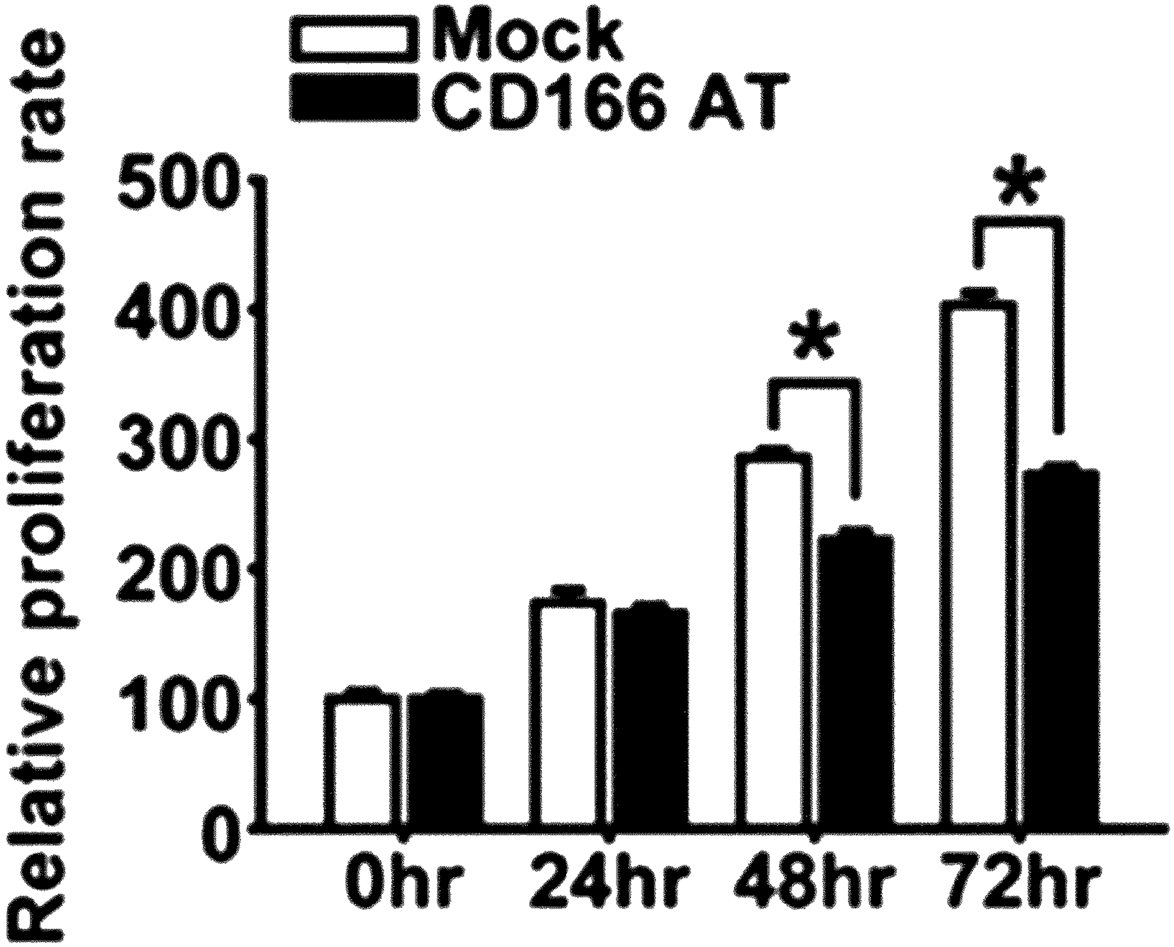

[Fig. 23]
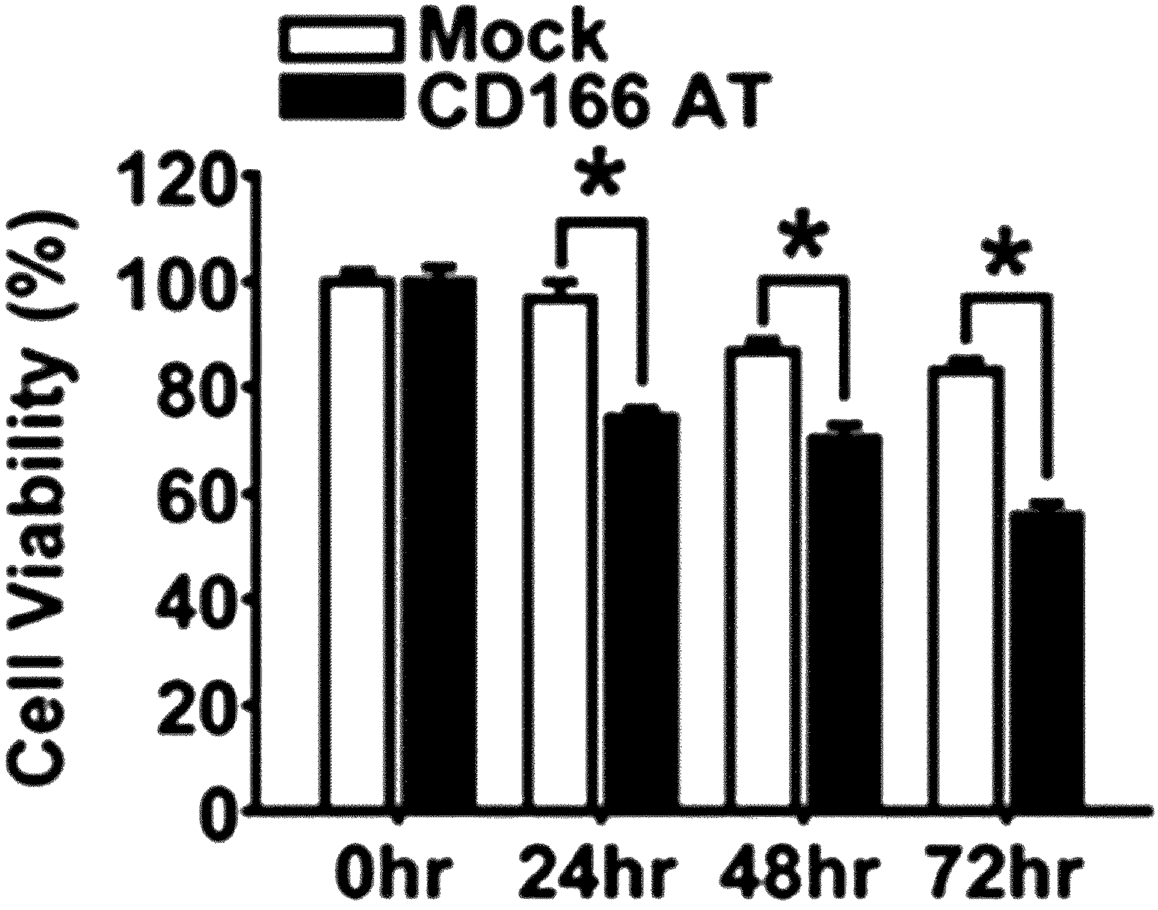

[Fig. 24]
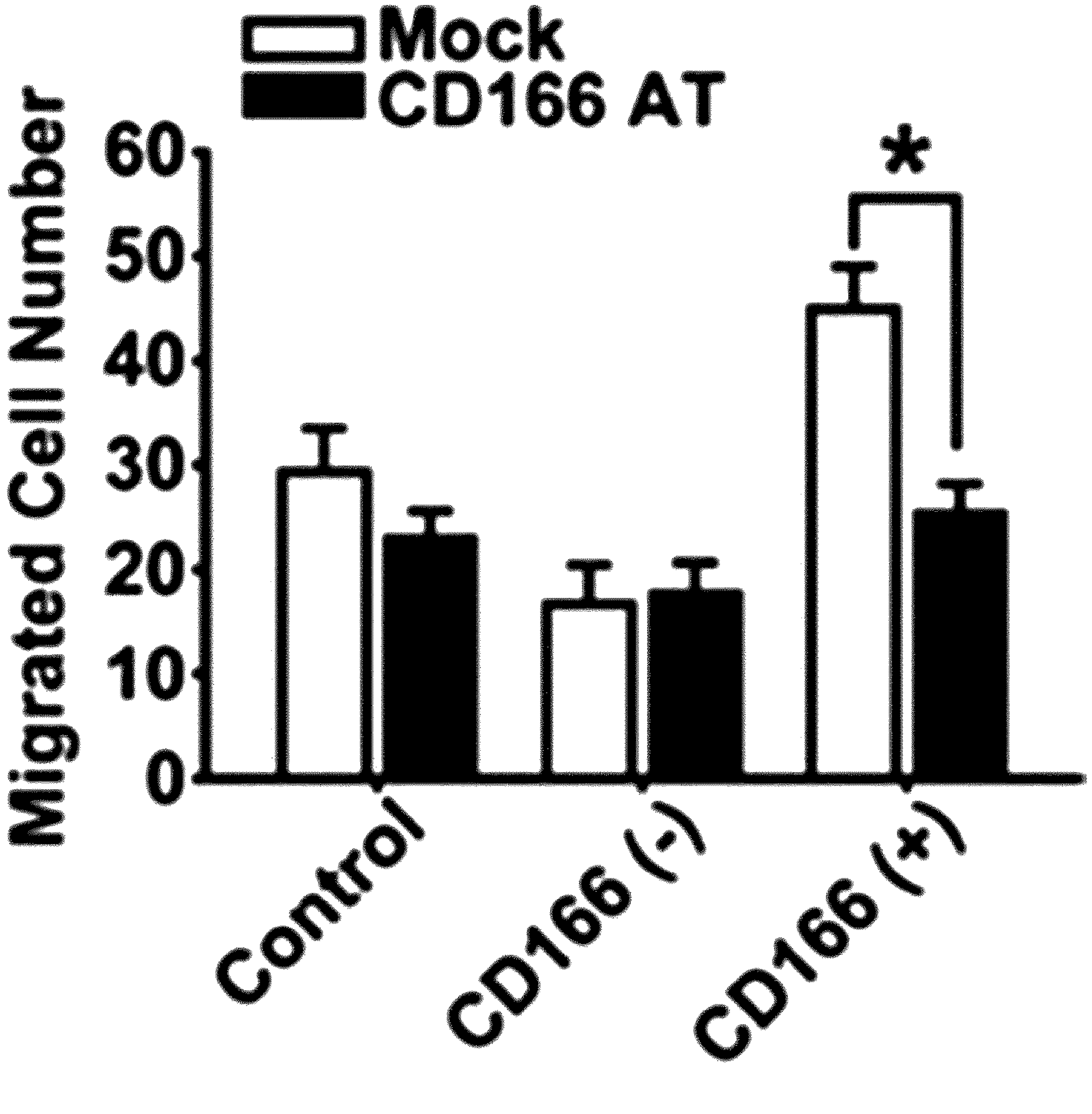

[Fig. 25]
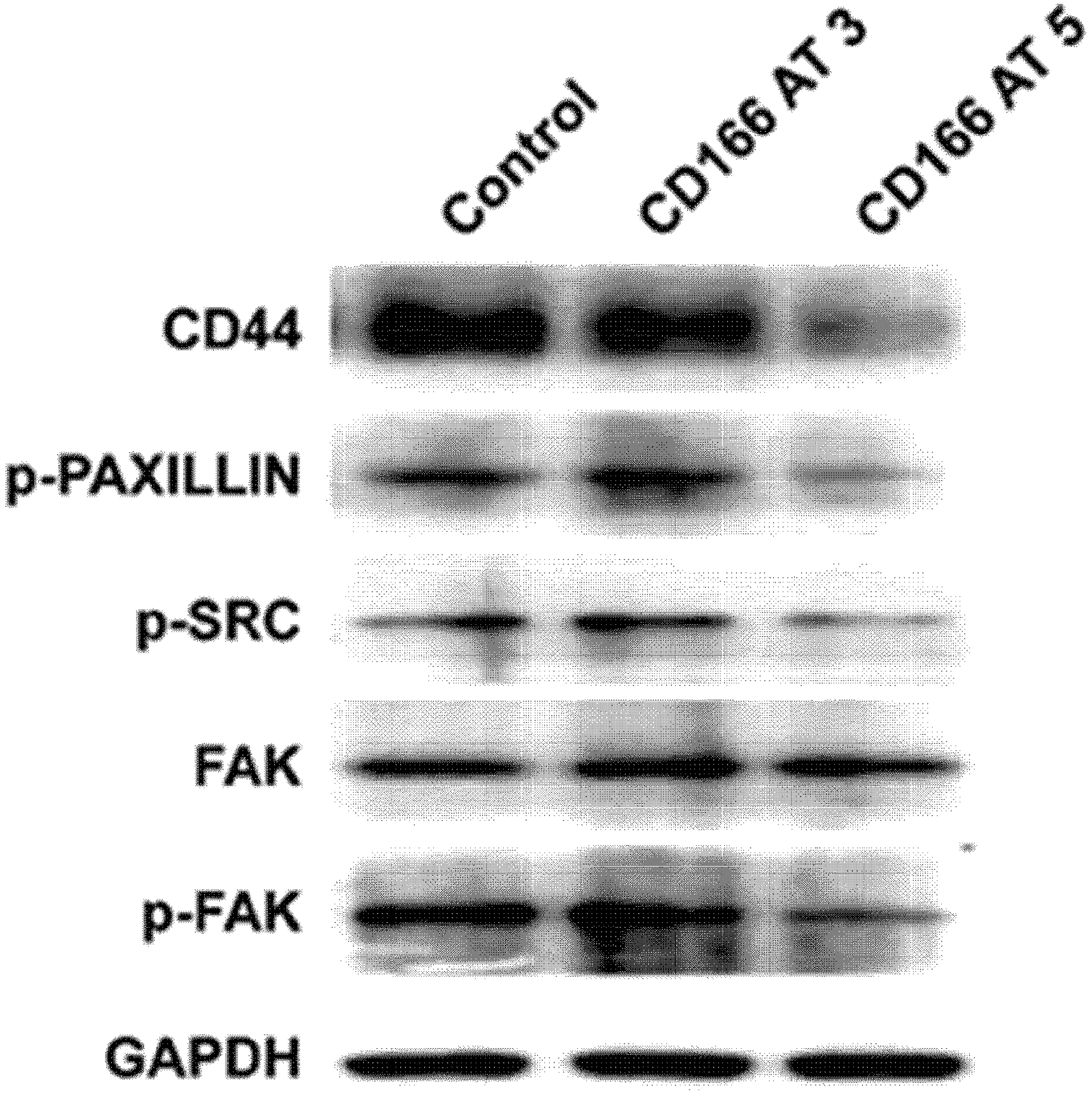

[Fig. 26]
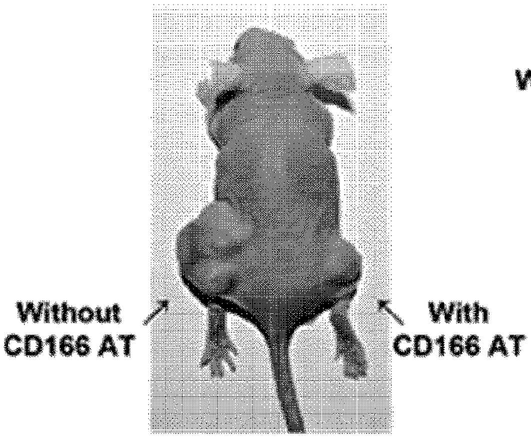
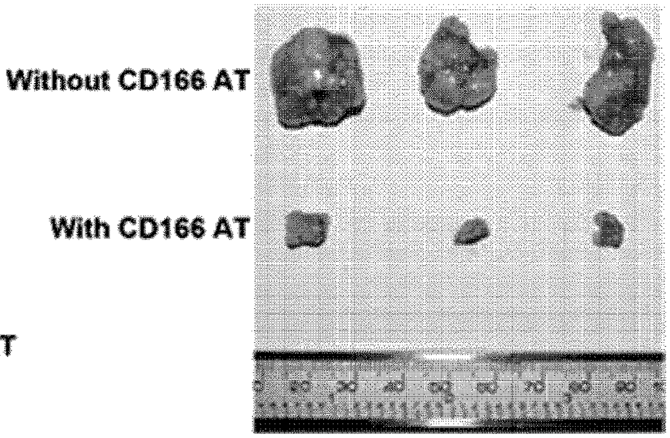
[Fig. 27]
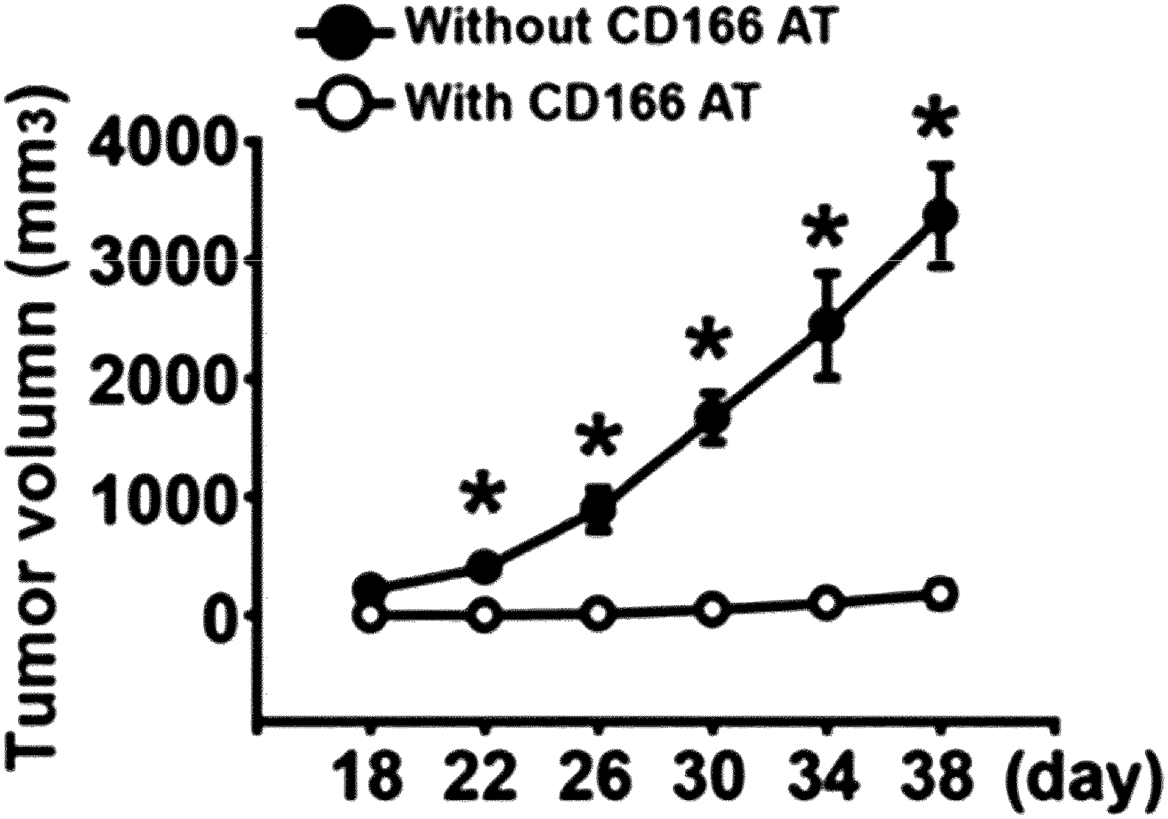

[Fig. 28]
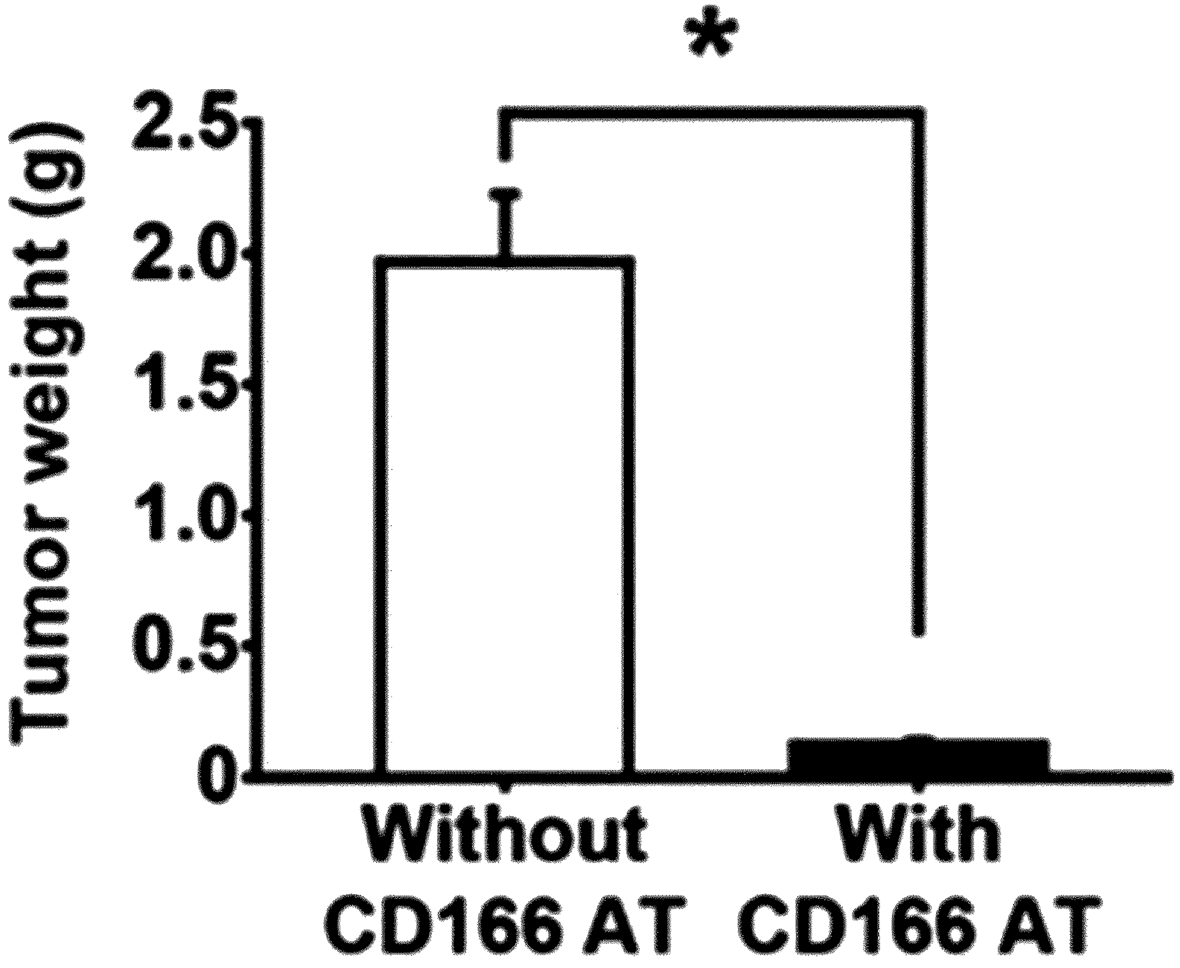

[Fig. 29]
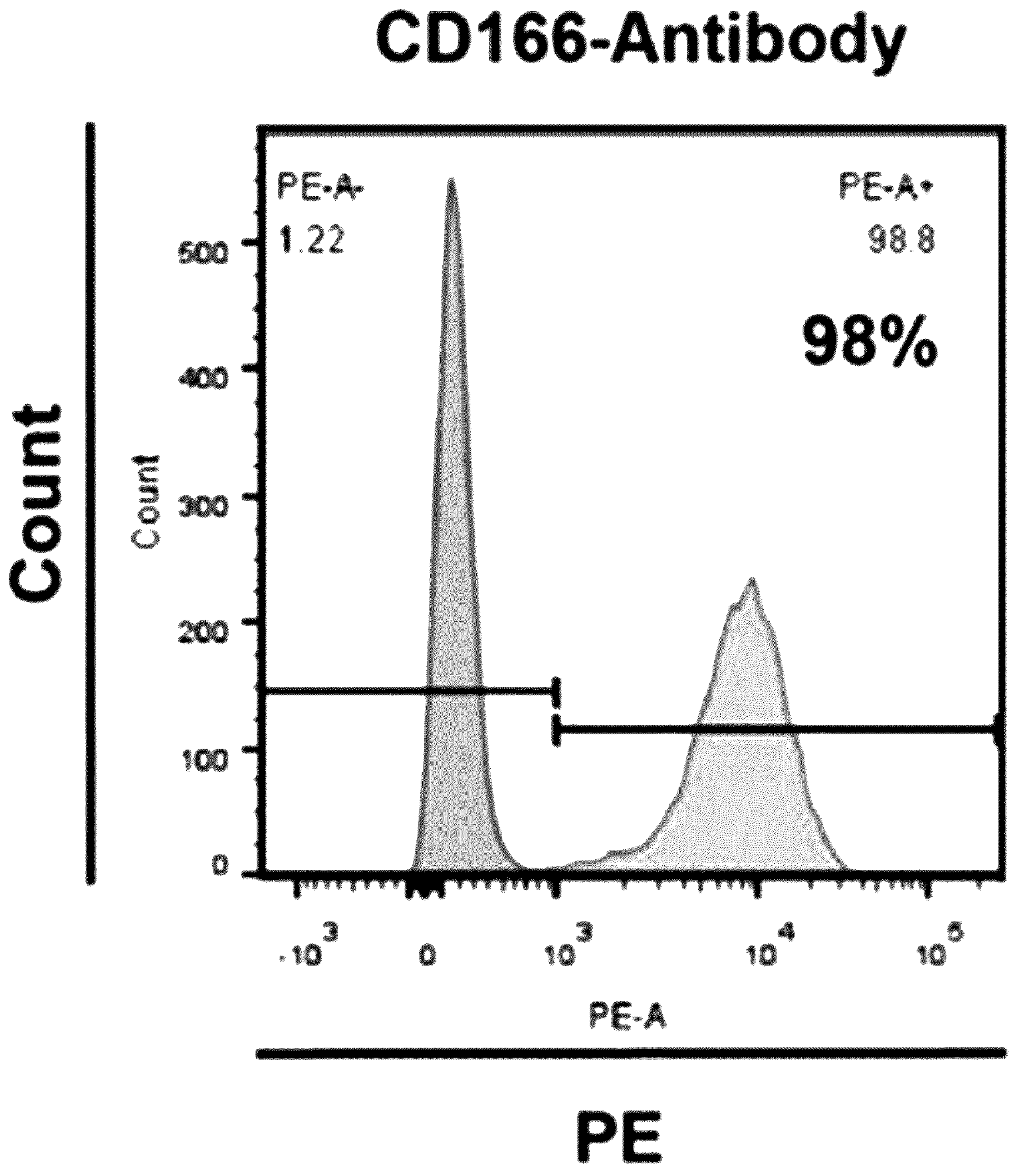

[Fig. 30]
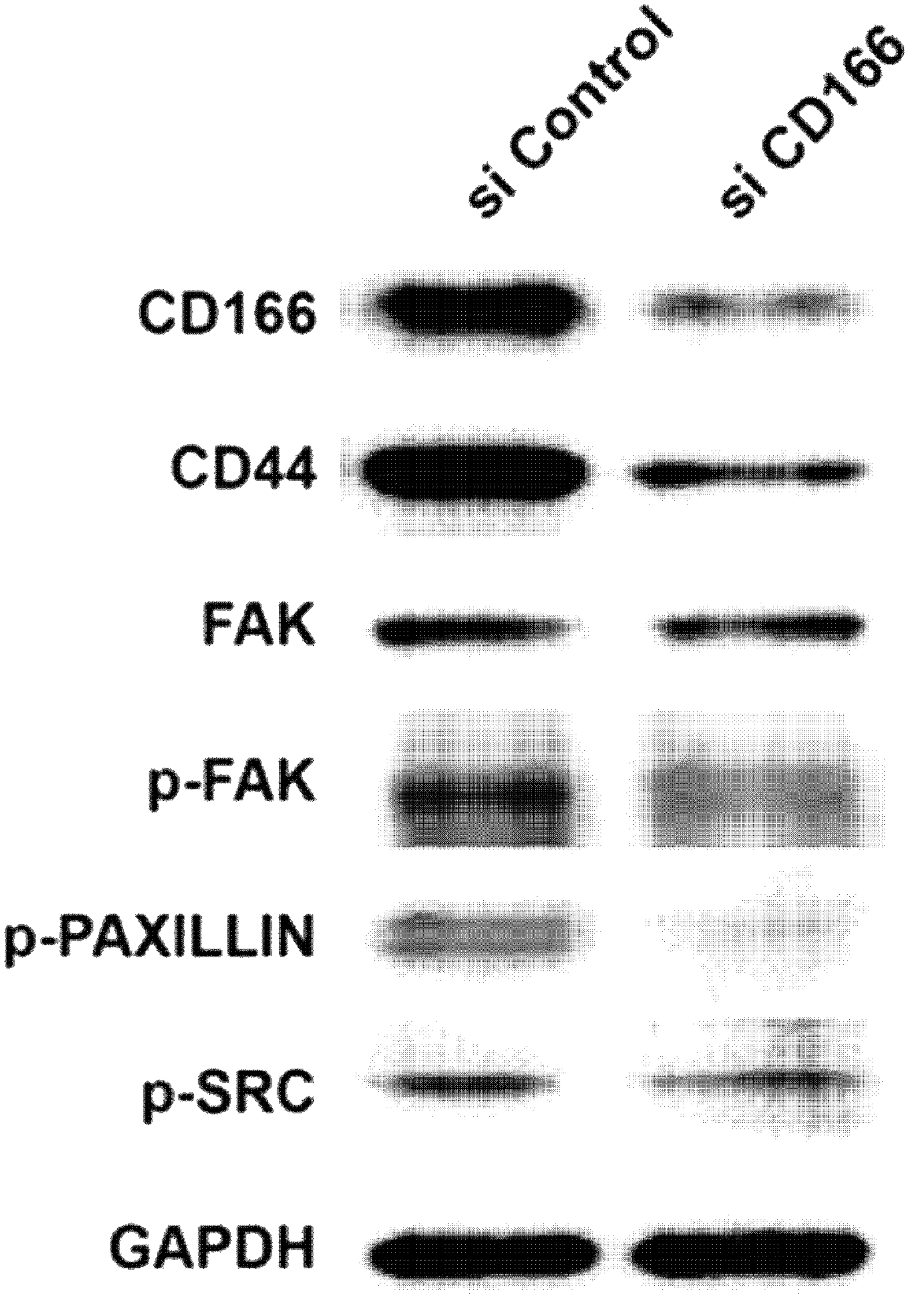

[Fig. 31]
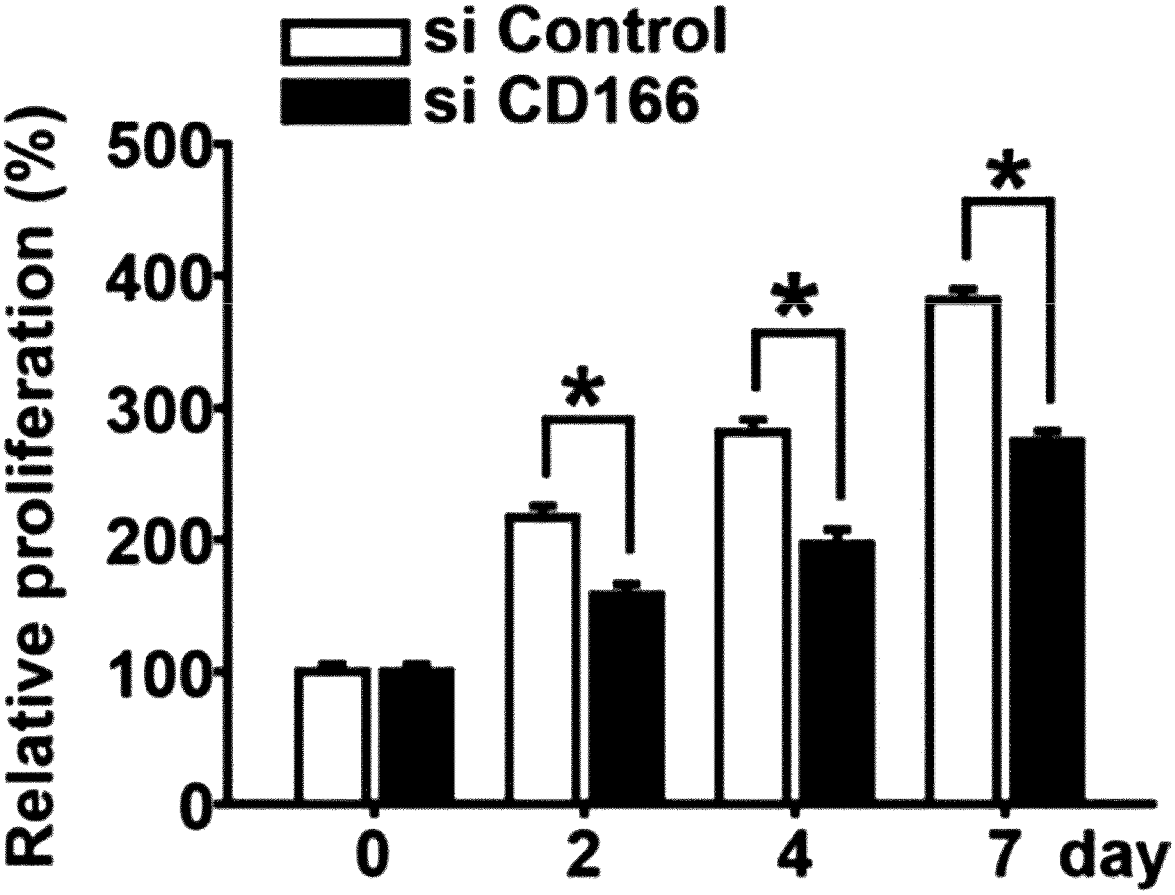

[Fig. 32]
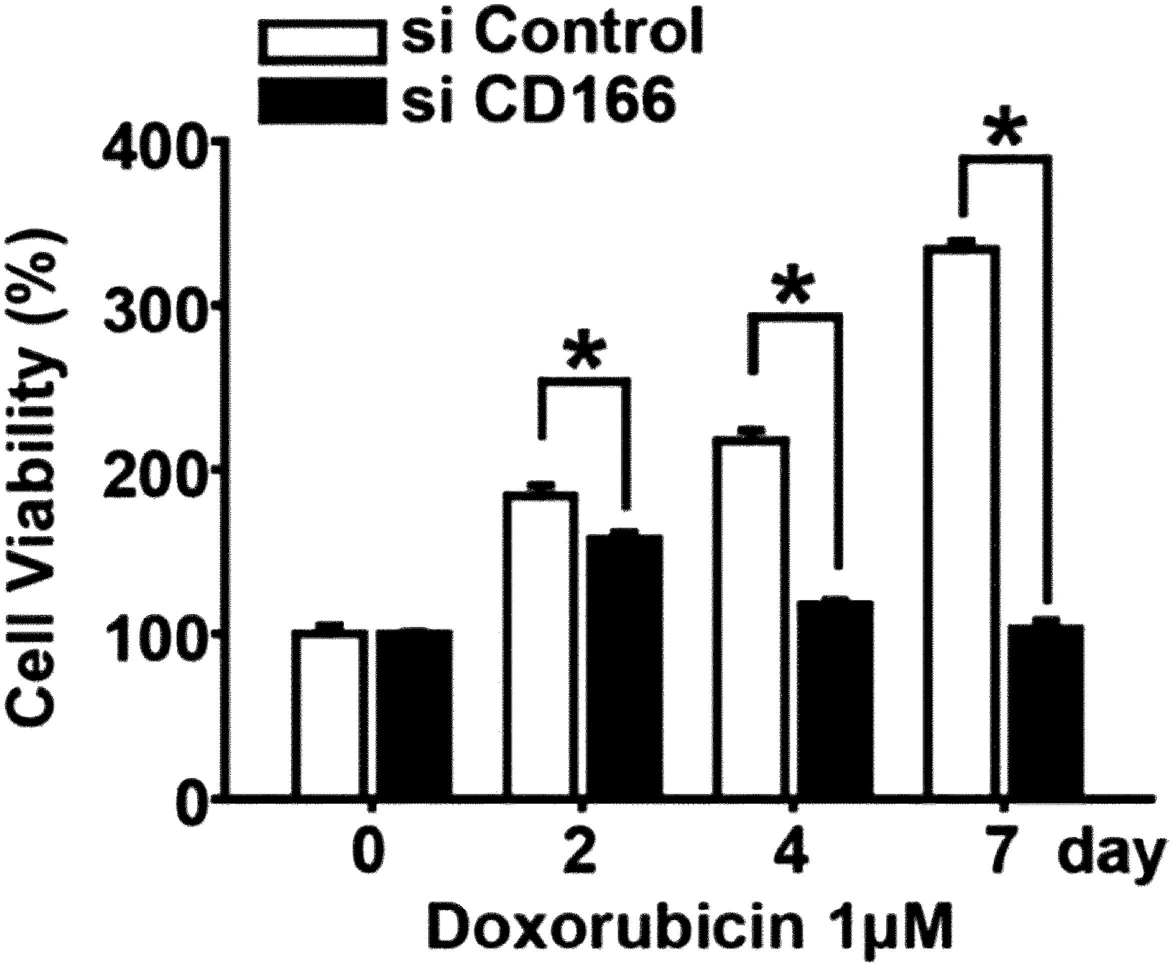

[Fig. 33]
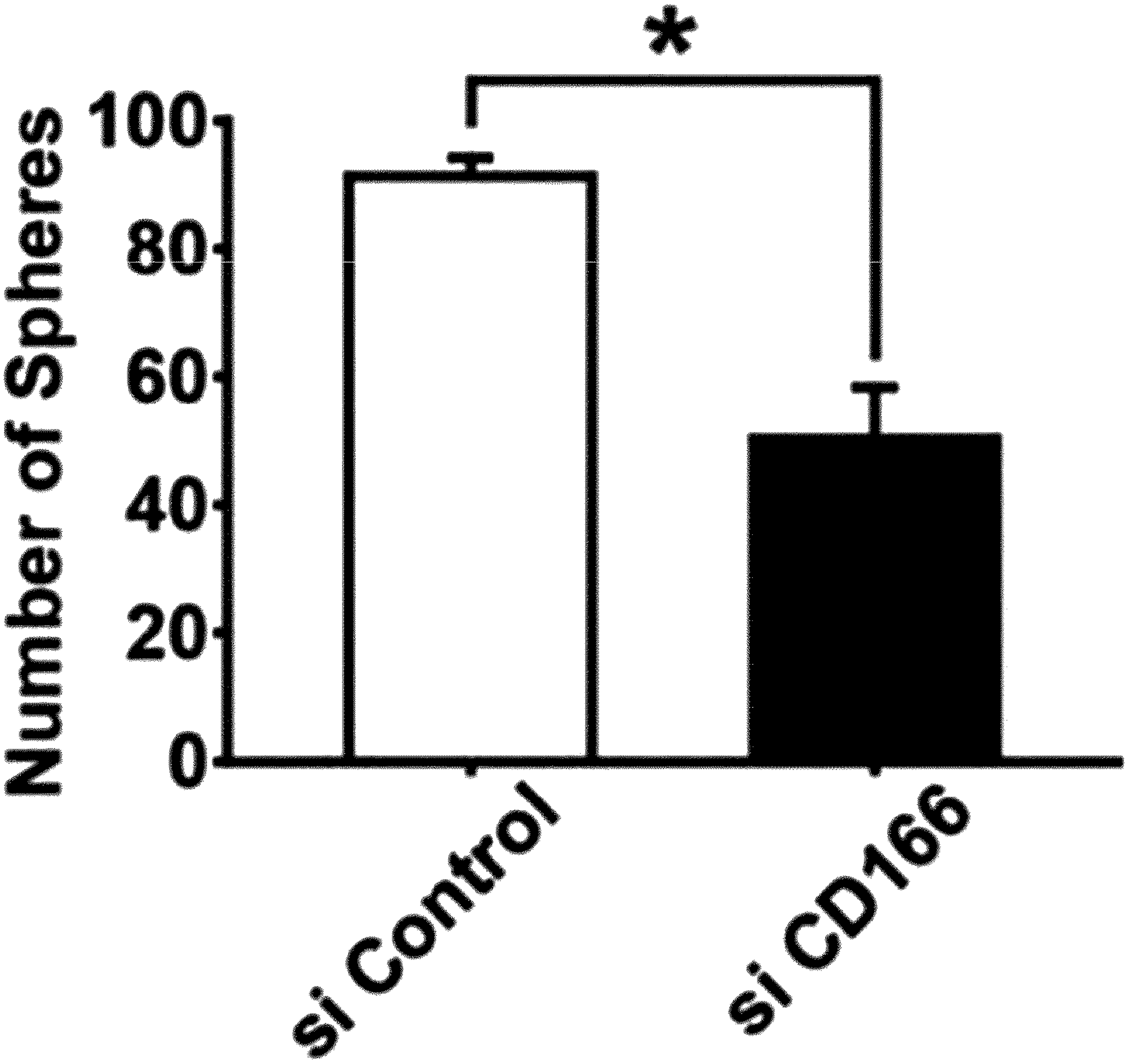

[Fig. 34]
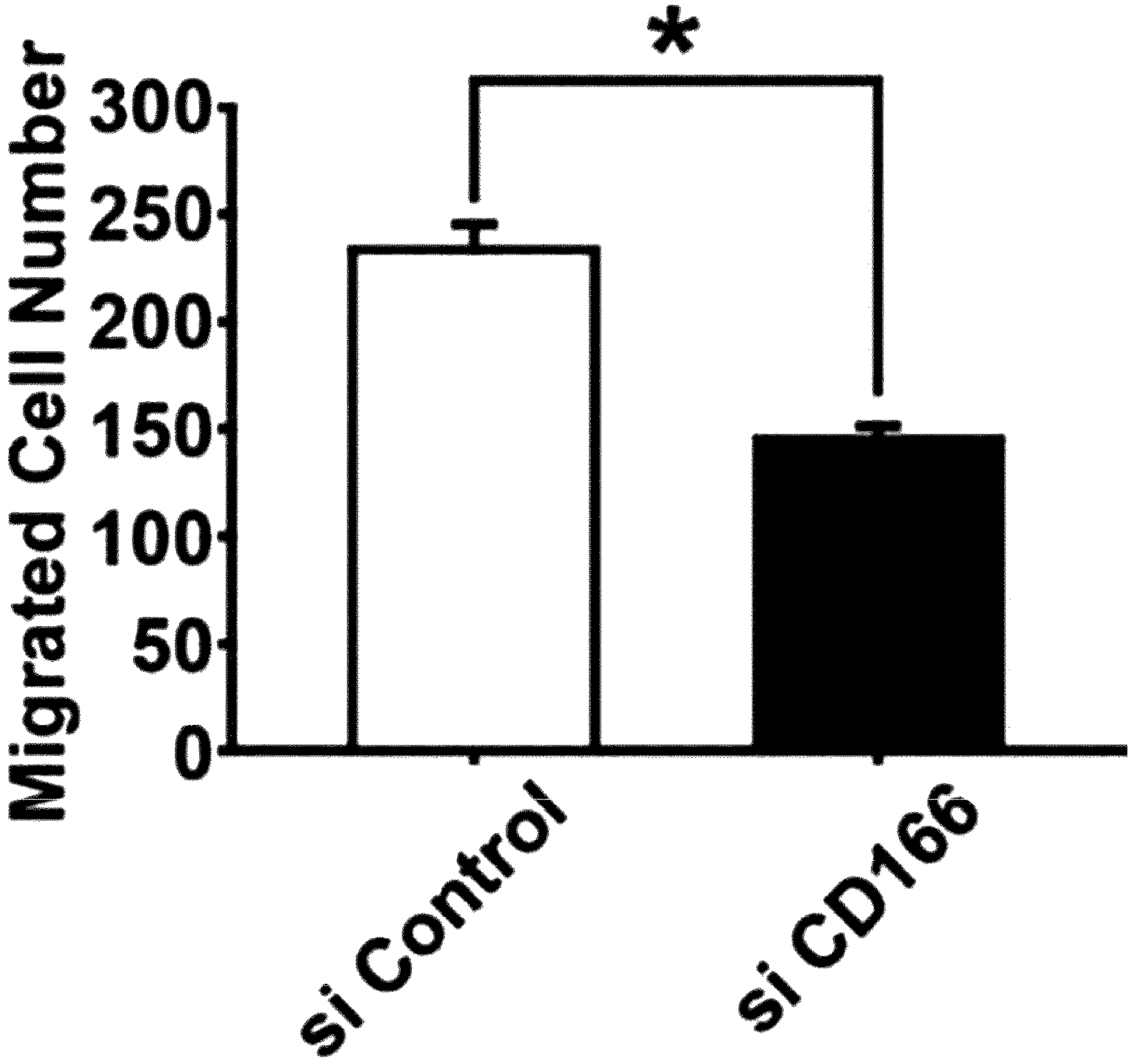

[Fig. 35]
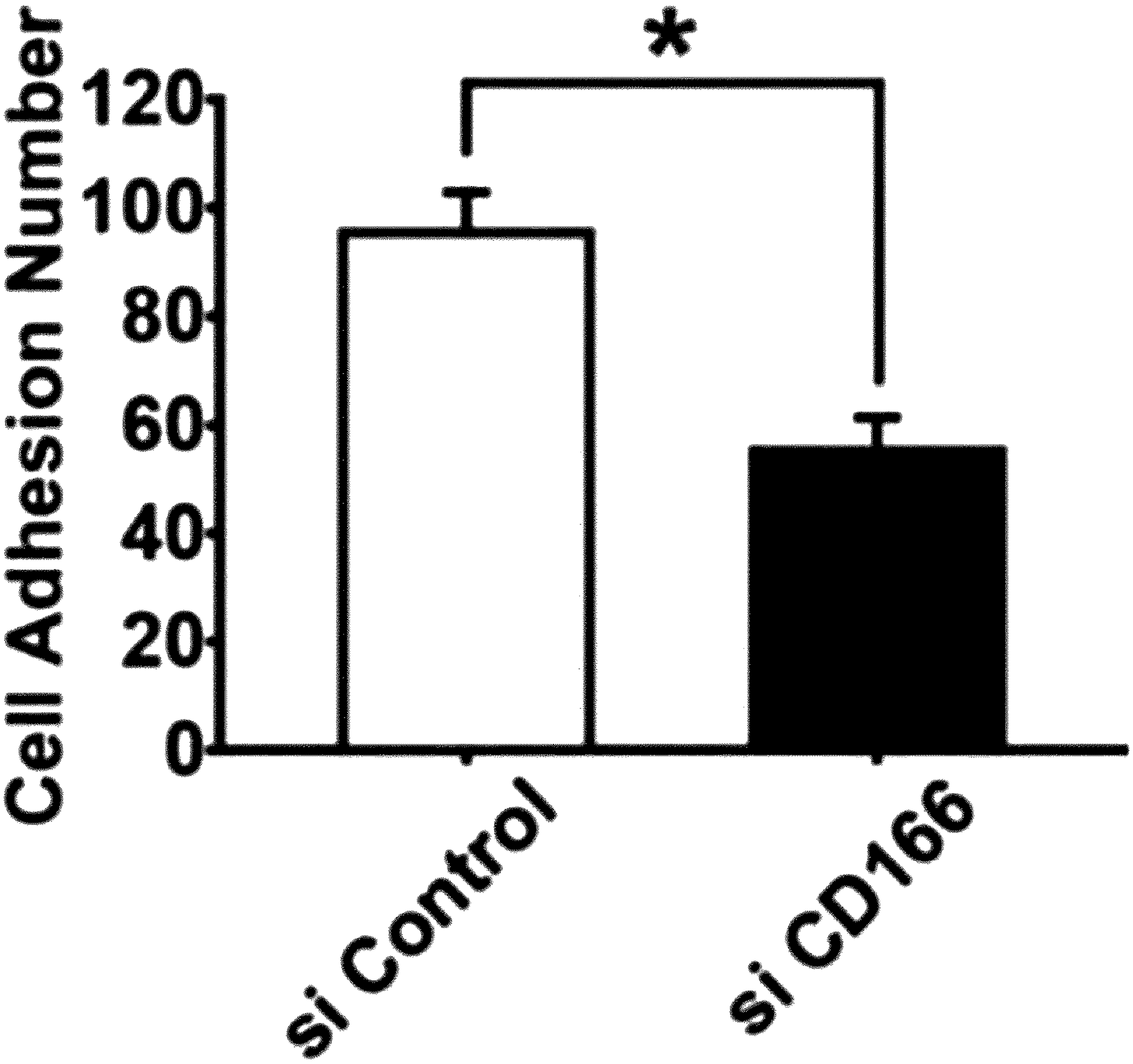
[Fig. 36]
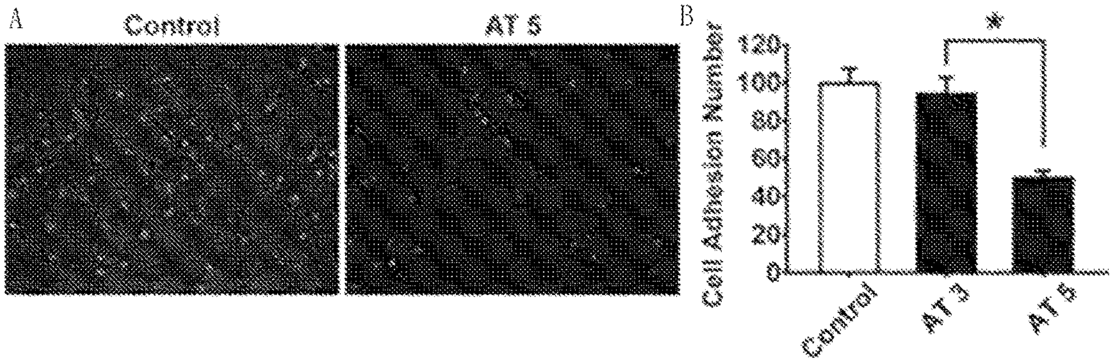

[Fig. 37]
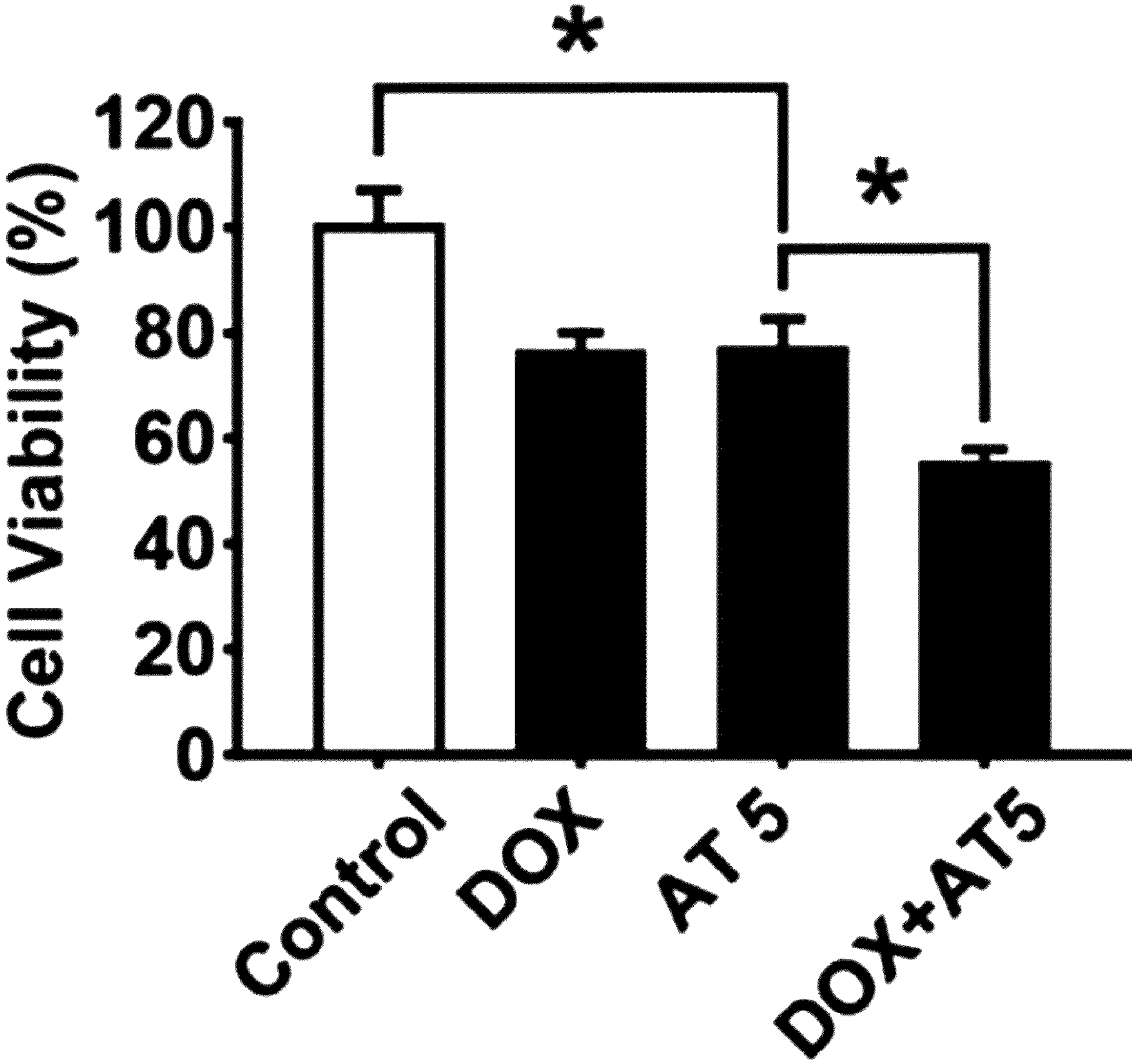

[Fig. 38]
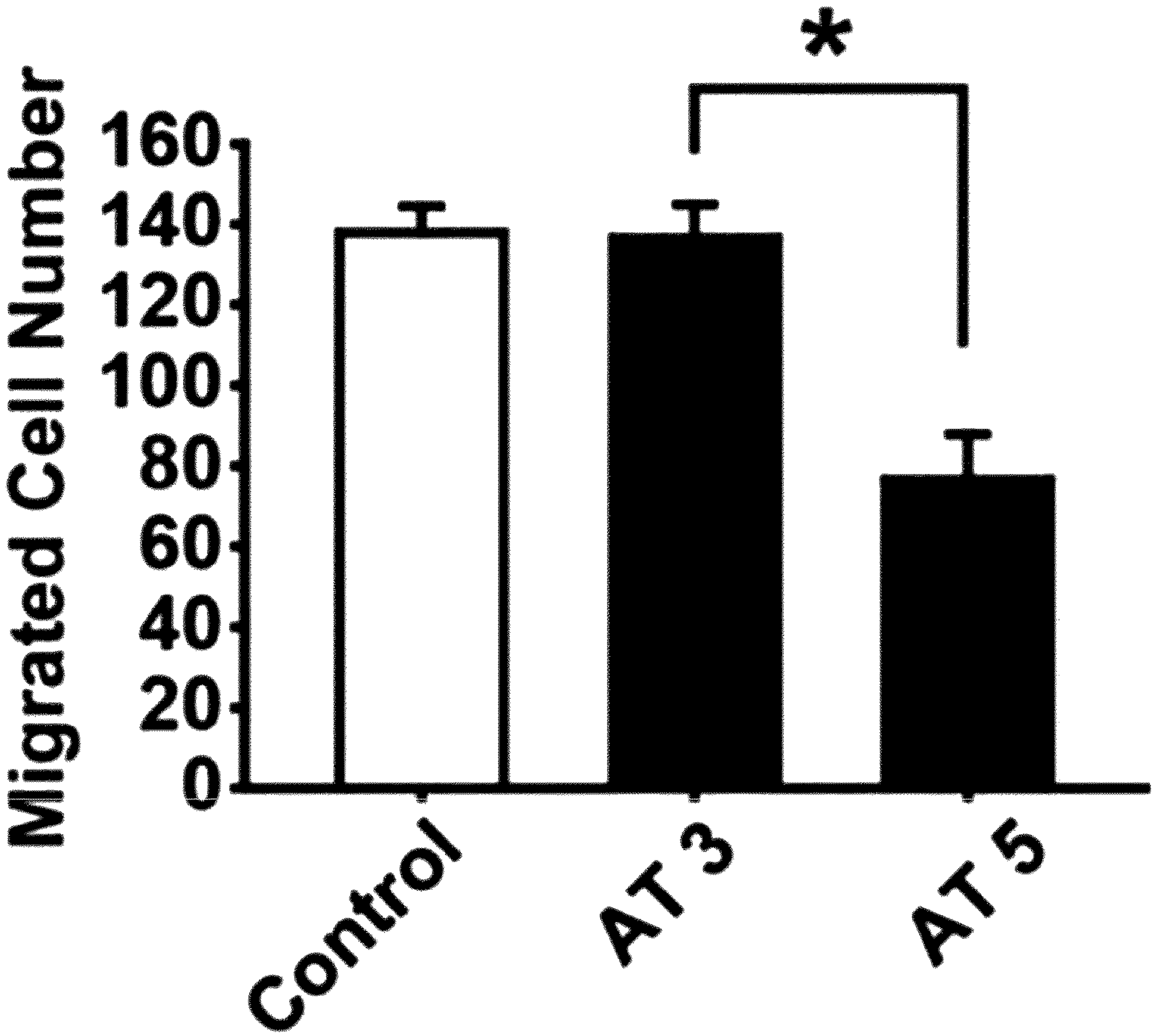

[Fig. 39]
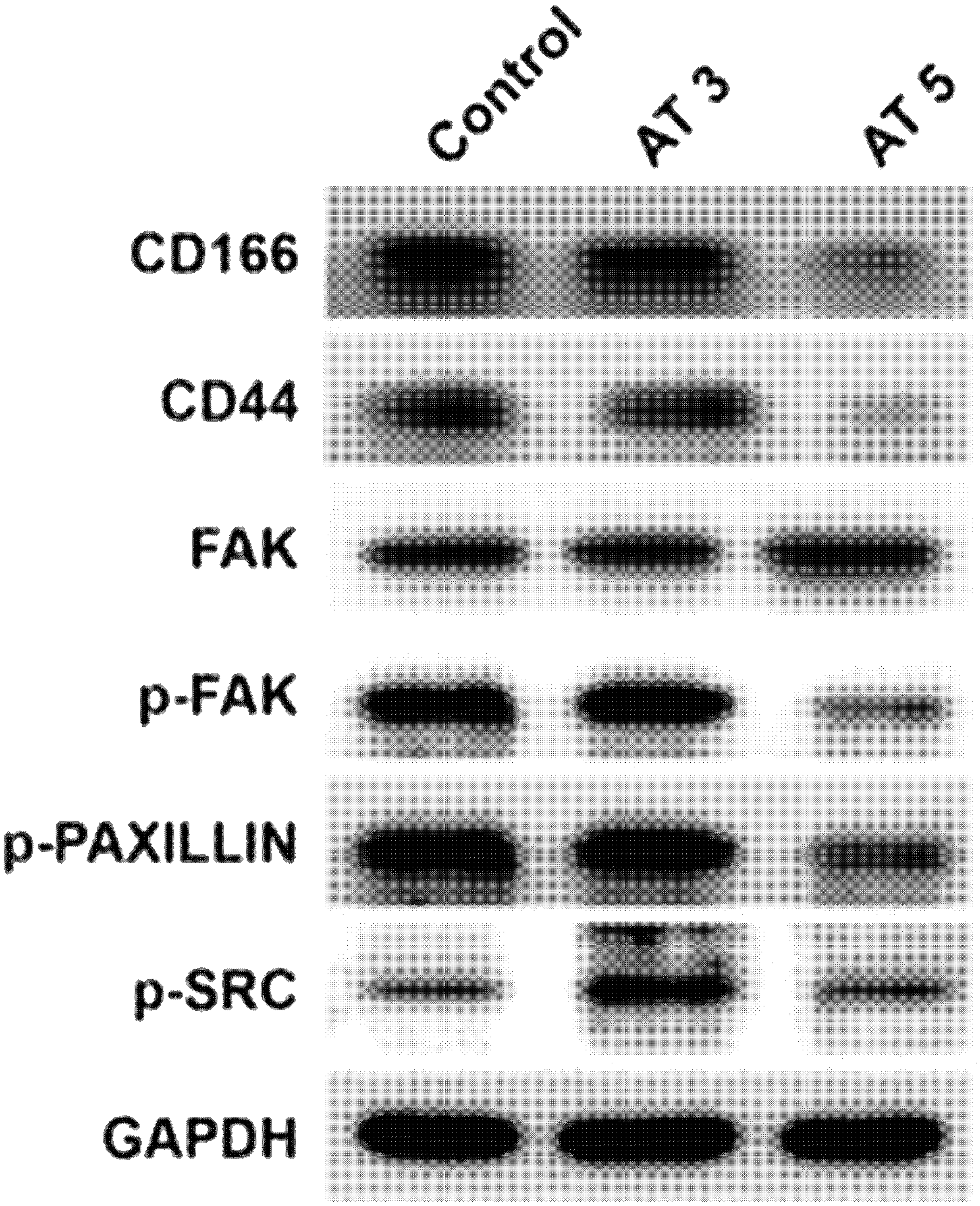

[Fig. 41]
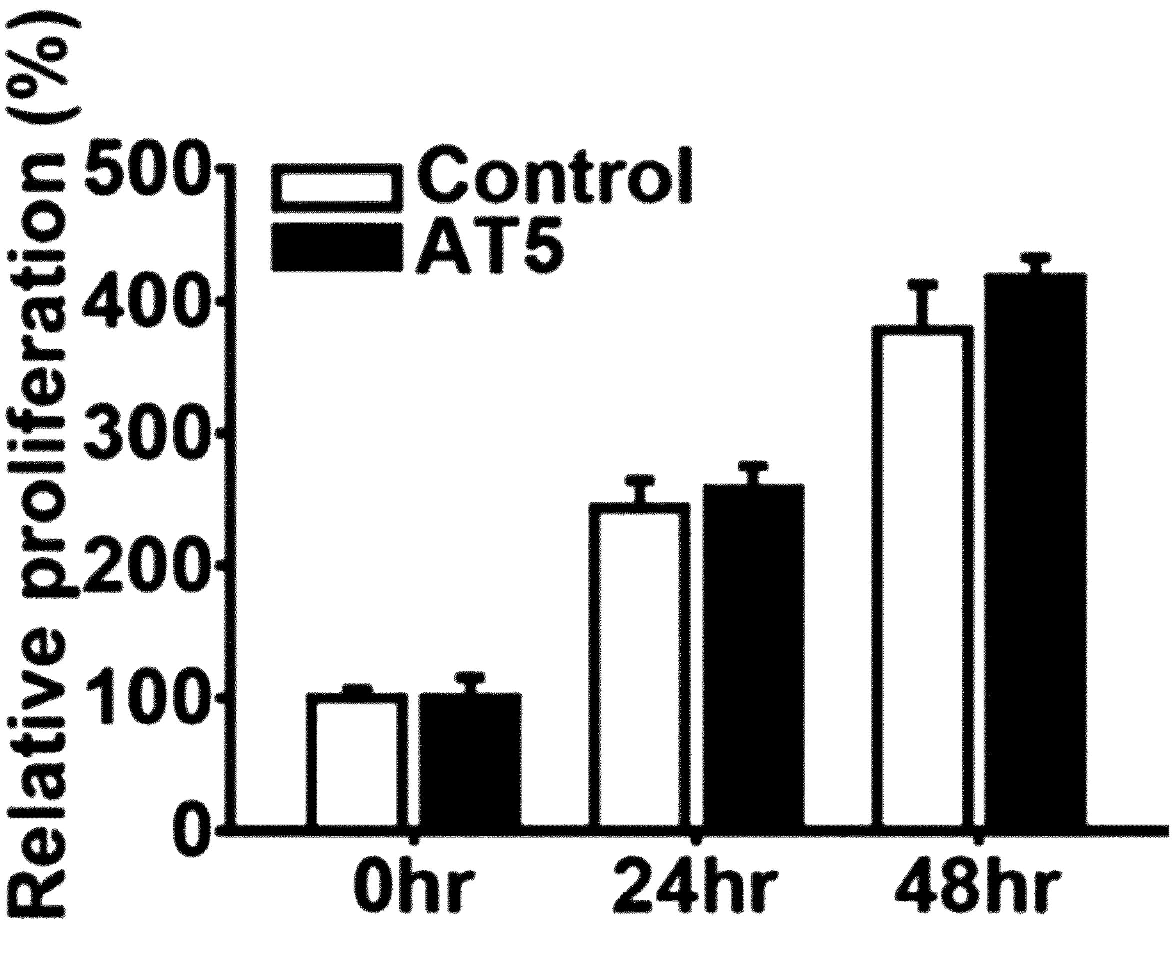

[Fig. 42]
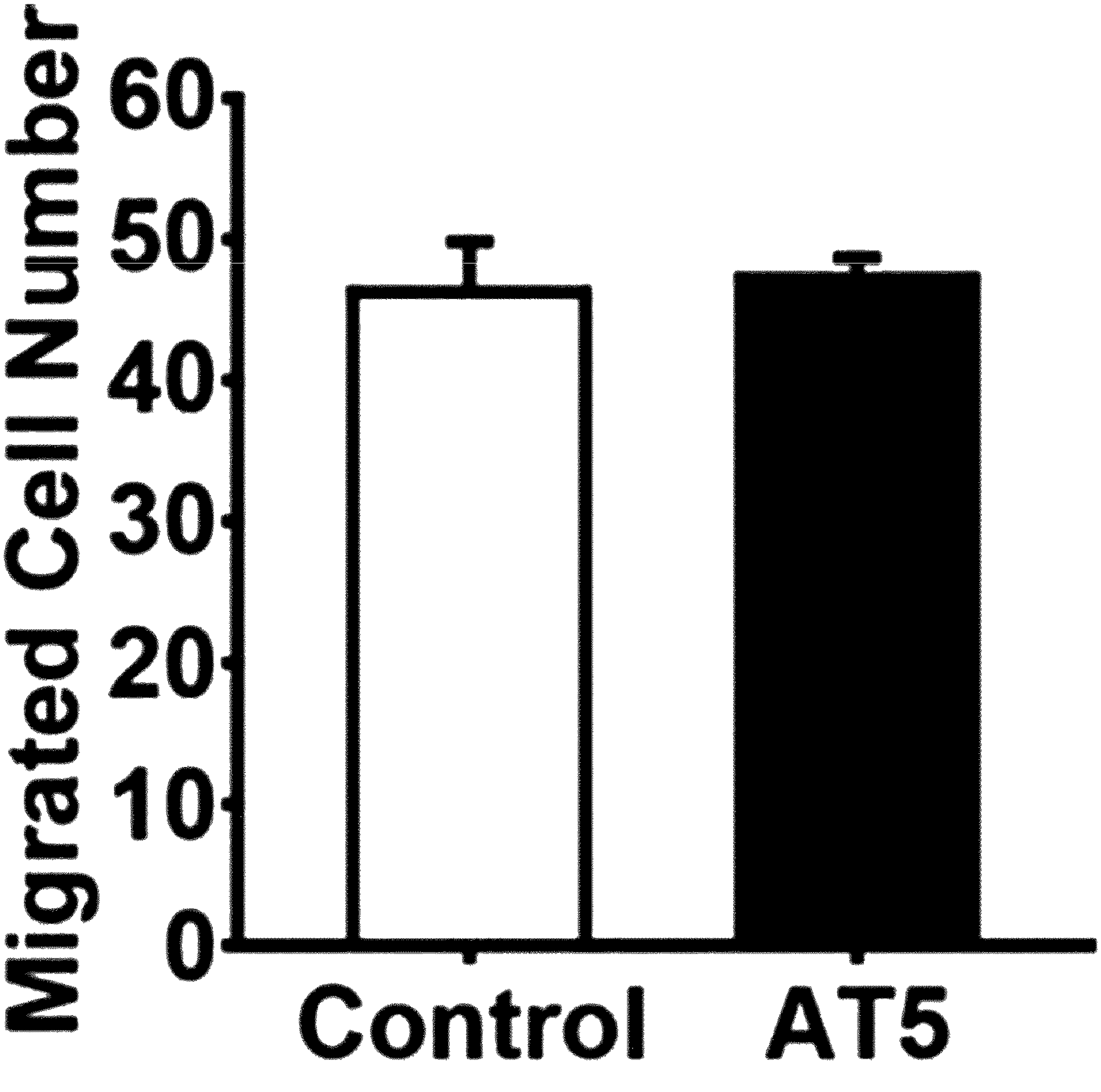

[Fig. 43]
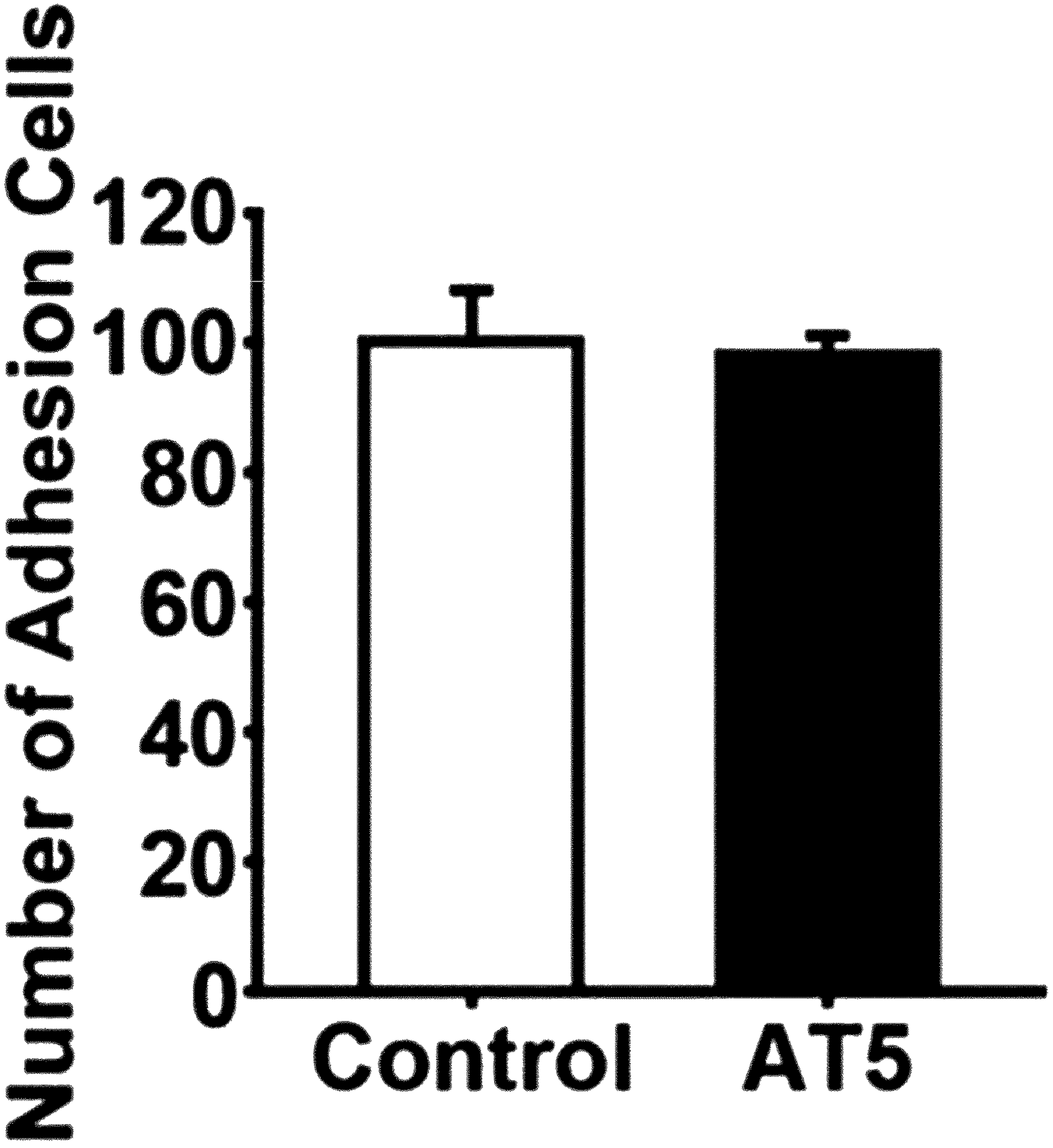

[Fig. 44]
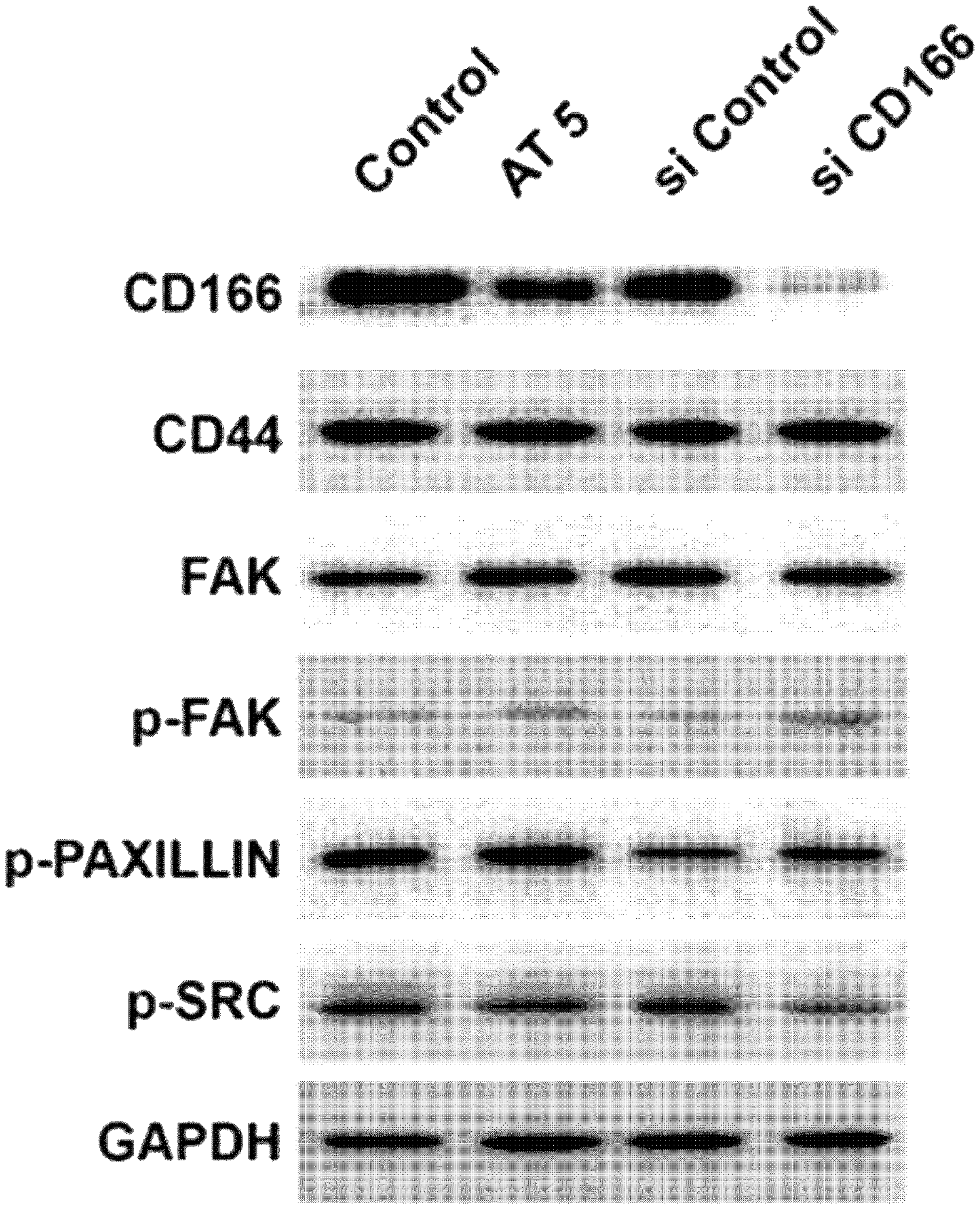

SEQUENCE LISTING

```
<160> NUMBER OF SEQ ID NOS: 26

<210> SEQ ID NO 1
<211> LENGTH: 76
<212> TYPE: DNA
<213> ORGANISM: Artificial Sequence
<220> FEATURE:
<223> OTHER INFORMATION: AT1, clone 1
<220> FEATURE:
<221> NAME/KEY: misc_feature
<222> LOCATION: (20)..(21)
<223> OTHER INFORMATION: 5-(N-naphthylcarboxyamide)-2'-deoxyuridine
<220> FEATURE:
<221> NAME/KEY: misc_feature
<222> LOCATION: (27)..(28)
<223> OTHER INFORMATION: 5-(N-naphthylcarboxyamide)-2'-deoxyuridine
<220> FEATURE:
<221> NAME/KEY: misc_feature
<222> LOCATION: (30)..(30)
<223> OTHER INFORMATION: 5-(N-naphthylcarboxyamide)-2'-deoxyuridine
<220> FEATURE:
<221> NAME/KEY: misc_feature
<222> LOCATION: (35)..(35)
<223> OTHER INFORMATION: 5-(N-naphthylcarboxyamide)-2'-deoxyuridine
<220> FEATURE:
<221> NAME/KEY: misc_feature
<222> LOCATION: (38)..(38)
<223> OTHER INFORMATION: 5-(N-naphthylcarboxyamide)-2'-deoxyuridine
<220> FEATURE:
<221> NAME/KEY: misc_feature
<222> LOCATION: (41)..(41)
<223> OTHER INFORMATION: 5-(N-naphthylcarboxyamide)-2'-deoxyuridine
<220> FEATURE:
<221> NAME/KEY: misc_feature
<222> LOCATION: (44)..(45)
<223> OTHER INFORMATION: 5-(N-naphthylcarboxyamide)-2'-deoxyuridine
<220> FEATURE:
<221> NAME/KEY: misc_feature
<222> LOCATION: (47)..(47)
<223> OTHER INFORMATION: 5-(N-naphthylcarboxyamide)-2'-deoxyuridine
<220> FEATURE:
<221> NAME/KEY: misc_feature
<222> LOCATION: (52)..(52)
<223> OTHER INFORMATION: 5-(N-naphthylcarboxyamide)-2'-deoxyuridine
<220> FEATURE:
<221> NAME/KEY: misc_feature
<222> LOCATION: (54)..(54)
<223> OTHER INFORMATION: 5-(N-naphthylcarboxyamide)-2'-deoxyuridine

<400> SEQUENCE: 1

tcagccgcca gccagttccn ncagccnngn agagncanga ncgnnancgg ancngaggga      60

ccagagcacc acagag                                                      76


<210> SEQ ID NO 2
<211> LENGTH: 76
```

<212> TYPE: DNA
<213> ORGANISM: Artificial Sequence
<220> FEATURE:
<223> OTHER INFORMATION: AT2, clone 2
<220> FEATURE:
<221> NAME/KEY: misc_feature
<222> LOCATION: (20)..(21)
<223> OTHER INFORMATION: 5-(N-naphthylcarboxyamide)-2'-deoxyuridine
<220> FEATURE:
<221> NAME/KEY: misc_feature
<222> LOCATION: (24)..(24)
<223> OTHER INFORMATION: 5-(N-naphthylcarboxyamide)-2'-deoxyuridine
<220> FEATURE:
<221> NAME/KEY: misc_feature
<222> LOCATION: (29)..(30)
<223> OTHER INFORMATION: 5-(N-naphthylcarboxyamide)-2'-deoxyuridine
<220> FEATURE:
<221> NAME/KEY: misc_feature
<222> LOCATION: (36)..(36)
<223> OTHER INFORMATION: 5-(N-naphthylcarboxyamide)-2'-deoxyuridine
<220> FEATURE:
<221> NAME/KEY: misc_feature
<222> LOCATION: (38)..(40)
<223> OTHER INFORMATION: 5-(N-naphthylcarboxyamide)-2'-deoxyuridine
<220> FEATURE:
<221> NAME/KEY: misc_feature
<222> LOCATION: (42)..(42)
<223> OTHER INFORMATION: 5-(N-naphthylcarboxyamide)-2'-deoxyuridine
<220> FEATURE:
<221> NAME/KEY: misc_feature
<222> LOCATION: (44)..(45)
<223> OTHER INFORMATION: 5-(N-naphthylcarboxyamide)-2'-deoxyuridine
<220> FEATURE:
<221> NAME/KEY: misc_feature
<222> LOCATION: (48)..(48)
<223> OTHER INFORMATION: 5-(N-naphthylcarboxyamide)-2'-deoxyuridine
<220> FEATURE:
<221> NAME/KEY: misc_feature
<222> LOCATION: (50)..(50)
<223> OTHER INFORMATION: 5-(N-naphthylcarboxyamide)-2'-deoxyuridine
<220> FEATURE:
<221> NAME/KEY: misc_feature
<222> LOCATION: (53)..(53)
<223> OTHER INFORMATION: 5-(N-naphthylcarboxyamide)-2'-deoxyuridine
<220> FEATURE:
<221> NAME/KEY: misc_feature
<222> LOCATION: (57)..(57)
<223> OTHER INFORMATION: 5-(N-naphthylcarboxyamide)-2'-deoxyuridine

<400> SEQUENCE: 2
tcagccgcca gccagttcan nganaaggnn aggacncnnn cngnnggnan ccncacngga 60
ccagagcacc acagag 76

<210> SEQ ID NO 3
<211> LENGTH: 76
<212> TYPE: DNA
<213> ORGANISM: Artificial Sequence
<220> FEATURE:
<223> OTHER INFORMATION: AT3, clone 3
<220> FEATURE:
<221> NAME/KEY: misc_feature
<222> LOCATION: (23)..(23)
<223> OTHER INFORMATION: 5-(N-naphthylcarboxyamide)-2'-deoxyuridine
<220> FEATURE:
<221> NAME/KEY: misc_feature
<222> LOCATION: (26)..(28)
<223> OTHER INFORMATION: 5-(N-naphthylcarboxyamide)-2'-deoxyuridine
<220> FEATURE:
<221> NAME/KEY: misc_feature
<222> LOCATION: (38)..(38)
<223> OTHER INFORMATION: 5-(N-naphthylcarboxyamide)-2'-deoxyuridine
<220> FEATURE:
<221> NAME/KEY: misc_feature
<222> LOCATION: (48)..(48)
<223> OTHER INFORMATION: 5-(N-naphthylcarboxyamide)-2'-deoxyuridine
<220> FEATURE:

<221> NAME/KEY: misc_feature
<222> LOCATION: (50)..(50)
<223> OTHER INFORMATION: 5-(N-naphthylcarboxyamide)-2'-deoxyuridine
<220> FEATURE:
<221> NAME/KEY: misc_feature
<222> LOCATION: (54)..(56)
<223> OTHER INFORMATION: 5-(N-naphthylcarboxyamide)-2'-deoxyuridine

<400> SEQUENCE: 3
tcagccgcca gccagttcgc gcncgnnncg gaggggangc agaccccncn cgcnnngcga 60
ccagagcacc acagag 76

<210> SEQ ID NO 4
<211> LENGTH: 76
<212> TYPE: DNA
<213> ORGANISM: Artificial Sequence
<220> FEATURE:
<223> OTHER INFORMATION: AT4, clone 4
<220> FEATURE:
<221> NAME/KEY: misc_feature
<222> LOCATION: (20)..(21)
<223> OTHER INFORMATION: 5-(N-naphthylcarboxyamide)-2'-deoxyuridine
<220> FEATURE:
<221> NAME/KEY: misc_feature
<222> LOCATION: (23)..(23)
<223> OTHER INFORMATION: 5-(N-naphthylcarboxyamide)-2'-deoxyuridine
<220> FEATURE:
<221> NAME/KEY: misc_feature
<222> LOCATION: (28)..(28)
<223> OTHER INFORMATION: 5-(N-naphthylcarboxyamide)-2'-deoxyuridine
<220> FEATURE:
<221> NAME/KEY: misc_feature
<222> LOCATION: (31)..(31)
<223> OTHER INFORMATION: 5-(N-naphthylcarboxyamide)-2'-deoxyuridine
<220> FEATURE:
<221> NAME/KEY: misc_feature
<222> LOCATION: (37)..(38)
<223> OTHER INFORMATION: 5-(N-naphthylcarboxyamide)-2'-deoxyuridine
<220> FEATURE:
<221> NAME/KEY: misc_feature
<222> LOCATION: (40)..(40)
<223> OTHER INFORMATION: 5-(N-naphthylcarboxyamide)-2'-deoxyuridine
<220> FEATURE:
<221> NAME/KEY: misc_feature
<222> LOCATION: (47)..(47)
<223> OTHER INFORMATION: 5-(N-naphthylcarboxyamide)-2'-deoxyuridine
<220> FEATURE:
<221> NAME/KEY: misc_feature
<222> LOCATION: (49)..(49)
<223> OTHER INFORMATION: 5-(N-naphthylcarboxyamide)-2'-deoxyuridine
<220> FEATURE:
<221> NAME/KEY: misc_feature
<222> LOCATION: (57)..(57)
<223> OTHER INFORMATION: 5-(N-naphthylcarboxyamide)-2'-deoxyuridine
<220> FEATURE:
<221> NAME/KEY: misc_feature
<222> LOCATION: (64)..(64)
<223> OTHER INFORMATION: 5-(N-naphthylcarboxyamide)-2'-deoxyuridine
<220> FEATURE:
<221> NAME/KEY: misc_feature
<222> LOCATION: (66)..(66)
<223> OTHER INFORMATION: 5-(N-naphthylcarboxyamide)-2'-deoxyuridine

<400> SEQUENCE: 4
tcagccgcca gccagttccn ncnagagnca ngcacgnnan cggaccngnc ggcgaangga 60
ccanancacc acagag 76

<210> SEQ ID NO 5
<211> LENGTH: 76
<212> TYPE: DNA
<213> ORGANISM: Artificial Sequence
<220> FEATURE:
<223> OTHER INFORMATION: AT5, clone 5

<220> FEATURE:
<221> NAME/KEY: misc_feature
<222> LOCATION: (20)..(22)
<223> OTHER INFORMATION: 5-(N-naphthylcarboxyamide)-2'-deoxyuridine
<220> FEATURE:
<221> NAME/KEY: misc_feature
<222> LOCATION: (25)..(25)
<223> OTHER INFORMATION: 5-(N-naphthylcarboxyamide)-2'-deoxyuridine
<220> FEATURE:
<221> NAME/KEY: misc_feature
<222> LOCATION: (31)..(31)
<223> OTHER INFORMATION: 5-(N-naphthylcarboxyamide)-2'-deoxyuridine
<220> FEATURE:
<221> NAME/KEY: misc_feature
<222> LOCATION: (35)..(36)
<223> OTHER INFORMATION: 5-(N-naphthylcarboxyamide)-2'-deoxyuridine
<220> FEATURE:
<221> NAME/KEY: misc_feature
<222> LOCATION: (38)..(38)
<223> OTHER INFORMATION: 5-(N-naphthylcarboxyamide)-2'-deoxyuridine
<220> FEATURE:
<221> NAME/KEY: misc_feature
<222> LOCATION: (47)..(48)
<223> OTHER INFORMATION: 5-(N-naphthylcarboxyamide)-2'-deoxyuridine
<220> FEATURE:
<221> NAME/KEY: misc_feature
<222> LOCATION: (50)..(50)
<223> OTHER INFORMATION: 5-(N-naphthylcarboxyamide)-2'-deoxyuridine
<220> FEATURE:
<221> NAME/KEY: misc_feature
<222> LOCATION: (55)..(55)
<223> OTHER INFORMATION: 5-(N-naphthylcarboxyamide)-2'-deoxyuridine
<220> FEATURE:
<221> NAME/KEY: misc_feature
<222> LOCATION: (58)..(58)
<223> OTHER INFORMATION: 5-(N-naphthylcarboxyamide)-2'-deoxyuridine

<400> SEQUENCE: 5
tcagccgcca gccagttcan nnganaaagc nccgnnancg ggccccnngn agagncanga 60
ccagagcacc acagag 76

<210> SEQ ID NO 6
<211> LENGTH: 76
<212> TYPE: DNA
<213> ORGANISM: Artificial Sequence
<220> FEATURE:
<223> OTHER INFORMATION: AT6, clone 6
<220> FEATURE:
<221> NAME/KEY: misc_feature
<222> LOCATION: (19)..(19)
<223> OTHER INFORMATION: 5-(N-naphthylcarboxyamide)-2'-deoxyuridine
<220> FEATURE:
<221> NAME/KEY: misc_feature
<222> LOCATION: (23)..(25)
<223> OTHER INFORMATION: 5-(N-naphthylcarboxyamide)-2'-deoxyuridine
<220> FEATURE:
<221> NAME/KEY: misc_feature
<222> LOCATION: (29)..(29)
<223> OTHER INFORMATION: 5-(N-naphthylcarboxyamide)-2'-deoxyuridine
<220> FEATURE:
<221> NAME/KEY: misc_feature
<222> LOCATION: (32)..(32)
<223> OTHER INFORMATION: 5-(N-naphthylcarboxyamide)-2'-deoxyuridine
<220> FEATURE:
<221> NAME/KEY: misc_feature
<222> LOCATION: (35)..(35)
<223> OTHER INFORMATION: 5-(N-naphthylcarboxyamide)-2'-deoxyuridine
<220> FEATURE:
<221> NAME/KEY: misc_feature
<222> LOCATION: (43)..(43)
<223> OTHER INFORMATION: 5-(N-naphthylcarboxyamide)-2'-deoxyuridine
<220> FEATURE:
<221> NAME/KEY: misc_feature
<222> LOCATION: (46)..(48)
<223> OTHER INFORMATION: 5-(N-naphthylcarboxyamide)-2'-deoxyuridine
<220> FEATURE:

<221> NAME/KEY: misc_feature
<222> LOCATION: (55)..(55)
<223> OTHER INFORMATION: 5-(N-naphthylcarboxyamide)-2'-deoxyuridine
<220> FEATURE:
<221> NAME/KEY: misc_feature
<222> LOCATION: (57)..(57)
<223> OTHER INFORMATION: 5-(N-naphthylcarboxyamide)-2'-deoxyuridine

<400> SEQUENCE: 6
tcagccgcca gccagttcnc gcnnncggnc ancangaacg gcncgnnncg gaacngncga 60
ccagagcacc acagag 76

<210> SEQ ID NO 7
<211> LENGTH: 20
<212> TYPE: DNA
<213> ORGANISM: Artificial Sequence
<220> FEATURE:
<223> OTHER INFORMATION: Primer sequence

<400> SEQUENCE: 7
cagaacacga tgaggcagac 20

<210> SEQ ID NO 8
<211> LENGTH: 20
<212> TYPE: DNA
<213> ORGANISM: Artificial Sequence
<220> FEATURE:
<223> OTHER INFORMATION: Primer sequence

<400> SEQUENCE: 8
agcaaggagg agaccaacaa 20

<210> SEQ ID NO 9
<211> LENGTH: 21
<212> TYPE: DNA
<213> ORGANISM: Artificial Sequence
<220> FEATURE:
<223> OTHER INFORMATION: Primer sequence

<400> SEQUENCE: 9
tccatgacaa ctttggtatc g 21

<210> SEQ ID NO 10
<211> LENGTH: 20
<212> TYPE: DNA
<213> ORGANISM: Artificial Sequence
<220> FEATURE:
<223> OTHER INFORMATION: Primer sequence

<400> SEQUENCE: 10
tgtagccaaa ttcgttgtca 20

<210> SEQ ID NO 11
<211> LENGTH: 28
<212> TYPE: DNA
<213> ORGANISM: Artificial Sequence
<220> FEATURE:
<223> OTHER INFORMATION: Primer sequence

<400> SEQUENCE: 11
gatcggatcc atggcgggac acctggct 28

<210> SEQ ID NO 12
<211> LENGTH: 18
<212> TYPE: DNA
<213> ORGANISM: Artificial Sequence
<220> FEATURE:
<223> OTHER INFORMATION: Primer sequence

<400> SEQUENCE: 12
ccttcccaaa tagaaccc 18

<210> SEQ ID NO 13
<211> LENGTH: 20
<212> TYPE: DNA
<213> ORGANISM: Artificial Sequence
<220> FEATURE:
<223> OTHER INFORMATION: Primer sequence

<400> SEQUENCE: 13
caacatgatg gagacggagc 20

<210> SEQ ID NO 14
<211> LENGTH: 20
<212> TYPE: DNA
<213> ORGANISM: Artificial Sequence
<220> FEATURE:
<223> OTHER INFORMATION: Primer sequence

<400> SEQUENCE: 14
gtgcatcttg gggttctcct 20

<210> SEQ ID NO 15
<211> LENGTH: 20
<212> TYPE: DNA
<213> ORGANISM: Artificial Sequence
<220> FEATURE:
<223> OTHER INFORMATION: Primer sequence

<400> SEQUENCE: 15
ctcgaaatta agtacaccaa 20

<210> SEQ ID NO 16
<211> LENGTH: 20
<212> TYPE: DNA
<213> ORGANISM: Artificial Sequence
<220> FEATURE:
<223> OTHER INFORMATION: Primer sequence

<400> SEQUENCE: 16
tcagtagacc ctgtgaatgc 20

<210> SEQ ID NO 17
<211> LENGTH: 18
<212> TYPE: DNA
<213> ORGANISM: Artificial Sequence
<220> FEATURE:
<223> OTHER INFORMATION: Primer sequence

<400> SEQUENCE: 17
ccatcagtcc tgttcttg 18

<210> SEQ ID NO 18
<211> LENGTH: 16
<212> TYPE: DNA
<213> ORGANISM: Artificial Sequence
<220> FEATURE:
<223> OTHER INFORMATION: Primer sequence

<400> SEQUENCE: 18
tgctcctctt gcattt 16

<210> SEQ ID NO 19
<211> LENGTH: 20
<212> TYPE: DNA
<213> ORGANISM: Artificial Sequence
<220> FEATURE:
<223> OTHER INFORMATION: Primer sequence

<400> SEQUENCE: 19
ttcagccgtg gaactctttg 20

<210> SEQ ID NO 20
<211> LENGTH: 20
<212> TYPE: DNA
<213> ORGANISM: Artificial Sequence
<220> FEATURE:
<223> OTHER INFORMATION: Primer sequence

<400> SEQUENCE: 20
ccacactctg acctgctgct 20

<210> SEQ ID NO 21
<211> LENGTH: 18
<212> TYPE: DNA
<213> ORGANISM: Artificial Sequence
<220> FEATURE:
<223> OTHER INFORMATION: Primer sequence

<400> SEQUENCE: 21
agacagacgc tgggaccc 18

<210> SEQ ID NO 22
<211> LENGTH: 22
<212> TYPE: DNA
<213> ORGANISM: Artificial Sequence
<220> FEATURE:
<223> OTHER INFORMATION: Primer sequence

<400> SEQUENCE: 22
accatcttgg ctttgaagag tg 22

<210> SEQ ID NO 23
<211> LENGTH: 21
<212> TYPE: DNA
<213> ORGANISM: Artificial Sequence
<220> FEATURE:
<223> OTHER INFORMATION: Synthetic siRNA sequence

<400> SEQUENCE: 23
uucuccgaac gugucacgut t 21

<210> SEQ ID NO 24
<211> LENGTH: 21
<212> TYPE: DNA
<213> ORGANISM: Artificial Sequence
<220> FEATURE:
<223> OTHER INFORMATION: Synthetic siRNA sequence

<400> SEQUENCE: 24
acgugacacg uucggagaat t 21

<210> SEQ ID NO 25
<211> LENGTH: 23
<212> TYPE: RNA
<213> ORGANISM: Artificial Sequence
<220> FEATURE:
<223> OTHER INFORMATION: Synthetic siRNA sequence -continued

```
<400> SEQUENCE: 25

aagcccgaug gcuccccagu auu                                              23

<210> SEQ ID NO 26
<211> LENGTH: 23
<212> TYPE: RNA
<213> ORGANISM: Artificial Sequence
<220> FEATURE:
<223> OTHER INFORMATION: Synthetic siRNA sequence

<400> SEQUENCE: 26

aauacugggg agccaucggg cuu                                              23
```

APTAMER SPECIFICALLY BINDING TO CANCER STEM CELLS, AND USE THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 450124_401USPC_SEQUENCE LISTING.txt. The text file is 6.01 KB, was created on Feb. 24, 2022, and is being submitted electronically via EFS-Web.

REFERENCE TO AN ELECTRONIC SEQUENCE LISTING

The contents of the electronic sequence listing 450124-401USPC-SL.txt; Size: 11,333 bytes; and Date of Creation: Feb. 2, 2026, are herein incorporated by reference in their entirety.

TECHNICAL FIELD

The present invention relates to aptamers that specifically bind to cancer stem cells.

BACKGROUND ART

In cancer tissues, there are also cancer stem cells that maintain and regenerate cancer tissues like normal organs. It has been reported that cancer stem cells form spheres in suspension culture in vitro, and that the sphere-forming cancer stem cells have a stronger tumor-initiating ability than the original cell line. In addition, since cancer stem cells are involved in cancer development, cancer initiation, recurrence, or metastasis as well as resistance to anticancer agents by regenerating cancer cells that have been reduced after conventional cancer treatment has been applied, preventing the proliferation of cancer stem cells is important in cancer treatment.

Currently, in developed countries, information on cancer stem cells in fields such as breast cancer, liver cancer, colorectal cancer, and pancreatic cancer is secured. Thus, there is a need for research on cancer stem cells in organs and tissues, which can be distinct from the research direction of these developed countries.

In the case of cancer, heterogeneity is very strong even within a single tissue, and cancer tissues having resistance to an anticancer agent are expressed during anticancer therapy, so as to this is thought to be the major cause for the failure of anticancer therapy. Cancer stem cells are known to be the highest-level cells exhibiting such heterogeneity characteristics, and are closely related to resistance to an anticancer agent.

While cancer tissue is relatively easily removed by general anticancer therapy, due to the characteristics of cancer stem cells contained in the tissue or acquired after anticancer agent treatment, drug resistance of cancer cells that are constantly expressed despite various targeted treatment techniques is emerging as a recent topic that must be overcome in the treatment of cancer patients. In order to develop anticancer therapy technology targeting cancer stem cells, it is necessary to develop an antibody or an aptamer that can specifically bind to a labeling marker expressed in cancer stem cells.

On the other hand, CD166 was first reported as an activated leukocyte cell adhesion molecule (ALCAM), and its expression was found in thyroid cancer, neck cancer, lung cancer, and liver cancer so far. In particular, it has been reported that the expression of CD166 has been associated with the metastatic potential of prostate cancer, invasiveness of cholangiocarcinoma, and the evasion of apoptosis in breast cancer, and the potential of CD166 as a labeling marker for cancer stem cells has recently been reported. In addition, it has been reported that CD166 is also expressed in mesenchymal stem cells, which are normal stem cells, along with CD40, CD90, and CD105.

In addition, an aptamer is a single-stranded nucleic acid (DNA, RNA, or modified nucleic acid) molecules having a stable tertiary structure, and has the characteristic of being able to bind to a target molecule with high affinity and specificity. Aptamers generally consist of 40 to 120 mer, and can bind to target molecules with intrinsic high affinity (usually pM level) and specificity. An aptamer is being actively studied in the field of clinical cancer diagnosis and cancer treatment, and the reasons are as follows.

1) In vivo immune rejection does not occur.
2) Due to its very small size, penetration and binding thereof in vivo is efficient.
3) Aptamers can be produced in a short time and at a low cost because they are produced by chemical synthesis.
4) Aptamer have higher stability than antibodies. Aptamers can be stored or transported at room temperature, and have high stability for temperature. Thus, aptamers are particularly useful for diagnosis that require long-term and repeated use.
5) Aptamers are nucleic acid molecules that can be modified in various ways, so it can be applied to various studies and experiments.

Because aptamers have the advantages as described above, aptamers can be applied in various ways in the fields of clinical cancer diagnosis and cancer treatment. The first developed aptamer-related drug was approved by the US Food and Drug Administration in 2005.

DETAILED DESCRIPTION OF INVENTION

Technical Problem

Accordingly, the present inventors developed aptamers that specifically bind to CD166 expressed in cancer stem cells, and confirmed that the aptamer reduces the characteristics of cancer stem cells, and has no effect on the proliferation and function of mesenchymal stem cells, which are normal stem cells expressing CD166. Based on the above results, the present inventors completed the present invention.

Therefore, an object of the present invention is to provide an aptamer that specifically binds to cancer stem cells, comprising at least one nucleic acid sequence selected from the group consisting of the nucleic acid sequences representing to SEQ ID NOs: 1 to 6 or a fragment thereof and a composition comprising the same.

Another object of the present invention is to provide a method for diagnosing cancer, comprising reacting a biological sample with the aptamer that specifically binds to cancer stem cells.

Another object of the present invention is to provide a method for treating cancer, comprising administering to a subject the aptamer that specifically binds to cancer stem cells.

Solution to Problem

In order to achieve the above object, the present invention provides aptamers that specifically binds to cancer stem cells, comprising at least one nucleic acid sequence selected from the group consisting of the nucleic acid sequences representing to SEQ ID NOs: 1 to 6 or a fragment thereof.

In addition, the present invention provides a composition for diagnosing cancer, comprising the aptamer that specifically binds to cancer stem cells.

In addition, the present invention provides a kit for diagnosing cancer, comprising the composition for diagnosing cancer.

In addition, the present invention provides a method for diagnosing cancer, comprising reacting a biological sample with the aptamer that specifically binds to cancer stem cells.

In addition, the present invention provides a pharmaceutical composition for preventing or treating cancer, comprising the aptamer that specifically binds to cancer stem cells.

In addition, the present invention provides an anticancer adjuvant composition comprising the aptamer that specifically binds to cancer stem cells.

In addition, the present invention provides a food composition for preventing or alleviating cancer, comprising the aptamer that specifically binds to cancer stem cells.

In addition, the present invention provides a composition for cancer-specific drug delivery, comprising the aptamer that specifically binds to cancer stem cells.

In addition, the present invention provides a method for treating cancer, comprising administering to a subject the aptamer that specifically binds to cancer stem cells.

Effects of Invention

The aptamers according to the present invention specifically bind to cancer stem cells and reduce cell adhesion ability, cell proliferation, drug resistance and cell migration, which are characteristics of cancer stem cells, thus having excellent anticancer effects. Therefore, the aptamer may be used in various ways in the fields of cancer diagnosis, prognosis prediction, and treatment.

BRIEF DESCRIPTION OF DRAWINGS

FIG. 1 illustrates a result obtained by confirming the expression of CD166 in A2780 ovarian cancer cells cultured by attaching the A2780 ovarian cancer cell line to a cell culture dish (A2780-AD), which is a general cell culture method, and in a A2780-SP ovarian cancer stem cell line cultured by three-dimensionally culturing the cells to selectively amplify the cancer stem cells, through RT-PCR analysis.

FIG. 2 illustrates a result obtained by confirming the expression of CD166 in the ovarian cancer stem cell line A2780-SP cells through flow cytometry.

FIG. 3 illustrates a result obtained by confirming the expression of CD166 in CD166 expressing cells and non-expressing cells isolated from the ovarian cancer cell line A2780.

FIG. 4 illustrates a result obtained by confirming the expression of cancer stem cell-related genes in CD166 expressing cells and non-expressing cells isolated from the ovarian cancer cell line A2780.

FIG. 5 illustrates a result obtained by confirming the cell proliferation ability in CD166 expressing cells and non-expressing cells isolated from the ovarian cancer cell line A2780.

FIG. 6 illustrates a result obtained by confirming the globular cancer sphere-forming ability through proliferation of cancer cells during 3D cell culture of CD166 expressing cells and non-expressing cells isolated from the ovarian cancer cell line A2780.

FIG. 7 illustrates a result obtained by confirming the drug sensitivity in CD166 expressing cells and non-expressing cells isolated from the ovarian cancer cell line A2780.

FIG. 8 illustrates a result obtained by confirming the cell migration in CD166 expressing cells and non-expressing cells isolated from the ovarian cancer cell line A2780.

FIG. 9 illustrates a result obtained by confirming the expression of cancer stem cell-related genes in the ovarian cancer cell line A2780 in which the expression of CD166 is inhibited.

FIGS. 10 to 13 illustrate results obtained by confirming cell proliferation ability (FIG. 10), drug resistance (FIG. 11), cancer sphere-forming ability (FIG. 12) and cell migration (FIG. 13) in the ovarian cancer cell line A2780 in which the expression of CD166 is inhibited.

FIG. 14 illustrates a result obtained by confirming the focal adhesion signaling pathway inhibitory activity in CD166 expression-inhibited cells.

FIGS. 15 to 17 illustrate results obtained by confirming the effect of CD166 expression on tumor formation, more specifically, observation of the formed tumor (FIG. 15), tumor size (FIG. 16) and tumor weight (FIG. 17).

FIG. 20 illustrates a result obtained by comparing the affinities of the CD166 aptamer and the antibody to the ovarian cancer stem cell line A2780-SP.

FIGS. 21 to 24 illustrate results obtained by confirming the effect of the CD166 aptamer on cell adhesion ability (FIG. 21), cell proliferation ability (FIG. 22), drug resistance (FIG. 23) and cell migration (FIG. 24) to the ovarian cancer stem cells.

FIG. 25 illustrates a result obtained by confirming the effect of the CD166 aptamer on the focal adhesion signaling pathway in the ovarian cancer stem cells.

FIGS. 26 to 28 illustrate results obtained by confirming the effect of the CD166 aptamer on tumor formation to the ovarian cancer stem cells, more specifically, observation of the formed tumor (FIG. 26), tumor size (FIG. 27) and tumor weight (FIG. 28).

FIG. 29 illustrates a result obtained by confirming the expression of CD166 in the patient-derived ovarian cancer stem cells, through flow cytometry.

FIG. 30 illustrates a result obtained by confirming the effect of CD166 expression inhibition on the focal adhesion signaling pathway in the patient-derived ovarian cancer stem cells.

FIGS. 31 to 35 illustrate results obtained by confirming cell proliferation ability (FIG. 31), drug resistance (FIG. 32), cancer sphere-forming ability (FIG. 33), cell migration (FIG. 34) and cell adhesion ability (FIG. 35) in the patient-derived ovarian cancer stem cells in which the expression of CD166 is inhibited.

FIG. 36A illustrates a result obtained by confirming the affinity of the CD166 aptamer to the patient-derived ovarian cancer stem cells, and FIG. 36B illustrates a result obtained by confirming the cell adhesion ability of the CD166 aptamer to the patient-derived ovarian cancer stem cells.

FIG. 37 illustrates a result obtained by confirming the effect of the CD166 aptamer on drug resistance to the patient-derived ovarian cancer stem cells.

FIG. 38 illustrates a result obtained by confirming the effect of the CD166 aptamer on cell migration to the patient-derived ovarian cancer stem cells.

FIG. 39 illustrates a result obtained by confirming the effect of the CD166 aptamer on the focal adhesion signaling pathway to the patient-derived ovarian cancer stem cells.

FIGS. 41 to 43 illustrate results obtained by confirming the effect of the CD166 aptamer on cell proliferation ability (FIG. 41), cell migration (FIG. 42) and cell adhesion ability (FIG. 43) to mesenchymal stem cells, which are normal stem cells.

FIG. 44 illustrates a result obtained by confirming the effect of the CD166 aptamer and CD166 expression inhibition on the focal adhesion signaling pathway to mesenchymal stem cells, which are normal stem cells.

BEST MODE FOR CARRYING OUT THE INVENTION

Figure 18:
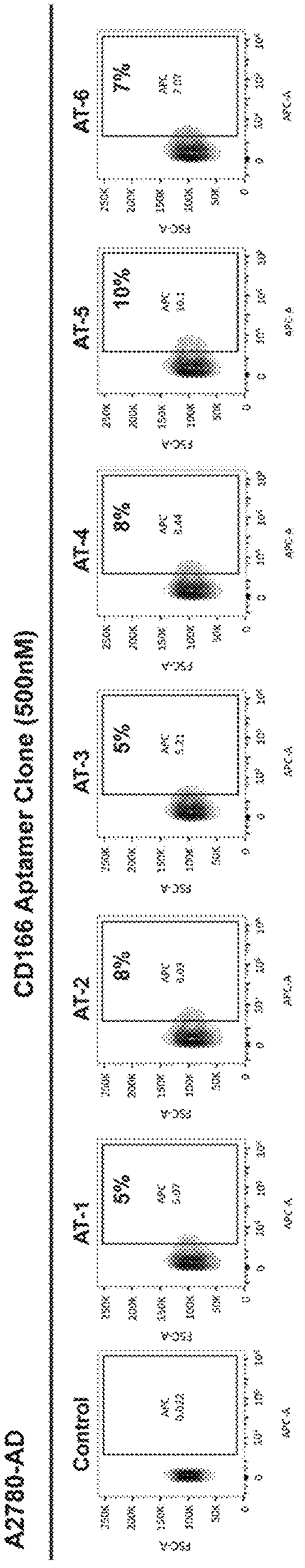
FIGS. 18 and 19 illustrate results obtained by analyzing the affinity between the CD166 aptamer, and the ovarian cancer cell line A2780-AD (FIG. 18) or the ovarian cancer stem cell line A2780-SP (FIG. 19).

Hereinafter, the present invention will be described in detail.

According to an embodiment of the present invention, the present invention provides an aptamer that specifically binds to cancer stem cells, comprising at least one nucleic acid sequence selected from the group consisting of the nucleic acid sequences representing to SEQ ID NOs: 1 to 6 or a fragment thereof.

In the present invention, "aptamer" refers to a small single-stranded oligonucleic acid capable of specifically recognizing a target material with high affinity. In this regard, when the aptamer is RNA, T may be recognized as U in the nucleotide sequence.

The aptamer that specifically binds to cancer stem cells of the present invention preferably includes a nucleic acid sequence having at least 80% homology with SEQ ID NOs: 1 to 6 or a fragment thereof, and most preferably includes at least one nucleic acid sequence selected from the group consisting of the nucleic acid sequences representing to SEQ ID NOs: 1 to 6 or a fragment thereof. The "nucleic acid sequence having at least 80% homology" refers to a nucleic acid sequence in which one to several nucleotides are added, deleted, or substituted to have at least 80% and less then 100% of the sequence in common and show similar CD166 binding ability.

In the present invention, "nucleotide" refers to a unit constituting a nucleic acid. Unless otherwise specified herein, nucleotides A, T (U), G and C are defined as 2'-deoxyadenosine, 2'-deoxythymidine (or 2'-deoxyuridine), 2'-deoxyguanosine and 2'-deoxycytidine, respectively. In addition, 'N' is defined as 5-(N-naphthylcarboxyamide)-2'-deoxyuridine (NapdU), which is represented by the following formula 1.

[Formula 1]

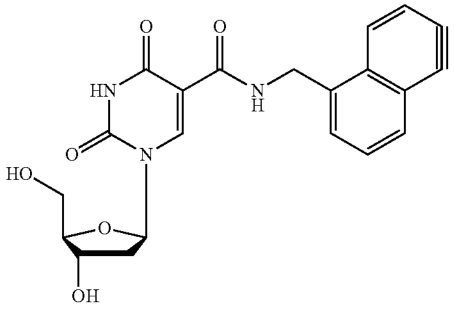

In an embodiment of the present invention, it is preferred that an aptamer that specifically binds to cancer stem cells specifically binds to CD166 expressed in cancer stem cells.

In an embodiment of the present invention, an aptamer that specifically binds to cancer stem cells preferably has a size of 70 to 80 mer, more preferably 74 to 78 mer, and even more preferably 76 mer.

In the present invention, "cancer" is a generic term for diseases caused by cells having an aggressive characteristic in which cells divide and grow ignoring normal growth limits, an invasive characteristic in which cells penetrate into surrounding tissues, and a metastatic characteristic in which cells spread to other parts of the body. The cancer is preferably at least one selected from the group consisting of gastric cancer, breast cancer, lung cancer, liver cancer, blood cancer, bone cancer, pancreatic cancer, skin cancer, head or neck cancer, cutaneous or intraocular melanoma, uterine sarcoma, ovarian cancer, rectal cancer, anal cancer, colon cancer, fallopian tube carcinoma, endometrial carcinoma, cervical cancer, small intestine cancer, endocrine cancer, thyroid cancer, parathyroid cancer, adrenal cancer, soft tissue tumor, urethral cancer, prostate cancer, bronchogenic cancer and bone marrow tumor, but is not limited thereto.

In the present invention, "cancer stem cells" refers to cells having the ability to generate a tumor. Cancer stem cells have the same characteristics as normal stem cells, and specifically have the ability to give rise to all cell types found in a specific cancer sample. That is, cancer stem cells are tumorigenic differently from cancer cells that do not form a tumor. Cancer stem cells generate a tumor in various cell types through the self-renewal and differentiation capacity, which are characteristics of stem cells. In addition, cancer stem cells are distinct from other populations in the tumor and cause recurrence and metastasis by generating a new tumor. Thus, the development of a specific treatment method targeting cancer stem cells may increase the survival rate of cancer patients.

The aptamer that specifically binds to cancer stem cells of the present invention has effects of reducing cell adhesion ability, cell proliferation, drug resistance and cell migration, which are characteristics of cancer stem cells, and may be thus used in various ways in the fields of cancer diagnosis, prognosis prediction, and treatment.

According to another embodiment of the present invention, the present invention provides a composition for diagnosing cancer and a kit for diagnosing cancer, comprising the aptamer that specifically binds to cancer stem cells.

In the present invention, "diagnosis" refers to verifying the presence or characteristics of a pathological condition. The diagnosis is meant to include verifying not only the onset of the disease, but also the prognosis, the course of cancer, the stage, and the like.

By using the composition for diagnosing cancer and the kit for diagnosing cancer of the present invention, cancer stem cells, that is, cells overexpressing CD166, are detected in a biological sample to verify the presence of cancer. In addition, prognosis, course, stage, and the like of cancer as well as the presence of cancer may be verified.

In the present invention, a "biological sample" refers to any sample obtained from a subject in which the expression of the gene or protein of the present invention may be detected. The biological sample is any one selected from the group consisting of whole blood, serum, plasma, cells, sputum, tissue, saliva, biopsy, liquid culture, feces and urine, but is not particularly limited thereto. In addition, it may be prepared by processing by a method commonly used in the technical field of the present invention.

In an embodiment of the present invention, a kit for diagnosing cancer may be a kit in the various forms depending on the method used. For example, it includes a PCR kit, a DNA chip kit, a protein chip kit or a microarray kit or the like, but is not limited thereto.

The kit for diagnosing cancer may include an agent for measuring the expression of the gene or the expression level of the protein thereof, as well as a tool, a reagent, and the like commonly used in the art used for immunological analysis. Examples of the tool or reagent include, but are not limited to, a suitable carrier, a labeling material capable of generating a detectable signal, chromophores, a solubilizer, a detergent, a buffer, a stabilizer, and the like. When the labeling material is an enzyme, it may include a substrate capable of measuring activity of the enzyme and a reaction terminator. The carrier includes a soluble carrier and an insoluble carrier, and an example of the soluble carrier includes a physiologically acceptable buffer known in the art such as PBS, and examples of the insoluble carrier include polystyrene, polyethylene, polypropylene, polyester, polyacrylonitrile, fluororesin, crosslinked dextran, polysaccharide, polymer such as magnetic microparticles plated with metal on latex, other paper, glass, metal, agarose, and combinations thereof.

Since the kit of the present invention includes the above-described composition as a component, redundant descriptions are omitted to avoid excessive complexity of the present specification.

According to another embodiment of the present invention, the present invention provides a method for diagnosing cancer, comprising reacting a biological sample with an aptamer that specifically binds to cancer stem cells.

In an embodiment of the present invention, the method may provide information on the diagnosis of cancer by reacting a biological sample with an aptamer that specifically binds to cancer stem cells, and measuring the degree of reaction (i.e., the degree of expression).

According to another embodiment of the present invention, the present invention provides a pharmaceutical composition for preventing or treating cancer, comprising an aptamer that specifically binds to cancer stem cells.

In addition, the present invention provides a method for treating cancer, comprising administering to a subject an aptamer that specifically binds to cancer stem cells.

When the composition of the present invention is used as a pharmaceutical composition, the pharmaceutical composition of the present invention may be formulated and used in various forms according to a conventional method. For example, it may be formulated in oral formulations such as powders, granules, tablets, capsules, suspensions, emulsions, and syrups, and may be formulated in the form of external preparations, suppositories, and sterile injection solutions.

The composition of the present invention may include one or more known active ingredients having a preventive or therapeutic effect on cancer together with an aptamer that specifically binds to cancer stem cells.

The composition of the present invention may further include a pharmaceutically acceptable additive, wherein as a pharmaceutically acceptable additive, starch, gelatinized starch, microcrystalline cellulose, lactose, povidone, colloidal silicon dioxide, calcium hydrogen phosphate, lactose, mannitol, taffy, gum arabic, pregelatinized starch, corn starch, powdered cellulose, hydroxypropyl cellulose, Opadry, sodium starch glycolate, carnauba wax, synthetic aluminum silicate, stearic acid, magnesium stearate, aluminum stearate, calcium stearate, white sugar, and the like may be used. The pharmaceutically acceptable additive according to the present invention is preferably included in an amount of 0.1 to 90 parts by weight based on the composition, but is not limited thereto.

The composition of the present invention may be administered in various oral or parenteral formulations during actual clinical administration. When the composition is formulated, it may be prepared using diluents or excipients such as fillers, extenders, binders, wetting agents, disintegrants, surfactants, and the like, which are usually used, and it is preferable to use a suitable agent known in the art.

The solid preparation for oral administration includes tablets, pills, powders, granules, capsules, and the like, and the solid preparation is prepared by mixing at least one or more excipient, for example, starch, calcium carbonate, sucrose or lactose, gelatin, and the like. In addition to simple excipients, lubricants such as magnesium stearate and talc are also used. In addition, the liquid preparation for oral administration includes suspensions, internal solutions, emulsions, syrups, and the like. In addition to water and liquid paraffin, which are commonly used simple diluents, various excipients, for example, wetting agents, sweeteners, fragrances, preservatives, and the like may be included.

The preparation for parenteral administration includes sterile aqueous solutions, non-aqueous solvents, suspensions, emulsions, lyophilized preparations, and suppositories. As a non-aqueous solvent and a suspending agent, propylene glycol, polyethylene glycol, vegetable oils such as olive oil, and injectable esters such as ethyl oleate, and the like may be used. As a base of the suppository, witepsol, macrogol, tween 61, cacao butter, laurin butter, glycerogelatin, and the like may be used.

The dosage of the pharmaceutical composition of the present invention may vary depending on the formulation method, mode of administration, administration time and/or route of administration of the pharmaceutical composition, etc. In addition, it may vary depending on various factors including the type and degree of response to be achieved by administration of the pharmaceutical composition, the type, age, body weight, and general health condition of a subject to be administered, symptoms or severity of disease, sex, diet, excretion, drugs or other components of the compositions used together simultaneously or at different times in the subject and similar factors well known in the medical field, and a person skilled in the art may easily determine and prescribe an effective dosage for a desired treatment.

The route and mode of administration of the pharmaceutical composition of the present invention may be each independent, and are not particularly limited in the mode thereof, and any route and mode of administration may be selected as long as the pharmaceutical composition may reach the desired site.

The pharmaceutical composition of the present invention may be used alone or in combination with methods using surgery, radiation therapy, hormone therapy, chemotherapy, and biological response modifiers for the prevention or treatment of cancer.

According to another embodiment of the present invention, the present invention provides an anticancer adjuvant composition comprising an aptamer that specifically binds to cancer stem cells.

The anticancer adjuvant composition of the present invention may be in the form of a pharmaceutical composition or food composition, and more specifically, may be an anticancer pharmaceutical adjuvant or an anticancer food adjuvant.

In the present invention, "anticancer adjuvant" refers to an agent that may be used as an adjuvant to enhance the effect of a cancer therapeutic agent generally used in the art, and the effect of cancer therapeutic agent or anticancer therapy may be enhanced by using the adjuvant according to the present invention.

According to another embodiment of the present invention, the present invention provides a food composition for preventing or alleviating cancer, comprising an aptamer that specifically binds to cancer stem cells.

When the composition of the present invention is used as a food composition, the food composition of the present invention refers to a food having an effect of preventing or alleviating cancer and diseases caused by cancer, and should be harmless to the human body when taken for a long time.

The food is not particularly limited in the type thereof. Examples of foods to which the above substances may be added include meat, sausage, bread, chocolate, candy, snacks, confectionery, pizza, ramen, other noodles, gums, dairy products including ice cream, various soups, beverages, tea, drinks, alcoholic beverages, vitamin complexes, and the like, and include all health foods in the ordinary sense.

In an embodiment of the present invention, the food composition of the present invention may be a food additive. The food additive may be used as it is by adding the aptamer that specifically binds to cancer stem cells or used together with other foods or food ingredients, and may be appropriately used according to a conventional method. The mixed amount of the active ingredient may be appropriately determined according to the purpose of use (prevention, health or therapeutic treatment).

In an embodiment of the present invention, the food composition of the present invention may be a health beverage composition. The health beverage composition may include various flavoring agents or natural carbohydrates as an additional component like a conventional beverage in addition to an aptamer that specifically binds to cancer stem cells. As the above-mentioned natural carbohydrates, monosaccharides such as glucose and fructose, disaccharides such as maltose and sucrose, and natural sweeteners such as dextrin and cyclodextrin, synthetic sweeteners such as saccharin and aspartame, and the like may be used. The proportion of the natural carbohydrates is generally about 0.01 to 10 g, preferably about 0.01 to 0.1 g per 100 ml of the composition of the present invention.

In addition to the above, the composition of the present invention may include various nutrients, vitamins, electrolytes, flavoring agents, coloring agents, pectic acid and a salt thereof, alginic acid and a salt thereof, organic acids, protective colloidal thickeners, pH adjusters, stabilizers, preservatives, glycerin, alcohol, carbonating agents used in carbonated beverages, and the like. In addition, the composition of the present invention may include fruit flesh for the production of natural fruit juice, fruit juice beverage, and vegetable beverage. These components may be used independently or in combination. The proportion of these additives is not critical, but is generally selected in the range of 0.01 to 0.1 parts by weight per 100 parts by weight of the composition of the present invention.

According to another embodiment of the present invention, the present invention provides a composition for cancer-specific drug delivery, comprising an aptamer that specifically binds to cancer stem cells.

The aptamer that specifically binds to cancer stem cells specifically binds to CD166 overexpressed in cancer stem cells. By using this, it is possible to deliver a drug such as an anticancer agent to a site where cancer has occurred.

MODE FOR CARRYING OUT THE INVENTION

Hereinafter, the present invention will be described in more detail through the examples. These examples are only for illustrating the present invention, and it will be apparent to a person skilled in the art that the scope of the present invention is not to be construed as being limited by these examples.

Example 1. Confirmation of CD166 Expression in Ovarian Cancer Cells and Ovarian Cancer Stem Cells RT-PCR was performed to examine the expression of CD166 in ovarian cancer cell line A2780 cells; and the ovarian cancer stem cell line A2780-SP cells isolated and established by three-dimensional culture of A2780 cells. After mRNA was extracted from A2780 and A2780-SP cells, the expression of CD166 was determined by RT-PCR. Specifically, total RNA was isolated from the ovarian cancer cell line A2780 and the ovarian cancer stem cell line A2780-SP cells. For RT-PCR, first-strand-cDNA was synthesized using 2 μg of total RNA and a reverse transcription cDNA synthesis kit (NanoHelix Co.) according to the manufacturer's instructions. Thereafter, 20 μl of a reaction solution containing Ready 2×Go pre-mix PCR kit (NanoHelix Co.) and 10 pM of CD166 specific primer (CD166: 5'-CAGAACACGATGAGGCAGAC-3' (SEQ ID NO: 7), 5'-AGCAAGGAGGAGACCAACAA-3' (SEQ ID NO: 8)) was used to amplify an equal amount of cDNA, and then the expression of CD166 was confirmed. The results of RT-PCR are shown in FIG. 1.

As shown in FIG. 1, it was confirmed that A2780 cells did not express CD166, whereas A2780-SP cells expressed CD166.

In addition, flow cytometry (FACS) was performed to confirm the expression of CD166 in ovarian cancer cell line A2780 cells; and the ovarian cancer stem cell line A2780-SP cells isolated and established by three-dimensional culture of A2780 cells. Specifically, using a CD166 FACS antibody (PE Mouse Anti-Human CD166, Cat:559263, BD Pharminggen), the ovarian cancer cell line A2780 cells; and the ovarian cancer stem cell line A2780-SP cells were stained, and flow cytometry was performed using FACS Canto II (BD Bioscience). The results of confirming the expression of CD166 in the A2780 and A2780-SP cells through flow cytometry are shown in FIG. 2.

As shown in FIG. 2, it was confirmed that the expression level of CD166 was high in A2780-SP cells, which are ovarian cancer stem cell lines.

Example 2. Flow Cytometry Using CD166 in Ovarian Cancer Cell Line and Confirmation of Expression of Major Genes of Cancer Stem Cells CD166 expressing cells and non-expressing cells were isolated from the ovarian cancer cell line A2780 using a flow cytometer (ARIA3), and the expression of various cancer stem cell-related genes was confirmed in the isolated CD166 expressing cells through RT-PCR. Specifically, RNA was isolated from the ovarian cancer cell line A2780 and the ovarian cancer stem cell line A2780-SP cells, and the expression levels of ABC-transporters (ABCB1, ABCG2, ABCC6), which are drug resistance genes, ALDH, which is known as a marker of cancer stem cells, and stem cell ability-related genes (OCT4, SOX2) were confirmed by RT-PCR. For RT-PCR, first-strand-cDNA was synthesized using 2 μg of total RNA and a reverse transcription cDNA synthesis kit (NanoHelix Co.) according to the manufacturer's instructions. 20 μl of a reaction solution containing Ready 2×Go pre-mix PCR kit (NanoHelix Co.) and each 10 pM primer (GAPDH: 5'-TCCATGACAACTTTGGTATCG-3', 5'-TGTAGCCAAATTCGTTGTCA-3'; OCT4A: 5'-GATCGGATCCATGGCGGGACACCTGGCT-3', 5'-CCTTCCCAAATAGAACCC-3'; SOX2: 5'-CAACATGATGGAGACGGAGC-3', 5'-GTGCATCTTGGGGTTCTCCT-3'; ALDH1: 5'-CTCGAAATTA AGTACACCAA-3', 5'-TCAGTAGA CCCTGTGAATGC-3'; ABCB1: 5'-CCATCAGTCCT GTTCTTG-3', 5'-CTGCTCCTCTTGCATTT-3'; ABCG2: 5'-TTCAGCCGTGGAACTCTTTG-3', 5'-CCACACTCTGACCTGCTGCT-3'; ABCC6: 5'-AGACAGACGCTGGGACCC-3', 5'-ACCATCTTGGCTTTGAAGAGTG-3') was used to amplify an equal amount of cDNA, and then the expression of CD166 was confirmed. The results of confirming the expression of CD166 are shown in FIG. 3, and the results of confirming the expression of cancer stem cell-related genes are shown in FIG. 4.

As shown in FIG. 3, it was confirmed that the CD166 expressing cells (CD166+) isolated from the ovarian cancer cell line A2780 expressed CD166, and the non-CD166-expressing cells (CD116-) did not express CD166.

As shown in FIG. 4, it was confirmed that the expression of the ABC-transporters (ABCB1, ABCG2, ABCC6), which are drug resistance-associated genes of cancer stem cells, ALDH, which is known as a marker of cancer stem cells, and stem cell ability-related genes (OCT4, SOX2) was increased.

Example 3. Confirmation of Effect of CD166 Expression on Cell Proliferation, Drug Resistance, Sphere-Forming Ability, and Cell Migration 3-1. Confirmation of Effect of CD166 on Cell Proliferation In order to confirm the effect of CD166 expression on the cell proliferation rate, $1\times10^4$ cells of CD166 expressing cells and non-expressing cells were each attached to a 24 well-plate, and then the cells were separated with 0.25% trypsin EDTA at a certain time every 1 day for 2 days, and the number of cells was measured in a hematocytometer, and the results are shown in FIG. 5.

As shown in FIG. 5, it was confirmed that CD166 expressing cells had a faster proliferation rate than non-expressing cells.

3-2. Confirmation of Effect of CD166 on Sphere-Forming Ability

The self-renewal ability of CD166 expressing cells isolated from ovarian cancer cell lines was confirmed through the sphere formation experiment. In order to confirm the sphere-forming ability according to CD166 expression, CD166 expressing cells and non-expressing cells were isolated from the A2780 cells using a CD166 FACS antibody (PE Mouse Anti-Human CD166, Cat:559263, BD Pharminggen). Thereafter, 100 to 10,000 cells were each seeded in a 24 well-Ultra-Low Attachment culture plate and cultured for 7 days. The results of the sphere formation experiment are shown in FIG. 6.

As shown in FIG. 6, it was observed that CD166 expressing cells formed more spheres than non-expressing cells. The results indicate that CD166 expressing cells have high self-renewal and non-adherent proliferation ability, which are the most important characteristics of stem cells.

3-3. Confirmation of Effect of CD166 on Anticancer Agent Sensitivity

In order to measure the drug sensitivity, $1\times10^4$ cells of CD166 expressing cells and non-expressing cells were each attached to a 96 well-plate. The attached cells were treated with the anticancer agent paclitaxel at concentrations of 0, 0.01, 0.1 and 1 μM and cultured for 48 hours. MTT solution (Sigma-Aldrich, Inc. St. Louis, Mo.) was added to the cultured cells and reacted for 4 hours. After the reaction was completed, the cells were treated with DMSO (sigma-Aldrich), and the absorbance was measured at 570 nm to analyze the drug sensitivity. The results of analyzing the drug sensitivity are shown in FIG. 7.

As shown in FIG. 7, it was confirmed that CD166 expressing cells had resistance to the anticancer agent paclitaxel. The results indicate that CD166 expressing cells are cancer stem cells.

3-4. Confirmation of Effect of CD166 on Migration

In order to confirm whether the expression of CD166 promotes cell migration, the degree of cell migration was confirmed in vitro. Specifically, in order to confirm cell migration, CD166 expressing cells and non-expressing cells were isolated from the A2780 cells using a CD166 FACS antibody (PE Mouse Anti-Human CD166, Cat:559263, BD Pharminggen). Thereafter, cell migration was measured using a 96 well-chemotaxis chamber (Neuro Probe, Gaithersburg, MD) according to the manufacturer's instructions. The results of confirming cell migration are shown in FIG. 8.

As shown in FIG. 8, it was observed that CD166 expressing cells had higher migration capacity than non-expressing cells.

Example 4. Confirmation of the Effects of CD166 Expression Inhibition on Expression of Stem Cell-Related Genes, Cell Proliferation, Drug Resistance, Sphere-Forming Ability, and Cell Migration of Ovarian Cancer Stem Cells CD166 expression was inhibited using siRNA in the ovarian cancer stem cell line A2780-SP, and the expression of various cancer stem cell-related genes was confirmed in CD166 expression-inhibited cells through the RT-PCR method of Examples 1 and 2. Specifically, in order to inhibit the expression of CD166, the control (si Contro) (5'-UUC UCC GAA CGU GUC ACG UTT-3' (SEQ ID NO: 23);

5'-ACG UGA CAC GUU CGG AGA ATT-3' (SEQ ID NO: 24)) and si CD166 (5'-AAG CCC GAU GGC UCC CCA GUA UU-3' (SEQ ID NO: 25); 5'-AAU ACU GGG GAG CCA UCG GGC UU-3' (SEQ ID NO: 26)) were constructed. The expression of CD166 was inhibited by reacting the constructed siRNA and the ovarian cancer stem cell line A2780-SP cells. The results of confirming the expression of cancer stem cell-related genes are shown in FIG. 9.

As shown in FIG. 9, it was confirmed that the expression of the ABC-transporters (ABCB1, ABCG2, ABCC6), which are drug resistance genes of cancer stem cells, the activity of ALDH, which is known as a marker of cancer stem cells (ALDH), and stem cell ability-related genes (OCT4, SOX2) was reduced by inhibiting the expression of CD166 using siRNA.

Next, in the same manner as in Example 2 above, proliferation, drug resistance, sphere-forming ability and cell migration of CD166 expression-inhibited cells were measured, and the results are shown in FIGS. 10 to 13, respectively.

As shown in FIGS. 10 to 13, it was confirmed that CD166 expression-inhibited cells had decreased cell proliferation ability, increased drug sensitivity, and decreased sphere-forming ability and migration. The results indicate that the expression of CD166 plays an important role in function of stem cells in ovarian cancer stem cells.

Example 5. Confirmation of Inhibition of Focal Adhesion Signaling Pathway in Process in which Inhibition of CD166 Expression in Ovarian Cancer Stem Cells Inhibits Characteristics of Cancer Stem Cells CD166 expression was inhibited using siRNA in the ovarian cancer stem cell line A2780-SP, and the focal adhesion signaling pathway was confirmed in CD166 expression-inhibited cells through Western blotting. Specifically, in order to inhibit the expression of CD166, the control (si Control) (5'-UUC UCC GAA CGU GUC ACG UTT-3' (SEQ ID NO: 23); 5'-ACG UGA CAC GUU CGG AGA ATT-3' (SEQ ID NO: 24) and si CD166 (5'-AAG CCC GAU GGC UCC CCA GUA UU-3' (SEQ ID NO: 25); 5'-AAU ACU GGG GAG CCA UCG GGC UU-3' (SEQ ID NO: 26) were constructed. The expression of CD166 was inhibited by reacting the constructed siRNA and the ovarian cancer stem cell line A2780-SP cells, and the cells were cultured after inhibition of expression. After culturing for 48 hours, the cells were collected, and protein expression of FAK, SRC, Paxillin and CD44, which are known as major genes of the focal adhesion signaling pathway, was confirmed through Western blotting. Antibodies against CD166 (ab109215, Abcam), CD44 (5640S, Cell Signaling Technology), p-PAXILLIN (2541S, Cell Signaling Technology), p-SRC (2101S, Cell Signaling Technology), p-FAK (3284S, Cell Signaling Technology), FAK (3285S, Cell Signaling Technology) and GAPDH (MAB374, EMD Milliore Corp, Billerica, MA) were used as primary antibodies. The results of confirming the focal adhesion signaling pathway inhibitory activity in CD166 expression-inhibited cells are shown in FIG. 14.

As shown in FIG. 14, it was confirmed that the expression of p-PAXILLIN and p-SRC, which are involved in cell adhesion, was inhibited in the A2780-SP cells in which the expression of CD166 was inhibited. In particular, it was confirmed that the expression of the p-FAK Y925 site, which is known to be involved in adhesion among the phosphorylation sites of FAX, was reduced in the cells.

Example 6. Confirmation of Effect of CD166 Expression on Tumor Formation

The effect of CD166 expression on tumor formation was confirmed. CD166 expressing cells and non-expressing cells were isolated from the ovarian cancer cell line A2780 using a flow cytometer (ARIA3). $1\times10^5$ cells of the isolated cell were each inoculated subcutaneously into nude mice. At this time, CD166 expressing cells were inoculated on the left side of nude mice, and non-CD166-expressing cells were inoculated on the right side of nude mice, respectively. After inoculation, the tumor formation size was measured from the 18th day. Nude mice were euthanized on the 38th day of inoculation. Tumors were isolated from nude mice, and finally, the weight and size of the tumors were measured. The results of observation of the isolated tumors are shown in FIG. 15, the results of measuring the size of the tumors are shown in FIG. 16, and the results of measuring the weight of the tumors are shown in FIG. 17, respectively.

As shown in FIGS. 15 to 17, it was confirmed that tumors were formed more rapidly in CD166 expressing cells. Likewise, it was confirmed that the tumors were heavier in CD166 expressing cells than those in non-CD166-expressing cells, and their size was also large.

Example 7. Construction of Aptamers that Specifically Bind to CD166 Expressed in Cancer Stem Cells Aptamers that specifically bind to CD166 expressed in cancer stem cells was constructed. The CD166 aptamer (CD166 AT) was synthesized by Aptamer Sciences Inc. (Pohang, Korea). The sequences of the constructed aptamer that specifically binds to CD166 are shown in Table 1.

TABLE 1

| Name | Sequence | Length |
|---|---|---|
| AT1, clone 1 (SEQ ID NO: 1) | TCAGCCGCCAGCCAGTTCCNNCAGCCNN GNAGAGNCANGANCGNNANCGGANCNGA GGGACCAGAGCACCACAGAG | 76-mer |
| AT2, clone 2 (SEQ ID NO: 2) | TCAGCCGCCAGCCAGTTCANNGANAAGG NNAGGACNCNNNCNGNNGGNANCCNCAC NGGACCAGAGCACCACAGAG | 76-mer |
| AT3, clone 3 (SEQ ID NO: 3) | TCAGCCGCCAGCCAGTTCGCGCNCGNNN CGGAGGGGANGCAGACCCCNCNCGCNNN GCGACCAGAGCACCACAGAG | 76-mer |
| AT4, clone 4 (SEQ ID NO: 4) | TCAGCCGCCAGCCAGTTCCNNCNAGAGN CANGCACGNNANCGGACCNGNCGGCGAA NGGACCANANCACCACAGAG | 76-mer |
| AT5, clone 5 (SEQ ID NO: 5) | TCAGCCGCCAGCCAGTTCANNNGANAAA GCNCCGNNANCGGGCCCCNNGNAGAGNC ANGACCAGAGCACCACAGAG | 76-mer |
| AT6, clone 6 (SEQ ID NO: 6) | TCAGCCGCCAGCCAGTTCNCGCNNNCGG NCANCANGAACGGCNCGNNNCGGAACNG NCGACCAGAGCACCACAGAG | 76-mer |

In which, A, T (U), G and C are defined as 2'-deoxyadenosine, 2'-deoxythymidine (or 2'-deoxyuridine), 2'-deoxyguanosine and 2'-deoxycytidine, respectively. 'N' is defined as 5-(N-naphthylcarboxyamide)-2'-deoxyuridine (NapdU), which is represented by the following formula 1.

[Formula 1]

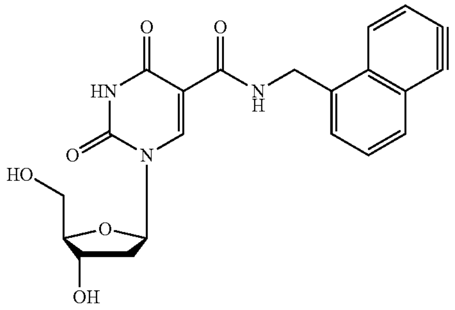

The constructed aptamer was dissolved in sterile tertiary distilled water and then heated to 95° C. for 5 minutes. The heated aptamer was cooled to 25° C. and used in an experiment to be described below.

Example 8. Confirmation of Affinity of CD166 Aptamer in Ovarian Cancer Cells and Ovarian Cancer Stem Cells 8-1. Confirmation of Affinity of CD166 Aptamer to Ovarian Cancer Cells and Ovarian Cancer Stem Cells It was confirmed whether the CD166 aptamer constructed in Example 7 recognized ovarian cancer cells and ovarian cancer stem cells. The following experiment was performed to analyze the interaction between the CD166 aptamer and the ovarian cancer cell line A2780 cells. First, each of the CD166 aptamer (AT-1, AT-2, AT-3, AT-4, AT-5 and AT-6) was dissolved in sterile tertiary water and then heated at 95° C. for 5 minutes. After heating, it was cooled to 25° C. The aptamer was added to the ovarian cancer cell line A2780 cells at a concentration of 500 nM, and then the cells were cultured at room temperature and stained. Thereafter, the cells reacted with the CD166 aptamer were analyzed using a flow cytometer (fluorescence activated cell sorter, FACS), and the results are shown in FIG. 18.

As shown in FIG. 18, it was confirmed that the CD166 aptamer showed interaction with A2780 cells, but the signal intensity was low. This is because the expression of CD166 is low in the ovarian cancer cell line A2780.

Figure 19:
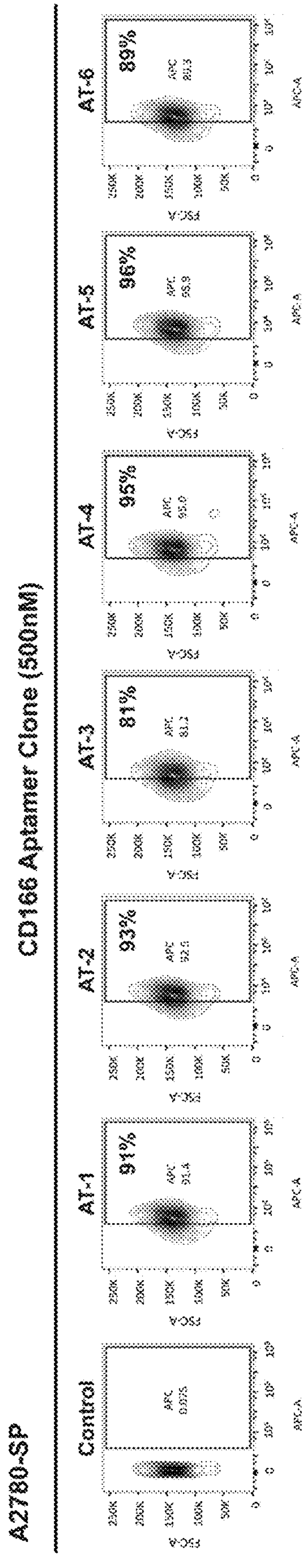

In addition, in the same manner as described above, the ovarian cancer stem cell line A2780-SP cells were reacted with the CD166 aptamer, and then FACS was performed, and the results are shown in FIG. 19.

As shown in FIG. 19, it was confirmed that the CD166 aptamer interacts with the ovarian cancer stem cell line A2780-SP cells, and the signal intensity is high. In particular, it was confirmed that AT-5 among the CD166 aptamers most specifically binds to ovarian cancer stem cells.

8-2. Comparison of Affinity of CD166 Aptamer and CD166 Antibody in Cancer Stem Cells The affinity of the CD166 aptamer AT-5 and the CD166 FACS antibody (PE Mouse Anti-Human CD166, Cat: 559263, BD Pharminggen) as the control to the ovarian cancer stem cell line A2780-SP cells was compared. Comparison of the affinities was performed in the same manner as in Example 8-1, and the results are shown in FIG. 20.

As shown in FIG. 20, it was confirmed that the bindings of the CD166 aptamer and the CD166 antibody to the A2780-SP cells showed similar binding specificities and affinities. The results indicate that the CD166 aptamer specifically binds to CD166 expressing cells, and that this aptamer has a binding affinity similar with to the CD166 antibody.

Example 9. Confirmation of Effects of CD166 Aptamer on Cell Adhesion Ability, Cell Proliferation, Drug Resistance, and Cell Migration of Ovarian Cancer Stem Cells The effect of the CD166 aptamer on cell adhesion ability was confirmed using the CD166 aptamers AT3, AT4 and AT5. Specifically, CD166 expressing cells were isolated from ovarian cancer stem cells using the CD166 FACS antibody. Cell adhesion experiment of the CD166 aptamer was performed using the isolated cells. First, $1\times10^5$ cells were seeded in a 96 well plate and then blocked with 20 μg/ml of collagen for 1 hour. After blocking, 0.1% bovine serum albumin (BSA) was added and incubated for 1 hour to limit non-specific binding. The isolated cells were each exposed to the CD166 aptamer (500 nM) for 1 hour and then fixed with 4% formaldehyde. The fixed cells were stained with hoest33342. The stained cells were observed and counted using a microscope, and the results are shown in FIG. 21.

As shown in FIG. 21, it was confirmed that cell adhesion was reduced in the experimental group treated with the CD166 aptamers AT4 and AT5 that have high affinity.

The effect of the CD166 aptamer on cell proliferation was confirmed using the CD166 aptamer AT5. Specifically, $1\times10^4$ cells of CD166 expressing cells were each attached to a 24-well plate, and then divided into a CD166 aptamer AT-5 treated group and an untreated group, respectively, and treated. After 0, 24, 48 and 72 hours of aptamer treatment, MTT solution (Sigma-Aldrich, Inc. St. Louis, Mo.) was added to the cells and reacted for 4 hours. The cells reacted with the MTT solution were treated with DMSO (sigma-Aldrich), and then the absorbance was measured at 570 nm. The results of confirming the effect of the CD166 aptamer on cell proliferation are shown in FIG. 22.

As shown in FIG. 22, it was confirmed that cell proliferation of cancer stem cells treated with the CD166 aptamer was inhibited.

The effect of the CD166 aptamer on drug sensitivity was confirmed using the CD166 aptamer AT5. Specifically, $1\times10^4$ cells of CD166 expressing cells were each seeded to a 24-well plate and then treated with 0.1 μM of an anticancer agent paclitaxel and the CD166 aptamer AT-5. The control was treated with 0.1 μM of paclitaxel alone. After 0, 24, 48 and 72 hours of aptamer treatment, MTT solution was added to the cells and reacted for 4 hours. The cells reacted with the MTT solution were treated with DMSO, and then the absorbance was measured at 570 nm. The results of confirming the effect of the CD166 aptamer on drug sensitivity are shown in FIG. 23.

As shown in FIG. 23, it was confirmed that the cells treated with the CD166 aptamer had reduced drug resistance, which is characteristic of cancer stem cells.

The effect of the CD166 aptamer on cell migration was confirmed using the CD166 aptamer AT5. Specifically, $1\times10^4$ cells of CD166 expressing cells were each seeded to a 24-well plate, and then divided into a CD166 aptamer AT-5 treated group and an untreated group, respectively, and treated. The degree of migration of the cells treated with the aptamer was confirmed in vitro, and the results are shown in FIG. 24.

As shown in FIG. 24, it was confirmed that the cancer stem cells treated with the CD166 aptamer had reduced cell migration.

The above results indicate that when CD166 expressing cells are treated with aptamers that specifically bind to CD166, cell adhesion, cell proliferation, drug resistance and cell migration, which are the major characteristics of ovarian cancer stem cells, are reduced, thereby inhibiting the characteristics of ovarian cancer stem cells.

Example 10. Confirmation of Inhibition of Focal Adhesion Signaling Pathway in Process in which CD166 Aptamer Inhibits Cell Adhesion Ability in Ovarian Cancer Stem Cells The $CD166^{high}$ cancer cells were isolated from the ovarian cancer stem cell line A2780-SP. The isolated cells were reacted with the CD166 aptamer AT-5 for 1 hour, respectively, and then the focal adhesion signaling pathway was confirmed in CD166 expression-inhibited cells through Western blotting. The Western blotting was performed in the same manner as in Example 5. The results of confirming the focal adhesion signaling pathway in CD166 expression-inhibited cells are shown in FIG. 25.

As shown in FIG. 25, it was confirmed that the expression of p-PAXILLIN and p-SRC, which are involved in cell adhesion, was inhibited in the A2780-SP cells in which the expression of CD166 was inhibited. In particular, it was confirmed that the expression of the p-FAK Y925 site, which is known to be involved in adhesion among the phosphorylation sites of FAX, was reduced in the cells.

Example 11. Confirmation of Effect of CD166 Aptamer on Tumor Formation

The effect of the CD166 aptamer AT-5 on tumor formation was confirmed. Specifically, cells in which the expression CD166 is high were isolated from the ovarian cancer stem cell line A2780-SP using a flow cytometer (ARIA3). The isolated cells were reacted with the CD166 aptamer AT-5 for 1 hour, respectively. The cells reacted with the aptamer ($1\times10^5$ cells) were inoculated subcutaneously into nude mice. At this time, the aptamer-untreated cells were inoculated on the left side of nude mice, and the CD166 aptamer AT-5-treated cells were inoculated on the right side of nude mice. After inoculation, the tumor formation size was measured from the 18th day. Nude mice were euthanized on the 38th day of inoculation. Tumors were isolated from nude mice, and finally, the weight and size of the tumors were measured. The results of observation of the isolated tumors are shown in FIG. 26, the results of measuring the size of the tumors are shown in FIG. 27, and the results of measuring the weight of the tumors are shown in FIG. 28, respectively.

As shown in FIGS. 26 to 28, it was confirmed that tumor formation was inhibited at the site inoculated with the CD166 aptamer AT-5-treated cells, and the size of the tumor was smaller than that of the aptamer untreated group. In addition, it was confirmed that the weight of the tumor at the site inoculated with the CD166 aptamer AT-5-treated cells was reduced significantly than that of the control.

Example 12. Confirmation of CD166 Expression in Patient-Derived Ovarian Cancer Stem Cells Flow cytometry (FACS) was performed to confirm the expression of CD166 in cancer stem cells isolated from ovarian cancer patients. Isolation of patient-derived ovarian cancer cells was performed by the previously described method (STEM CELLS 2016; 34:551-564). More specifically, for flow cytometry, a CD166 FACS antibody (PE Mouse Anti-Human CD166, Cat:559263, BD Pharminggen) was used, and the patient-derived ovarian cancer stem cells were stained. Thereafter, flow cytometry was performed using FACS Canto II (BD Bioscience).

The results of confirming the expression of CD166 in the patient-derived ovarian cancer stem cells through flow cytometry are shown in FIG. 29.

As shown in FIG. 29, it was confirmed that the expression level of CD166 was high in the patient-derived ovarian cancer stem cells.

Example 13. Confirmation of Effects of CD166 Expression Inhibition on Focal Adhesion Signaling Pathway, Cell Proliferation, Drug Resistance, Sphere-Forming Ability, and Cell Migration of Patient-Derived Ovarian Cancer Stem Cells CD166 expression was inhibited using siRNA in the patient-derived ovarian cancer stem cells, and the focal adhesion signaling pathway was confirmed in CD166 expression-inhibited cells through Western blotting. The inhibition of CD166 expression and Western blotting were performed in the same manner as in Examples 4 and 5. The results of confirming the focal adhesion signaling pathway in CD166 expression-inhibited cells are shown in FIG. 30.

As shown in FIG. 30, it was confirmed that the expression of p-PAXILLIN and p-SRC, which are involved in cell adhesion, was inhibited in the patient-derived ovarian cancer stem cells in which the expression of CD166 was inhibited. In particular, it was confirmed that the expression of the p-FAK Y925 site, which is known to be involved in adhesion among the phosphorylation sites of FAX, was reduced in the cells. The expression of cancer stem cell-related genes was confirmed.

Next, in the same manner as in Example 2 above, proliferation, drug resistance, sphere-forming ability, cell migration and cell adhesion of CD166 expression-inhibited cells were measured, and the results are shown in FIGS. 31 to 35, respectively.

As shown in FIGS. 31 to 35, it was confirmed that the patient-derived ovarian cancer stem cells in which the expression of CD166 was inhibited had decreased cell proliferation ability, increased drug sensitivity, and decreased sphere-forming ability, cell migration and cell adhesion. The results indicate that the expression of CD166 plays an important role in function of stem cells in patient-derived ovarian cancer stem cells.

Example 14. Confirmation of Affinity of CD166 Aptamer to Patient-Derived Ovarian Cancer Stem Cells It was confirmed whether the CD166 aptamer AT5, which exhibited high affinity in Example 8, recognized the patient-derived ovarian cancer stem cells. Confirmation of the affinity was performed in the same manner as in Example 8, and the results are shown in FIG. 36A.

As shown in FIG. 36A, it was confirmed that the CD166 aptamer AT5 interacts with the patient-derived ovarian cancer stem cells, and the signal intensity is high.

Example 15. Confirmation of Effects of CD166 Aptamer on Cell Adhesion Ability, Drug Resistance and Cell Migration to Patient-Derived Ovarian Cancer Stem Cells The effects of the CD166 aptamers on cell adhesion ability, drug resistance and cell migration were confirmed using the CD166 aptamers AT3 and AT5. Specifically, the cell adhesion ability, drug resistance and cell migration were performed in the same manner as in Example 9, and the results are shown in FIGS. 36B, 37 and 38, respectively.

As shown in FIGS. 36B, 37 and 38, the results indicate that when the patient-derived ovarian cancer stem cells are treated with aptamers that specifically bind to CD166, cell adhesion, drug resistance and cell migration, which are the major characteristics of cancer stem cells, are reduced, thereby inhibiting the characteristics of patient-derived ovarian cancer stem cells.

Example 16. Confirmation of Inhibition of Focal Adhesion Signaling Pathway in Process in which CD166 Aptamer Inhibits Cell Adhesion Ability in Patient-Derived Ovarian Cancer Stem Cells The patient-derived ovarian cancer stem cells were reacted with the CD166 aptamers AT-3 and AT-5 for 1 hour, respectively, and then the focal adhesion signaling pathway was confirmed in CD166 expression-inhibited cells through Western blotting. The Western blotting was performed in the same manner as in Example 5. The results of confirming the focal adhesion signaling pathway in CD166 expression-inhibited cells are shown in FIG. 39.

As shown in FIG. 39, it was confirmed that the expression of p-PAXILLIN and p-SRC, which are involved in cell adhesion, was inhibited by the CD166 aptamer AT-5. In particular, it was confirmed that the expression of the p-FAK Y925 site, which is known to be involved in adhesion among the phosphorylation sites of FAX, was reduced in the cells.

Example 17. Comparison of Affinities of CD166 Aptamer and CD166 Antibody to Mesenchymal Stem Cells The affinity of the CD166 aptamer AT-5 and the CD166 FACS antibody (PE Mouse Anti-Human CD166, Cat: 559263, BD Pharminggen) as the control to mesenchymal stem cells, which are normal stem cells, was compared. Comparison of the affinities was performed in the same manner as in Example 8-1, and the results are shown in FIG. 40.

Figure 40:
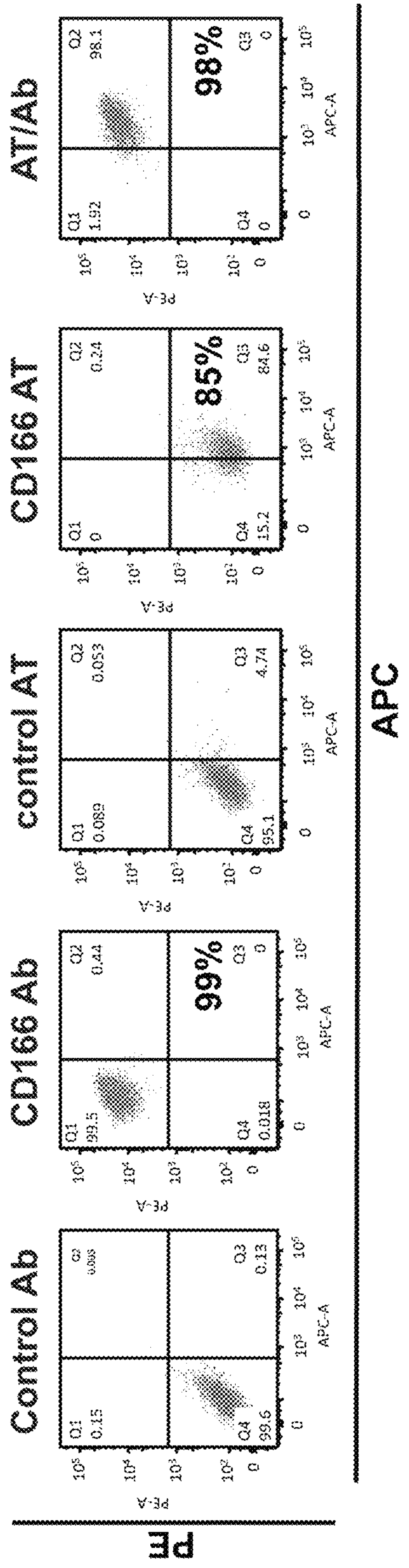
FIG. 40 illustrates a result obtained by comparing the affinities of the CD166 aptamer and the antibody to mesenchymal stem cells, which are normal stem cells.

As shown in FIG. 40, it was confirmed that the binding of the CD166 aptamer and the CD166 antibody to mesenchymal stem cells showed similar binding specificities and affinities. The results indicate that the CD166 aptamer specifically binds to CD166 expressing cells, and that this aptamer has a binding affinity similar with the CD166 antibody.

Example 18. Confirmation of Effects of CD166 Aptamer on Cell Proliferation Ability, Cell Migration, and Cell Adhesion to Mesenchymal Stem Cells The effect of the CD166 aptamer on cell proliferation ability, cell migration and cell adhesion was confirmed using the CD166 aptamer AT5. Specifically, the cell proliferation ability, cell migration and adhesion were performed in the same manner as in Example 9.

As shown in FIGS. 41 to 43, it was confirmed that when mesenchymal stem cells, which are normal stem cells, were treated with aptamers that specifically bind to CD166, there was no change in cell proliferation ability, cell migration and cell adhesion. The results indicate that it does not affect the characteristics of normal stem cells.

Example 19. Confirmation of Focal Adhesion Signaling Pathway in Mesenchymal Stem Cells by CD166 Aptamer and CD166 Expression Inhibition The mesenchymal stem cells were reacted with the CD166 aptamer AT-5 for 1 hour, respectively, and then the focal adhesion signaling pathway was confirmed in CD166 expression-inhibited cells through Western blotting. The Western blotting was performed in the same manner as in Example 5. In addition, the focal adhesion signaling pathway by CD166 expression inhibition in the mesenchymal stem cells was confirmed by the method of Example 4, and the results are shown in FIG. 44.

As shown in FIG. 44, it was confirmed that the expression of p-PAXILLIN and p-SRC, which are involved in cell adhesion, was not affected by the CD166 aptamer AT-5 treatment and CD166 expression inhibition in normal stem cells. In addition, it was confirmed that the expression of the p-FAK Y925 site, which is known to be involved in adhesion among the phosphorylation sites of FAX, was not affected in the cells.

Overall, the present inventors developed aptamers that specifically bind to CD166 expressed in cancer stem cells, and confirmed that the aptamers reduce cell adhesion ability, cell proliferation, drug resistance and cell migration, which are characteristics of cancer stem cells, thus exhibiting anticancer effects. Therefore, the aptamers of the present invention may be used in various ways in the fields of cancer diagnosis, prognosis prediction, and treatment.

Hereinafter, the present invention will be described in more detail through the preparation examples. The preparation examples are only for illustrating the present invention, and the scope of the present invention is not to be construed as being limited by the preparation examples.

Preparation Example 1. Preparation of Pharmaceutical Composition for Preventing or Treating Cancer 1-1. Preparation of Powders 1 mg of an aptamer that specifically binds to cancer stem cells 100 mg of lactose 10 mg of talc The above ingredients are mixed and filled in an airtight bag to prepare a powder.

1-2. Preparation of Tablets 1 mg of an aptamer that specifically binds to cancer stem cells 100 mg of corn starch 100 mg of lactose 2 mg of magnesium stearate The above ingredients are mixed and then tableted according to a conventional method of manufacturing tablets to prepare a tablet.

1-3. Preparation of Capsules 1 mg of an aptamer that specifically binds to cancer stem cells 3 mg of crystalline cellulose 14.8 mg of lactose 0.2 mg of magnesium stearate According to a conventional method of manufacturing capsules, the above ingredients are mixed and filled in a gelatin capsule to prepare a capsule.

1-4. Preparation of Injections 1 mg of an aptamer that specifically binds to cancer stem cells 180 mg of mannitol 2974 mg of sterile distilled water for injection 26 mg of $Na_2HPO_4.2H_2O$ According to a conventional method of manufacturing injections, a injection is prepared in the content of the above ingredients per 1 ampoule (2 ml).

1-5. Preparation of Liquids 1 mg of an aptamer that specifically binds to cancer stem cells 10 g of isomerose 5 g of mannitol Appropriate amount of purified water According to a conventional method of manufacturing liquids, each ingredient is added and dissolved in purified water, an appropriate amount of lemon flavor is added, then the above ingredients are mixed, then purified water is added to adjust to a total of 100 ml, and then filled in a brown bottle and sterilized to prepare a liquid.

Hereinbefore, specific parts of the present invention are described in detail. It is clear to a person skilled in the art that these specific descriptions are only preferred embodiments, and the scope of the present invention is not limited thereby. Therefore, it is intended that the substantial scope of the present invention be defined by the appended claims and their equivalents.

The invention claimed is:

1. An aptamer that specifically binds to cancer stem cells, comprising a nucleic acid sequence represented by SEQ ID NO: 4 or SEQ ID NO: 5.

2. The aptamer that specifically binds to cancer stem cells according to claim 1, wherein the aptamer specifically binds to human CD166.

3. The aptamer that specifically binds to cancer stem cells according to claim 1, wherein the aptamer has a size of 70 to 80 mer.

4. The aptamer that specifically binds to cancer stem cells according to claim 1, wherein the cancer stem cells are at least one selected from the group consisting of breast cancer stem cells, lung cancer stem cells, ovarian cancer stem cells, and colon cancer stem cells.

5. A composition for diagnosing cancer, comprising the aptamer that specifically binds to cancer stem cells according to claim 1,
wherein the cancer is at least one selected from the group consisting of breast cancer, lung cancer, ovarian cancer and colon cancer.

6. A kit for diagnosing cancer, comprising the composition for diagnosing cancer according to claim 5,
wherein the cancer is at least one selected from the group consisting of breast cancer, lung cancer, ovarian cancer and colon cancer.

7. The kit for diagnosing cancer according to claim 6, wherein the kit for diagnosing cancer is a PCR kit, a DNA chip kit, a protein chip kit, or a microarray kit.

8. A method for diagnosing cancer, comprising:
reacting a biological sample with the aptamer that specifically binds to cancer stem cells according to claim 1, wherein the cancer is at least one selected from the group consisting of breast cancer, lung cancer, ovarian cancer and colon cancer.

9. A pharmaceutical composition comprising the aptamer that specifically binds to cancer stem cells according to claim 1,
wherein the cancer is at least one selected from the group consisting of breast cancer, lung cancer, ovarian cancer and colon cancer.

10. An anticancer adjuvant composition comprising the aptamer that specifically binds to cancer stem cells according to claim 1,
wherein the cancer is at least one selected from the group consisting of breast cancer, lung cancer, ovarian cancer and colon cancer.

11. A food composition comprising the aptamer that specifically binds to cancer stem cells according to claim 1,
wherein the cancer is at least one selected from the group consisting of breast cancer, lung cancer, ovarian cancer and colon cancer.

12. A composition for cancer-specific drug delivery, comprising the aptamer that specifically binds to cancer stem cells according to claim 1,
wherein the cancer is at least one selected from the group consisting of breast cancer, lung cancer, ovarian cancer and colon cancer.

13. A method for treating cancer, comprising:
administering to a subject the aptamer that specifically binds to cancer stem cells according to claim 1,
wherein the cancer is at least one selected from the group consisting of breast cancer, lung cancer, ovarian cancer and colon cancer.

* * * * *